(12) United States Patent
Kumar-Singh et al.

(10) Patent No.: US 8,877,896 B2
(45) Date of Patent: Nov. 4, 2014

(54) COMPOSITIONS, METHODS AND KITS FOR MODELING, DIAGNOSING, AND TREATING COMPLEMENT DISORDERS

(71) Applicant: Tufts University, Boston, MA (US)

(72) Inventors: Rajendra Kumar-Singh, Boston, MA (US); Siobhan M. Cashman, Boston, MA (US); John Harry Sweigard, Dorchester, MA (US)

(73) Assignee: Tufts University, Boston, MA (US)

( * ) Notice: Subject to any disclaimer, the term of this patent is extended or adjusted under 35 U.S.C. 154(b) by 0 days.

(21) Appl. No.: 13/692,734

(22) Filed: Dec. 3, 2012

(65) Prior Publication Data

US 2013/0149373 A1 Jun. 13, 2013

Related U.S. Application Data

(63) Continuation-in-part of application No. 12/867,566, filed as application No. PCT/US2009/000947 on Feb. 13, 2009, now Pat. No. 8,324,182, application No. 13/692,734, which is a continuation of application No. PCT/US2011/045933, filed on Jul. 29, 2011.

(60) Provisional application No. 61/066,062, filed on Feb. 15, 2008, provisional application No. 61/066,288, filed on Feb. 19, 2008, provisional application No. 61/070,650, filed on Mar. 25, 2008, provisional application No. 61/480,082, filed on Apr. 28, 2011, provisional application No. 61/445,430, filed on Feb. 22, 2011, provisional application No. 61/441,501, filed on Feb. 10, 2011, provisional application No. 61/368,931, filed on Jul. 29, 2010.

(51) Int. Cl.
| | | |
|---|---|---|
| *C07K 1/00* | (2006.01) |
| *C07K 14/00* | (2006.01) |
| *C07K 17/00* | (2006.01) |
| *A61K 38/00* | (2006.01) |
| *C12Q 1/02* | (2006.01) |
| *G01N 33/564* | (2006.01) |
| *C07K 14/705* | (2006.01) |

(52) U.S. Cl.
CPC ............ *C12Q 1/025* (2013.01); *G01N 2500/10* (2013.01); *G01N 2800/16* (2013.01); *A61K 38/00* (2013.01); *G01N 2333/4716* (2013.01); *G01N 33/564* (2013.01); *C07K 14/70596* (2013.01)
USPC .......................................... 530/350; 530/395

(58) Field of Classification Search
None
See application file for complete search history.

(56) References Cited

U.S. PATENT DOCUMENTS

| 4,405,712 A | 9/1983 | Van de Woude et al. |
|---|---|---|
| 4,650,764 A | 3/1987 | Temin |
| 4,861,719 A | 8/1989 | Miller |
| 4,980,289 A | 12/1990 | Temin |
| 5,122,767 A | 6/1992 | Cameron |
| 5,124,263 A | 6/1992 | Temin |
| 5,624,837 A | 4/1997 | Fodor et al. |
| 5,627,264 A * | 5/1997 | Fodor et al. .................... 530/350 |
| 5,846,715 A | 12/1998 | Purcell et al. |
| 7,166,568 B1 | 1/2007 | Sims et al. |
| 2006/0154336 A1* | 7/2006 | Wijesuriya et al. .......... 435/69.1 |
| 2010/0120665 A1 | 5/2010 | Kaleko et al. |

FOREIGN PATENT DOCUMENTS

| WO | 8505629 A1 | 12/1985 |
|---|---|---|
| WO | 8907150 A1 | 8/1989 |
| WO | 9002797 A1 | 3/1990 |
| WO | 9002806 A1 | 3/1990 |
| WO | 9013641 A1 | 11/1990 |
| WO | 9205266 A2 | 4/1992 |
| WO | 9207943 A1 | 5/1992 |
| WO | 9214829 A1 | 9/1992 |
| WO | 9314188 A1 | 7/1993 |
| WO | WO 9634965 A2 * | 11/1996 |
| WO | WO 2006042329 A2 * | 4/2006 |

OTHER PUBLICATIONS

Wiesmann et al. "Structure of C3b in complex with CRIg gives insights into regulation of complement activation" Nature 2006, 444 (7116), pp. 217-220.*
Anderson et al, "The pivotal role of the complement system in aging and age-related macular degeneration: hypothesis re-visited", 2010, Prog Retin Eye Res 29:95-112.
Barilla-Labarca et al. "Role of membrane cofactor protein (CD46) in regulation of C4b and C3b deposited on cells", 2002, J Immunol 168(12): 6298-6304.
Benzaquen et al. "Terminal complement proteins C5b-9 release basic fibroblast growth factor and platelet-derived growth factor from endothelial cells", 1994, J Exp Med 179: 985-992.
Bora et al, "Recombinant membrane-targeted form of CD59 inhibits the growth of choroidal neovascular complex in mice", 2010, J Biol Chem 285: 33826-33833.
Bringmann et al. "Muller cells in the healthy and diseased retina", 2006, Prog Retin Eye Res 25: 397-424.
Brodbeck et al. "Cooperation between decay-accelerating factor and membrane cofactor protein in protecting cells from autologous complement attack", 2000, J Immunol 165 (7): 3999-4006.

(Continued)

*Primary Examiner* — Daniel E Kolker
*Assistant Examiner* — James Rogers
(74) *Attorney, Agent, or Firm* — Lawson & Weitzen LLP; Sonia K. Guterman; Preeti T. Arun

(57) ABSTRACT

Systems, compositions, methods, and kits for identifying potential therapeutic agents for treatment of complement based ocular diseases are provided herein. The methods and kits include a complement component 3 (C3) protein or derivative that is contacted to ocular cells or tissue. Another embodiment of the invention herein provides for diagnosis and/or prognosis of a complement-associated ocular disease. Compositions, methods and kits for regulating or treating a complement-related condition using at least one of CD46 protein, CD55 protein, and a recombinant chimeric soluble terminator of activated complement (STAC) protein or source of the STAC protein. The STAC protein includes an amino acid sequence including at least two of an amino acid sequence of a CD59 protein, an amino acid sequence derived from a CD46 protein, and an amino acid sequence derived from a CD55 protein, optionally further comprising a linker to connect amino acid sequences.

7 Claims, 25 Drawing Sheets

(56) References Cited

OTHER PUBLICATIONS

Campochiaro et al. "Adenoviral vector-delivered pigment epithelium-derived factor for neovascular age-related macular degeneration: results of a phase I clinical trial", 2006, Hum Gene Ther 17:167-176.
Caprioli et al. "Genetics of HUS: the impact of MCP, CFH, and IF mutations on clinical presentation, response to treatment, and outcome", 2006, Blood 108 (4): 1267-1279.
Cashman et al. "Intercellular trafficking of adenovirus-delivered HSV VP22 from the retinal pigment epithelium to the photoreceptors-implications for gene therapy", 2002 Mol Ther 6: 813-823.
Cashman et al. "Adenovirus type 5 pseudotyped with adenovirus type 37 fiber uses sialic acid as a cellular receptor", 2004, Virology 324(1): 129-39.
Cashman et al. "Inhibition of choroidal neovascularization by adenovirus-mediated delivery of short hairpin RNAs targeting VEGF as a potential therapy for AMD", 2006, Invest Ophthalmol Vis Sci 47: 3496-3504.
Cashman et al. "A Non Membrane-Targeted Human Soluble CD59 Attenuates Choroidal Neovascularization in a Model of Age Related Macular Degeneration", 2011, PLoS ONE, e19078, 6(4): 1-9,.
Chevez-Barrios et al. "Response of retinoblastoma with vitreous tumor seeding to adenovirus-mediated delivery of thymidine kinase followed by ganciclovir", 2005 J Clin Oncol 23: 7927-7935.
Coffey et al. "Complement factor H deficiency in aged mice causes retinal abnormalities and visual dysfunction", 2007, Proc Natl Acad Sci USA 104: 16651-16656.
Cole et al. "Beyond lysis: how complement influences cell fate", 2003, Clinical Science 104: 455-466.
Edwards et al. "Molecular genetics of AMD and current animal models", 2007, Angiogenesis 10: 119-132.
Fisher et al. "Cellular remodeling in mammalian retina: results from studies of experimental retinal detachment", 2005, Prog Retin Eye Res 24: 395-431.
Gao et al. "Cooperation of decay-accelerating factor and membrane cofactor protein in regulating survival of human cervical cancer cells", BMC Cancer, 2009, BMC Cancer 9: 384 (8 pgs.).
Gehrs et al. "Complement age-related macular degeneration and a vision of the future", 2010, Arch Opthalmol 128: 349-358.
Gerl et al. "Extensive deposits of complement C3d and C5b-9 in the choriocapillaris of eyes of patients with diabetic retinopathy", 2002, Invest Ophthalmol Vis Sci 43:1104-08.
Gerth, "The Role of the ERG in the diagnosis and treatment of age-related macular degeneration", 2009, Doc Ophtalmol 118: 63-68.
Gold et al. "Variation in factor B (BF) and complement component 2 (C2) genes is associated with age-related macular degeneration", 2006, Nat Genet 38: 458-462.
Grossniklaus et al. "Animal models of choroidal and retinal neovascularization", 2010, Prog Retin Eye Res 29(6): 500-519.
Guidry, "The role of Muller cells in fibrocontractive retinal disorders", 2005, Prog Retin Eye Res 24: 75-86.
Hageman et al. "An integrated hypothesis that considers drusen as biomarkers of immune-mediated processes at the RPE-Bruch's membrane interface in aging and age-related macular degeneration", 2001, Prog Retin Eye Res 20(6): 705-732.
He et al. "A simplified system for generating recombinant adenoviruses", 1998, Proc Natl Acad Sci USA 95: 2509-2514.
Hu et al. "Differences in the temporal expression of regulatory growth factors during choroidal neovascular development", 2009, Exp Eye Res 88: 79-91.
Johnson et al. "Complement activation and inflammatory processes in drusen formation and age related macular degeneration", 2001, Exp Eye Res 73:887-896.
Kavanagh et al. "Membrane cofactor protein and factor I: mutations and transplantation", 2006, Semin Thromb Hemost 32(2): 155-159.
Kavanagh et al. "Complement regulatory genes and hemolytic uremic syndromes", 2008, Annu Rev Med 59: 293-309.
Kim et al. "Membrane complement regulatory proteins", 2006, Clin Immunol 118: 127-136.
Kimberley et al. "Alternative roles for CD59", 2007, Mol Immunol 44: 73-81.
Klein et al. "Fifteen-year cumulative incidence of age-related macular degeneration: The Beaver Dam Eye Study", 2007, Ophthamology 114: 253-262.
Klein et al. "Retinal precursors and the development of geographic atrophy in age-related macular degeneration", 2008, Ophthamology 115: 1026-1031.
Klos et al. "The role of the anaphylatoxins in health and disease", 2009, Mol Immunol 46: 2753-2766.
Kuehn et al. "Disruption of the complement cascade delays retinal ganglion cell death following retinal ischemia-reperfusion", 2008, Exp Eye Res 87: 89-95.
Kumar-Singh et al. "Construction of encapsidated (gutted) adenovirus minichromosomes and their application to rescue of photoreceptor degeneration", 2000, Methods Enzymol 316: 724-743.
Lamartina et al. "Helper-dependent adenovirus for the gene therapy of proliferative retinopathies: stable gene transfer, regulated gene expression and therapeutic efficacy", 2007, J Gene Med 9:862-874.
Levero et al. "Defective and nondefective adenovirus vectors for expressing foreign genes in vitro and in vivo", 1991 Gene 101: 195-202.
Licht et al. "Hereditary and acquired complement dysregulation in membranoproliferative glomerulonephritis", 2009 Thromb Haemost 101: 271-278.
Lopez et al. "Transdifferentiated retinal pigment epithelial cells are immunoreactive for vascular endothelial growth factor in surgically excised age-related choroidal neovascular membranes", 1996, Invest Ophthalmol Vis Sci 37:855-868.
Lublin et al. "Decay-accelerating factor: biochemistry, molecular biology, and function", 1989, Annu Rev Immunol 7: 35-58.
Lundh Von Leithner et al. "Complement factor h is critical in the maintenance of retinal perfusion", 2009, Am J Pathol 175: 412-421.
Markiewski et al. "The role of complement in inflammatory diseases from behind the scenes into the spotlight", 2007, Am J Pathol 171: 715-727.
McNearney et al. "Membrane cofactor protein of complement is present on human fibroblast, epithelial, and endothelial cells", 1989, J Clin Invest 84(2): 538-545.
Montes et al. "Functional basis of protection against age-related macular degeneration conferred by a common polymorphism in complement factor B", 2009, Proc Natl Acad Sci USA 106: 4366-4371.
Mullins et al. "Structure and composition of drusen associated with glomerulonephritis: implications for the role of complement activation in drusen biogenesis", 2001, Eye (Lond) 15: 390-395.
Niculescu et al. "The Role of Complement Activation in Atherosclerosis", 2004, Immunaol Res 30: 73-80.
Nozaki et al. "Drusen complement components C3a and C5a promote choroidal neovascularization", 2006, Proc Natl Acad Sci USA 103: 2328-2333.
Orlean et al. "GPI anchoring of protein in yeast and mammalian cells, or: how we learned to stop worrying an dlove glycophospholipids", 2007, JLR 48: 993-1011.
Osuka et al. "Identification of the decay-accelerating factor CD55 as a peanut agglutinin—binding protein and its alteration in non-small cell lung cancers", 2006, Clin Cancer Res 12: 6367-6372.
Ozkiris, "Anti-VEGF agents for age-related macular degeneration", 2010, Expert Opin Ther Pat 20: 103-118.
Pickering et al. "Translational mini-review series on complement factor H: renal diseases associated with complement factor H: novel insights from humans and animals", 2008, Clin Exp Immunol 151: 210-230.
Post et al. "Structure of the gene for human complement protein decay accelerating factor", 1990, J Immunol 144: 740-744.
Qian et al. "Identification and functional characterization of a new gene encoding the mouse terminal complement inhibitor CD59", 2000, J Immunol 165: 2528-2534.
Ramo et al. "Evaluation of adenovirus-delivered human CD59 as a potential therapy for AMD in a model of human membrane attack complex formation on murine RPE", 2008, Invest Ophthalmol Vis Sci 49(9): 4126-4136.

(56) References Cited

OTHER PUBLICATIONS

Reynolds et al. "Plasma complement components and activation fragments: associations with age-related macular degeneration genotypes and phenotypes" 2009, Invest Ophthalmol Vis Sci 50: 5818-5827.

Richards et al. "Mutations in human complement regulator, membrane cofactor protein (CD46), predispose to development of familial hemolytic uremic syndrome", 2003, Proc Natl Acad Sci USA 100(22): 12966-12971.

Rohrer et al. "Eliminating complement factor D reduces photoreceptor susceptibility to light induced damage", 2007, Invest Ophthalmol Vis Sci 48: 5282-5289.

Rohrer et al. "A targeted inhibitor of the alternative complement pathway reduces angiogenesis in a mouse model of age-related macular degeneration", 2009, Invest Ophthalmol Vis Sci 50: 3056-3064.

Saint-Geniez et al. "Development and pathology of the hyaloid choroidal and retinal vasculature", 2004, Int J Dev Biol 48: 1045-1058.

Sakoda et al. "A high-titer lentiviral production system mediates efficient transduction of differentiated cells including beating cardiac myocytes", 1999, J Mol Cell Cariol 31: 2037-2047.

Samulski et al. "Helper-free stocks of recombinant adeno-associated viruses: normal integration does not require viral gene expression", 1989, J Virol 63: 3822-3828.

Satoh et al. "Humoral injury in porcine livers perfused with human whole blood", 1997, Transplantation 64(8) 1117-1123.

Sawada et al. "Comlementary DNA sequence and deduced peptide sequence for CD59/MEM-43 antigen, the human homologue of murine lymphocyte antigen Ly-6C", 1989, Nucleic Acids Res 17(16) 6728.

Skerka et al. "Defective complement control of factor H (Y402H) and FHL-1 in age-related macular degeneration", 2007, Mol Immunol 44: 3398-3406.

Suzuki et al. "Effect of sugar chain of soluble recombinant CD59 on complement inhibitory activity", 1996, FEBS Letters 399: 272-276.

Sweigard et al. "Adenovirus-mediated delivery of CD46 attenuates the alternative complement pathway on RPE: implications for age-related macular degeneration", 2011, Gene Therapy 18: 613-621.

Tenner "Complement in Alzheimer's disease: opportunities for modulating protective and pathogenic events", 2001 Neurobiol Aging 22: 849-861.

Tezel et al. "Glaucomatous tissue stress and the regulation of immune response through glial toll-like receptor signaling", 2010, Invest Ophthalmol Vis Sci 51: 5697-5707.

Thorley et al "Transgenic expression of a CD46 (membrane cofactor protein) minigene: studies of xenotransplantation and measles virus infection", 1997, Eur J Immunol 27: 726-734.

Tian et al. "Adenovirus activates complement by distinctly different mechanisms in vitro and in vivo: Indirect complement activation by virions in vivo", 2009, J Virol 83: 5648-5658.

Ucuzian et al. "Molecular mediators of angiogenesis", 2010, J Burn Care Res 31: 158-175.

Ven Den Berg et al "Rapid isolation and characterization of native mouse complement components C3 and C5", 1989, J Immunol Methods 122: 73-78.

Vedeler et al. "The expression of CD59 in normal human nervous tissue", 1994, Immunology 82(4): 542-547.

Vogt et al "Distribution of complement anaphylatoxin receptors and membrane-bound regulators in normal human retina", 2006, Eye Res 83: 834-840.

Walter et al "Electrophysiological abnormalities in age-related macular degeneration", 1999, Graefes Arch Clin Exp Ophtalmol 237: 962-968.

Wu et al. "Complement regulator CD59 protects against atherosclerosis by restricting the formation of complement membrane attack complex", 2009, Circ Res 104: 550-558.

Yannuzzi et al. "Retinal angiomatous proliferation in age-related macular degeneration", 2001, Retina 21: 416-434.

Kreppel et al. "Long-term transgene expression in the RPE after gene transfer with a high-capacity adenoviral vector", 2002, Invest Ophthalmol Vis Sci 43:1965-1970.

Maller et al. "Variation in complement factor 3 is associated with risk of age-related macular degeneration", 2007, Nat Genet 39:1200-1201.

Yates et al. "Complement C3 variant and the risk of age-related macular degeneration", 2007, N Engl J Med 357:553-561.

Zhang et al. "Early complement activation and decreased levels of glycosylphosphatidylinositol-anchored complement inhibitors in human and experimental diabetic retinopathy", 2002, Diabetes 51:3499-3504.

Yoon et al. "Characterization of a soluble form of the C3b/C4b receptor (CRI) in human plasma", 1985, J Immunol, vol. 134, No. 5, 3332-3338.

Zipfel "Hemolytic uremic syndrome: How do factor H mutants mediate endothelial damage", Trends Immunol, 2001, vol. 22 No. 7, 345-348.

* cited by examiner

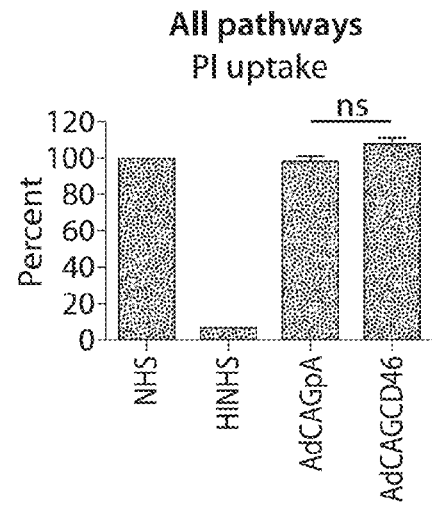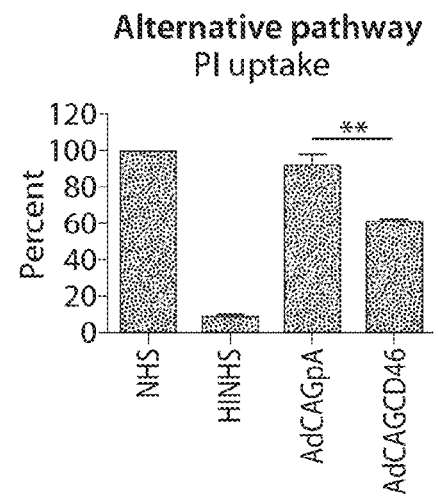
Fig. 11A    Fig. 11B
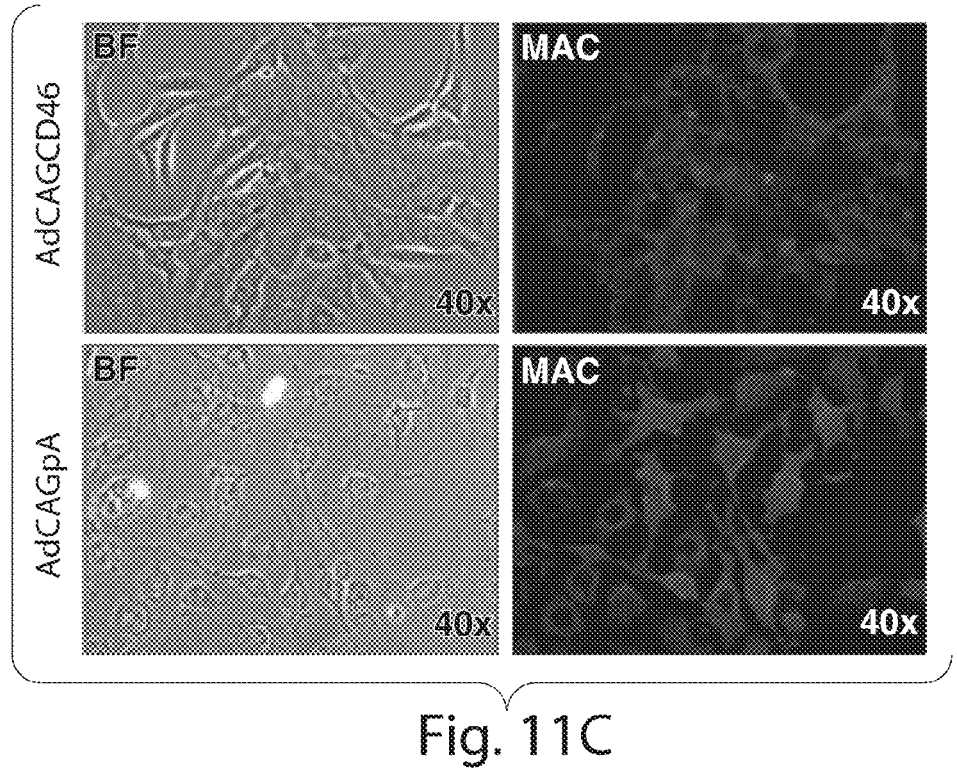
Fig. 11C

COMPOSITIONS, METHODS AND KITS FOR MODELING, DIAGNOSING, AND TREATING COMPLEMENT DISORDERS

RELATED APPLICATIONS

The present application is a continuation-in-part of U.S. utility application Ser. No. 12/867,566 filed Aug. 13, 2010, which claims the benefit of international application number PCT/US2009/000947 filed Feb. 13, 2009, which claims the benefit of U.S. provisional application Ser. Nos. 61/066,062 filed Feb. 15, 2008, 61/066,288 filed Feb. 19, 2008, and 61/070,650 filed Mar. 25, 2008 in the U.S. Patent and Trademark Office, and is a continuation of international application number PCT/US2011/045933 filed Jul. 29, 2011 which claims the benefit of U.S. provisional application Ser. Nos. 61/368,931 filed Jul. 29, 2010, 61/441,501 filed Feb. 10, 2011, 61/445,430 filed Feb. 22, 2011, and 61/480,082 filed Apr. 28, 2011, each of which is hereby incorporated herein by reference in its entirety.

GOVERNMENT SUPPORT

This invention was made with government support under grant number EY013837 awarded by the National Institutes of Health. The government has certain rights in the invention.

TECHNICAL FIELD

Systems, compositions, methods and kits are provided related to the role of complement in ocular pathology, for diagnosing a complement-based ocular disease, and for identifying potential therapeutic agents using C3 protein. Methods, composition and kits are provided for preventing or treating a complement-related condition using CD46 protein, CD55 protein, or a recombinant soluble terminator of activated complement (STAC) protein.

BACKGROUND

Activation of complement, a key component of innate immunity, results in generation of anaphylatoxins that are pleiotropic effector molecules that mediate inflammatory processes such as chemoattraction, vasodilation and vasopermeability (Markiewski et al. 2007 Am J Pathol 171: 715-727), and non-inflammatory processes such as tissue regeneration, lipid metabolism, and synapse formation (Klos et al. 2009 Mol Immunol 46: 2753-2766). Activation of complement terminates in formation of a pore on the surface of target cells referred to as the membrane attack complex (MAC), resulting in cell lysis and cell death.

Inappropriate activity of the complement system, specifically on endothelial cells, results in a number of diseases and negative conditions. Damage and detachment of the endothelium due to abnormal complement activity has been documented in atypical hemolytic uremic syndrome, aHUS (Zipfel et al. 2001 Trends Immunol 22: 345-348). Membranoproliferative glomerulonephritis (MPGN) MPGN type I and MPGN type II (dense deposit disease) are characterized by presence of complement proteins within the subendothelial dense-deposit along the glomerular basement membrane (Pickering et al. 2008 Clin Exp Immunol 151: 210-230). Dense deposit disease has been linked to a deficiency in complement regulator, Factor H (Licht et al. 2009 Thromb Haemost 101: 271-278). Transgenic mice expressing negative regulator of complement protectin (CD59) on the endothelium are protected against atherosclerosis (Wu et al. 2009 Circ Res 104: 550-558).

Age-related macular degeneration (AMD) is a disease associated with aging that gradually destroys sharp, central vision, and is the leading cause of blindness in the elderly (Klein et al. 2007 Ophthalmology 114: 253-262). The macula is a specific tissue located in the center of the retina, the light-sensitive tissue at the back of the eye that converts light or an image into electrical impulses.

AMD is classified as either wet age-related macular degeneration or dry age-related macular degeneration. Wet AMD is characterized by growth of abnormal blood vessels behind the retina under the macula. These new blood vessels are fragile and often leak blood and fluid. The blood and fluid raise the macula from its normal place at the back of the eye, causing loss of central vision. Wet AMD is treated with laser surgery, photodynamic therapy, and injections into the eye. None of these treatments, however, cures wet AMD, rather the treatments slow progression of the disease. Dry AMD is characterized by slow breakdown of light-sensitive cells in the macula, gradually blurring central vision in the affected eye. Over time, less of the macula functions and central vision is gradually lost. There is no known form of treatment for advanced stage dry AMD, and vision loss is inevitable. A specific high-dose formulation of antioxidants and zinc has been shown to prevent intermediate stage AMD from progressing to advanced AMD.

AMD has been tightly linked to polymorphisms in various complement genes (Anderson et al. 2010 Prog Retin Eye Res 29: 95-112), and complement proteins such as MAC have been observed to be deposited on choroidal endothelial cells (Anderson et al. 2002 Am J Ophthalmol 134: 411-431).

Complement proteins are deposited on the choriocapillaris of patients with diabetic retinopathy, as well as in the retinal vessels of diabetic subjects (Geri et al. 2002 Invest Ophthalmol Vis Sci 43: 1104-1108). These vessels also exhibited significant reduction in expression of the complement regulatory proteins decay accelerating factor (CD55) and CD59. Hyperacute rejection of organ transplantation, mainly the liver and kidney, has shown evidence of complement activity on the endothelium, and is considered a key reason for transplant rejection (Satoh et al. 1997 Transplantation 64: 1117-1123). An ex vivo perfusion simulation of xenotransplantation using normal human blood in porcine liver was associated with intralobular hemorrhage and complete loss of hepatic function within hours of complement component 3 and MAC deposition on endothelial cells (Pascher et al. 1996 Transplant Proc 28: 754-755).

There is a need for systems, methods and kits for assaying (i.e., prognosing or diagnosing) ocular diseases and retinal pathologies such as AMD and for identifying potential therapeutic agents. Currently, no effective methods are available for treating complement-diseases or conditions, let alone AMD. There is a need for compositions, methods and kits for preventing or treating a subject having a complement-related condition.

SUMMARY

An aspect of the invention provides a method for treating AMD in an ocular tissue of a subject, including contacting the ocular tissue of the subject with a composition comprising a CD46 protein or a CD55 protein, such that the ocular tissue is treated for AMD. In a related embodiment, the ocular tissue is treated for any complement-related disease or condition.

In related embodiments, the composition includes at least one selected from the group of: a nucleic acid vector with a gene encoding the protein; the protein; or the protein expressed directly from naked nucleic acid.

In related embodiments of any of the above methods, the vector is a viral vector or a plasmid, for example the viral vector is derived from a genetically engineered genome of at least one virus selected from the group consisting of adenovirus, adeno-associated virus, a herpesvirus, and a lentivirus. For example, the lentivirus is a retrovirus.

In various embodiments of the composition, the ocular tissue is selected from the group of: retinal pigment epithelium, retina, choroid, sclera, lens, cornea, Bruch's membrane, and an ocular blood vessel. For example the ocular blood vessel includes a choroidal blood vessel.

In various embodiments of the method, delivery of the protein or the vector is by at least one injection route selected from the group consisting of intravenous, intra-ocular, intramuscular, subcutaneous, and intraperitoneal. In an embodiment of the method, the macular degeneration is dry AMD. Alternatively, the macular degeneration is wet AMD.

In an embodiment of the method, the CD46 protein includes an amino acid sequence as shown in SEQ ID NO: 4 or a portion or homologue thereof. In related embodiments, the CD46 protein includes an amino acid sequence at least about 50%, about 55%, about 60%, about 65%, about 70%, about 75%, about 80%, about 85%, about 90%, about 95%, or about 99% identical to SEQ ID NO: 4. In an embodiment of the method, the nucleic acid with a gene encoding the CD46 protein includes an nucleotide sequence as shown in SEQ ID NO: 3 or a portion or homologue thereof. In related embodiments, the CD46 nucleotide sequence is at least about 50%, about 55%, about 60%, about 65%, about 70%, about 75%, about 80%, about 85%, about 90%, about 95%, or about 99% identical to SEQ ID NO: 3.

In an embodiment of the method, the CD55 protein includes an amino acid sequence as shown in SEQ ID NO: 6 or a portion or homologue thereof. In related embodiments, the CD55 protein includes an amino acid sequence at least about 50%, about 55%, about 60%, about 65%, about 70%, about 75%, about 80%, about 85%, about 90%, about 95%, or about 99% identical to SEQ ID NO: 6. In an embodiment of the method, the nucleic acid with a gene encoding the CD55 protein includes an nucleotide sequence as shown in SEQ ID NO: 5 or a portion or homologue thereof. In related embodiments, the CD55 protein includes the nucleotide sequence having at least about 50%, about 55%, about 60%, about 65%, about 70%, about 75%, about 80%, about 85%, about 90%, about 95%, or about 99% identity to SEQ ID NO: 5.

In various embodiments, the CD46 protein or the CD55 protein is non-membrane bound, for example the protein lacks or has a non-fuctional (mutated) hydrophobic transmembrane spanning domain or a glycosyl phosphatidyl inositol anchoring domain. In a related embodiment the CD46 protein or the CD55 protein is derived from a mammal, for example the CD46 protein or the CD55 protein is derived from a human, a mouse, a cow, and a sheep.

An aspect of the invention provides a pharmaceutical composition for treating a complement-related condition in a subject including a chimeric soluble terminator of activated complement (STAC) protein having amino acid sequences from at least two of a CD46 protein, a CD55 protein, and a CD59 protein, or a nucleic acid expressing or encoding the recombinant STAC protein, such that the STAC protein negatively modulates classical and alternative complement pathways. In a related embodiment, the subject is a mammal for example a human, a dog, a cat, a cow, a pig, and a horse.

In related embodiments of the composition, the STAC protein comprises two component proteins selected from the group of: the CD46 protein and the CD55 protein, the CD46 protein and the CD59 protein, and the CD55 protein and the CD59 protein. Alternatively, the composition comprises the STAC protein including each of the CD46 protein, the CD55 protein, and the CD59 protein.

A related embodiment provides the STAC protein having amino acid sequence as shown in SEQ ID NO: 1 or a portion or homologue thereof. In related embodiments, the STAC protein includes an amino acid sequence at least about 50%, about 55%, about 60%, about 65%, about 70%, about 75%, about 80%, about 85%, about 90%, about 95%, or about 99% identical to SEQ ID NO: 1.

An alternative embodiment provides the nucleic acid encoding an amino acid sequence of the CD59 protein having at least one mutation conferring loss of function of a glycosyl phosphatidyl inositol (GPI) anchoring domain, the mutation including at least one of a substitution, deletion, and addition.

A related embodiment provides the composition formulated in a dose effective to treat the subject for the complement-related condition.

A related embodiment provides the CD59 protein having an amino acid sequence that includes at least one of a secretory signal peptide and a short consensus repeat (SCR) domain.

The composition in various embodiments further includes a linker connecting amino acid sequences of the CD59 protein and the CD46 protein. In a related embodiment, the composition further includes a linker connecting amino acid sequences of the CD46 protein and the CD55 protein. In a related embodiment the composition further includes a linker connecting amino acid sequences of the CD55 protein and the CD59 protein. For example, the linker includes at least one amino acid, for example glycine. In a related embodiment, the amino acid includes at least one of: aspartate, threonine, alanine, tyrosine, serine, or proline.

The linker in various embodiments covalently connects each binding region of the STAC protein. For example, the linker is a single amino acid or a plurality of amino acids that does not reduce the stability, orientation, binding, neutralization, and/or clearance characteristics of the STAC protein.

A related embodiment provides the amino acid sequences of the CD46, CD55 and CD59 proteins are encoded by nucleic acid as a protein fusion in the same reading frame as a transcription fusion in which expression of the protein is operably linked and expressed.

A related embodiment provides the CD46 protein having an amino acid sequence that includes at least one of: a short consensus repeat domain and a serine/threonine/proline (STP) rich domain. In a related embodiment, the nucleic acid encoding the CD46 protein amino acid sequence includes at least one mutation, for example a substitution, a deletion or an addition.

The nucleic acid encoding CD55 protein amino acid sequence in a related embodiment includes at least one mutation resulting in loss of function of a glycosyl phosphatidyl inositol (GPI) anchoring domain of the CD55 protein, the mutation including for example a substitution, a deletion, or an addition. In a related embodiment, the CD55 protein amino acid sequence includes at least one of: a short consensus repeat domain and a serine/threonine/proline rich domain.

A related embodiment provides the nucleotide sequence encoding the STAC protein as a plasmid. Alternatively, the nucleotide sequence is provided as a viral vector. In a related embodiment, the vector encodes amino acid sequence SEQ ID NO: 1 or a portion thereof, for example at least about 50%, about 55%, about 60%, about 65%, about 70%, about 75%, about 80%, about 85%, about 90%, about 95%, or about 99% of SEQ ID NO: 1. In a related embodiment, the vector is at least one selected from the group of: an adenovirus, an adeno-associated virus, a herpesvirus, a poxvirus, and a lentivirus. In related embodiments, the composition is formulated to include a dose of the vector selected from: about $10^6$ to about $10^7$; $10^7$ to about $10^8$; about $10^8$ to about $10^9$; about $10^9$ to about $10^{10}$; and about $10^{10}$ to about $10^{11}$.

The nucleotide sequence in various embodiments includes that the promoter is from a gene selected from: a beta-actin for example a chicken beta actin, a peripherin/RDS, cGMP phosphodiesterase, and a rhodopsin.

The nucleotide sequence in related embodiments further encodes a linker including at least one amino acid for example a glycine, a serine, or an alanine. In a related embodiment, the linker is located between the CD59 protein and the CD46 protein amino acid sequences. In a related embodiment, the linker is located between the CD46 protein and the CD55 protein amino acid sequences. The linker in certain embodiments includes a molecule that joins two other amino acids, proteins, or domains either covalently or noncovalently, e.g., through ionic or hydrogen bonds or van der Waals interactions. It is envisioned that the CD46, CD55, and CD59 amino acid sequences can be arranged in any order without limitation, and that linkers are located between adjacent amino acid sequences.

In alternative embodiments, the composition further includes a delivery vehicle engineered to target a cell or tissue selected from the group of: a liposome, a lipid, a polycation, a peptide, a nanoparticle, a gold particle, and a polymer.

The composition in related embodiments further includes at least one of a pharmaceutically acceptable salt and a pharmaceutically acceptable emollient. In related embodiments, the composition further includes at least one agent selected from: anti-tumor, anti-coagulant, anti-viral, antibacterial, anti-mycobacterial, anti-fungal, anti-proliferative and anti-apoptotic.

An aspect of the invention provides a method of treating a complement-related condition in a subject including: contacting a cell of the subject with a composition including a vector carrying a nucleotide sequence encoding a recombinant chimeric soluble terminator of activated complement (STAC) protein operably linked to a promoter sequence causing expression of the STAC protein in a cell, such that the nucleotide sequence encodes amino acid sequences of each of a CD59 protein, a CD46 protein, and a CD55 protein; and, observing a decrease in a symptom of the complement-related condition in the subject in comparison to prior to contacting, thereby treating the complement-related condition.

The method in a related embodiment further includes observing as measuring an amount of a protein of a complement pathway. For example, the protein is MAC and measuring includes identifying or determining MAC deposition on a cell or in the subject. In a related embodiment, determining extent of MAC deposition is analyzing by immunohistochemistry with antibodies that are specific for mammalian MAC for example human MAC.

In related embodiments, the cell is selected from: muscular, epithelial, endothelial, and vascular. For example, the cell is selected from a tissue, for example the tissue is in at least one of: eye, heart, kidney, thyroid, brain, stomach, lung, liver, pancreas, and vascular system.

The condition in related embodiments is selected from the group of: macular degeneration, age-related macular degeneration, inflammatory bowel disease, thyroiditis, cryoglobulinaemia, foetal loss, organ graft rejection, sepsis, viral infection, fungal infection, bacterial infection, toxic shock syndrome (TSS), membranoproliferative glomerulonephritis, dense deposit disease, peroximal nocturnal hemoglobinurea, lupus nephritis, membranous nephritis, immunoglobulin A nephropathy, goodpasture syndrome, post-streptococcal glomerulonephritis, systemic lupus erythematosus, atypical hemolytic uremic syndrome, systemic lupus erythromatosis, lupus arthritis, rheumatoid arthritis, Sjögren's syndrome, Behçet's syndrome, systemic sclerosis, Alzheimer's disease, multiple sclerosis, myasthenia gravis, Guillain-Barré syndrome, cerebral lupus, stroke, adult respiratory distress syndrome, chronic obstructive pulmonary disease, cystic fibrosis, haemolytic anaemia, paroxysmal cold haemoglobinuria, paroxysmal nocturnal haemoglobinuria, vasculitis, pemphigus, bullous pemphigoid, phototoxic reactions, psoriasis, anaphylactic shock, allergy, asthma, myocardial infarction, and atherosclerosis.

Alternative embodiments of the method include contacting the cell in vitro, or contacting the cell ex vivo, in vivo or in situ.

Prior to contacting the cell, the method in a related embodiment further includes engineering the vector carrying the nucleotide encoding the recombinant STAC protein, such that the STAC protein is a chimeric protein. In a related embodiment, engineering includes mutating nucleic acid encoding the CD55 protein amino acid sequence such that at least one mutation results in loss of function of glycosyl phosphatidyl inositol (GPI) anchoring domain.

The engineering step includes in a related embodiment mutating nucleic acid encoding the CD46 protein amino acid sequence such that at least one mutation results in removal of a secretory signal. In a related embodiment, engineering includes mutating nucleic acid sequence encoding CD55 protein amino acid sequence such that at least one mutation results in loss of function of GPI anchoring domain. The mutation includes for example at least one of: a substitution, a deletion, and an addition. In a related embodiment, engineering includes recombinantly joining nucleic acid encoding the CD59 protein C-terminus with nucleic acid encoding amino acids of CD46 protein N-terminus. In a related embodiment, engineering includes recombinantly joining nucleic acid sequence encoding the CD46 protein C-terminus with nucleic acid encoding the CD55 protein N-terminus.

The STAC protein further in various embodiments includes a purification tag and/or a protease cleavage site for removal of the tag. In various embodiments, the purification tag is at least one selected from: Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin.

The subject is in various embodiments a mammal, for example a human, a research animal, a high value zoo animal, and an agricultural animal.

The method includes in various embodiments contacting the cell by administering the composition by at least one route selected from: parenteral, intravenous, intramuscular, intraperitoneal, intradermal, intraci sternal, mucosal, subcutaneous, sublingual, intranasal, oral, ocular, bucal, intra-ocular, intravitreal, topical, transdermal, vaginal, rectal, and infusion.

The method includes in related embodiments observing by analyzing amount or presence of at least one of: an antibody, a peptide, a carbohydrate, an enzyme, a sugar, and a surface receptor. For example, observing includes analyzing an amount of membrane attack complex (MAC).

An aspect of the invention provides, a kit for regulating or of treating a complement-related condition in a subject, the method including: a composition including a chimeric soluble terminator of activated complement (STAC) recombinant protein including amino acid sequences from each of a CD46 protein, a CD55 protein, and a CD59 protein, or a nucleotide sequence encoding the recombinant STAC protein, such that the composition negatively modulates classical and alternative complement pathways and is formulated in a dose effective to treat the subject for the complement-related condition; instructions for treating the subject; and, a container.

The STAC protein in various embodiments of the kit has an amino acid sequence as shown in SEQ ID NO: 1 or a portion thereof. In related embodiments, the STAC protein amino acid sequence is at least about 70%, about 75%, about 80%, about 85%, about 90%, about 95%, or about 99% identical to SEQ ID NO: 1.

The nucleotide sequence in related embodiments of the kit includes a vector or a plasmid. The vector is in various embodiments an engineered viral vector selected from: an adenovirus, an adeno-associated virus, a herpesvirus, a poxvirus, and a lentivirus.

The STAC protein in various embodiments of the kit is a genetic fusion of the CD46, CD55 and CD59 protein amino acid sequences. In related embodiments, the composition includes any of the pharmaceutical compositions described herein.

The kit further includes in various embodiments a therapeutic agent. For example, the therapeutic agent is selected from: anti-coagulant, anti-tumor, anti-viral, anti-bacterial, anti-mycobacterial, anti-fungal, anti-proliferative, and anti-apoptotic.

An aspect of the invention provides, a pharmaceutical composition for treating a complement-related condition in a subject including: an adenovirus viral vector including a nucleotide sequence encoding a recombinant chimeric soluble terminator of activated complement (STAC) protein including: an amino acid sequence as shown in SEQ ID NO: 1 or portion thereof, such that the composition negatively modulates classical and alternative complement pathways and is formulated in a dose effective to treat the subject for the complement-related condition.

An aspect of the invention provides a method of assaying extent of human macular degeneration (MD) in a model cell system or a method in a model cell system of assaying a serum complement component for prognosis or diagnosis of MD, the method including: exposing a first sample of cells to serum and measuring resulting lysis, and comparing extent of lysis to that in a second sample of control cells not so exposed to serum, such that the extent of lysis in the first sample compared to that in the second sample is a measure of complement-induced MD.

An aspect of the invention provides a method of assaying in a model cell system potential therapeutic agents for human MD, the method including: contacting a first sample of cells to serum and measuring resulting lysis, and contacting a second sample of otherwise identical control cells with serum and a source of mammalian CD46 protein or mammalian CD55 protein and measuring resulting lysis; and contacting at least a third sample of cells to a candidate therapeutic composition and otherwise identically to serum, such that the extent of lysis of the third sample compared to that in the first and second sample is a measure of protection by the candidate composition, thereby providing the method of assaying for potential therapeutic agents. In a related embodiment, the mammalian protein is a human protein.

A related embodiment of the above methods further includes contacting cells or tissues with a recombinant vector having a gene capable of expressing the protein such as the CD46 protein or CD55 protein. Lysis is measured for example by propidium iodide uptake and cell sorting. In a related embodiment of the above methods, the cells are hepatocytes. In related embodiments the cells are of murine origin. In a related embodiment of the above methods, the source of the protein is human. In a related embodiment of the above methods the serum is normal human serum. Alternatively, the serum is from a diseased subject, for example, the diseased subject has MD.

An aspect of the invention provides a method of diagnosing or prognosing presence or progression of macular degeneration, the method including determining extent of MAC deposition on retina. In a related embodiment of the method, determining extent of MAC deposition is analyzing by immunohistochemistry with antibodies that are specific for human MAC.

An aspect of the invention provides a pharmaceutical composition for treating macular degeneration including CD46 protein or CD55 protein or a source of expression of CD46 protein or CD55 protein in vivo, in which the composition is formulated for ocular delivery, in a dose effective to treat macular degeneration.

In various related embodiments of the composition, the protein or source of expression of protein is at least one selected from the group consisting of: a nucleic acid vector with a gene encoding the protein; a viral vector with a gene encoding the protein; and the protein. In related embodiments, the gene includes a nucleotide sequence selected from SEQ ID NO: 3 or SEQ ID NO: 5.

In related embodiments the composition includes at least one selected from the group of: a nucleic acid vector with a gene encoding the protein; the protein; or protein expressed directly from naked nucleic acid. For example, the composition includes a nucleic acid vector with a gene encoding CD55 protein; CD55 protein; or CD55 expressed directly from naked nucleic acid. In a related embodiment of the composition, the CD55 protein includes an amino acid sequence shown in SEQ ID NO: 6 or a portion or homologue thereof. Alternatively, the composition includes a CD46 protein; a nucleic acid vector with a gene encoding CD46 protein; or CD46 expressed directly from naked nucleic acid. In a related embodiment of the composition, the CD46 protein includes an amino acid sequence shown in SEQ ID NO: 4 or a portion or homologue thereof.

In related embodiments of the composition, the composition formulated for ocular delivery is at least one selected from the group consisting of: injection, eye drop, and ointment. In a related embodiment of the composition, injection is at least one selected from the group consisting of: intraocular injection, subconjunctival injection, and subtenon injection. In a related embodiment, the composition further includes at least one drug selected from the group consisting of: anti-tumor, antiviral, antibacterial, anti-mycobacterial, anti-fungal, anti-proliferative and anti-apoptotic. In a related embodiment, the protein is expressed as a soluble protein. In a related embodiment, the protein has a deletion encoding a GPI anchoring domain. For example, the CD55 protein has a deleted GPI anchoring domain and thus is membrane independent.

An aspect of the invention provides a kit for assaying MAC deposition on ocular tissue or cells and for screening agents that inhibit deposition, the kit includes anti-MAC antibody, a container, and instructions for use with normal human serum and the ocular tissue or cells. In a related embodiment, the kit further includes anti-emmprin antibody and/or normal human serum. In another related embodiment, the kit further includes at least one of CD46 protein, CD55 protein, and STAC protein as a positive control and the protein is a soluble form or a membrane-bound form, the latter for example embedded in a liposome preparation. In other related embodiments of the kit, at least one of the antibody, the serum, and the protein is a lyophil.

An aspect of the invention provides a method in a model cell system of assaying a serum complement component for prognosis or diagnosis of MD, the method including: contacting detectably labeled cells with serum from a subject and measuring amount of extracellular and/or intracellular detectable agent for contacted cells; and comparing extracellular and/or intracellular agent in the cells to that in detectably labeled control cells not exposed to the serum and otherwise identical, such that amount of extracellular and/or intracellular agent in the contacted cells is compared to that in the control cells, such that a greater amount of extracellular detectably labeled agent in cells contacted with serum compared to the control cells is an indication of prognosis or diagnosis of MD.

An aspect of the invention provides a method of assaying in a model cell system a potential therapeutic agent for efficacy in treatment of human MD, the method including: contacting a first sample of detectably labeled cells with serum from a subject and measuring amount of extracellular and/or intracellular detectable agent, and contacting a second sample of otherwise identical detectably labeled control cells with serum and a source of human CD46 protein or human CD55 protein and measuring amount of extracellular and/or intracellular detectable agent; and contacting at least a third sample of detectably labeled cells to at least one candidate therapeutic composition and otherwise identically to serum and measuring amount of extracellular and/or intracellular detectable agent, such that the amount of extracellular and/or intracellular detectable agent of the third sample compared to that in the first sample and the second sample is a measure of protection by the candidate composition, such that a greater amount of extracellular detectably labeled agent is an indication of MD, thereby assaying for a potential therapeutic agent for efficacy in treatment of human MD.

In various embodiments of the above methods, the detectable agent is at least one composition selected from the group consisting of a recombinant vector having a gene capable of expressing a detectable protein, a fluorescent agent, a colorimetric agent, an enzymatic agent, and a radioactive agent. For example, the detectable protein is at least one fluorescent protein selected from the group consisting: green fluorescent protein, aequorin, cyan fluorescent protein, DsRed fluorescent protein, enhanced green fluorescent protein, and yellow fluorescent protein. In other embodiments, the detectable agent is not a protein, for example, the detectable agent is at least one fluorescent agent selected from the group consisting of: Indocyanine Green, Doxorubicin, Riboflavin, Chlorophyll, and Porphyrin. In other embodiments, the detectable protein is enzyme, for example, β-galactosidase or alkaline phosphatase.

In embodiments of the above methods, the cells are hepatocytes; exemplary cells are of murine origin. In embodiments of the above methods, the source of protein (i.e., the CD46 protein or the CD55 protein) is human. In certain embodiments of the above methods, the serum is normal human serum. Alternatively, the serum is from a diseased subject. In general, the subject is in need of diagnosis or prognosis of MD. In other embodiments, the human CD46 or human CD55 protein is soluble. In other embodiments the human CD46 or human CD55 protein is membrane-bound.

An aspect of the invention herein provides a model system for diagnosing or prognosing a complement-based ocular pathology or for screening potential therapeutic agents to treat the pathology, the model system including: a first sample of cells or tissue contacted with a vector including a nucleic acid encoding complement component 3 (C3) to overactivate natural complement takeover in the cells or the tissue; a second sample of cells or tissue contacted with a control nucleic acid encoding a detectable protein, such that the vector and the control vector include the same promoter sequence operably linked to nucleic acids encoding the C3 and the detectable protein, such that the detectable protein is a control that does not overactivate the natural complement takeover, such that the second sample of the cells or tissue are otherwise identical to the first sample of the cells or tissue contacted with the vector; a control sample of cells or a tissue from a normal subject, such that the normal subject is not affected by the complement-based ocular pathology; and a marker associated with complement activation for measuring in each of the first sample, the second sample and the control sample, such that the marker is characteristic of the ocular pathology, such that an amount of the marker in the third sample compared to amounts in the first sample and the second sample is a measure of prognosis or diagnosis of the complement-based ocular disease or the ocular pathology.

In a related embodiment the nucleic acid includes a nucleotide sequence shown in SEQ ID NO: 7. For example the nucleotide sequence is obtained from a mammal such as a human or mouse. In a related embodiment, the C3 includes an amino acid sequence including SEQ ID NO: 8. In related embodiments, the amino acid sequences includes at least about 30% identity, or at least 40%, 50%, 60%, 70%, 75%, 80%, 85%, 90%, 95%, 96%, 98%, or 99% identity.

In related embodiments of the system, the vector includes a viral vector, for example an adenovirus, an adeno-associated virus, a retrovirus, a herpesvirus, and a lentivirus. In related embodiments, the vector includes a plasmid vector.

In related embodiments of the system, the detectable protein is at least one selected from: a fluorescent protein, an enzyme having a colorimetric assay, and a chemifluorescent protein, for example the fluorescent protein is at least one selected from the group consisting: green fluorescent protein, enhanced green fluorescent protein, aequorin, cyan fluorescent protein, DsRed fluorescent protein, and yellow fluorescent protein.

In related embodiments of the system, the marker includes at least one selected from: a membrane attack complex protein, glial fibrillary acidic protein, vascular endothelial growth factor, and *Griffonia simplicifolia* lectin I. In related embodiments of the system, the marker is a complement component or complement protein such as an anaphylatoxin, such as C3a or C5a.

In related embodiments, prior to contacting, the cells or the tissues are cultured in vitro. In related embodiments, the cells or tissue are contacted in an animal model in vivo. For example the animal model is a mouse model. In related embodiments, the cells or the tissue includes ocular cells or ocular tissues, respectively.

In related embodiments, the cells or tissue are contacted by injection, for example by at least one route of administration selected from: intra-ocular, invitreal, subconjunctival, subretinal, and subtenon. In various embodiments, the cells or tissue are contacted topically.

In related embodiments, the marker includes at least one selected from the group of: a membrane attack complex protein, glial fibrillary acidic protein, vascular endothelial growth factor, and *Griffonia simplicifolia* lectin I. In related embodiments, measuring includes observing cellular staining or tissue staining, for example staining of a cellular membrane or nucleus.

In related embodiments of the system, measuring includes observing at least one from the group of: increased vascular permeability, increased endothelial cell proliferation and migration, RPE atrophy, loss of photoreceptor outer segments, reactive gliosis, increased drusen formation, Muller cell activation, formation of membrane attack complex, retinal detachment, and reduced retinal function. For example, the first sample of the cells or the tissue is characterized as having loss of integrity of retinal vessels.

An aspect of the invention herein provides a method for diagnosing a complement-based ocular disease in cells or tissue from a subject, the method including: contacting a first sample of the cells or tissue from the subject with a vector including a nucleic acid encoding complement component 3 (C3), such that the C3 overactivates natural complement takeover in the cells or the tissue; measuring an amount of a marker in the first sample, such that the marker is characteristic of the disease; and comparing amounts of the marker in the first sample to amount of the marker in a second sample of cells or tissue from the subject not so contacted to the vector and otherwise identical, such that amount of the marker in the first sample of cells is compared to that in the cells or the tissue from the subject, such that a substantially similar amount or even greater amount of the marker in the second sample compared to the amount of the marker in first sample is an indication of the diagnosis of the complement-based ocular disease in the subject. In related embodiments of the method, the cells or the tissue includes ocular cells or ocular tissues, respectively.

In related embodiments, the method further includes obtaining a control sample of cells or tissue from a normal subject, such that the normal subject is not affected by the complement-based ocular disease, and measuring an amount of the marker in the control sample, such that a greater amount of the marker in the second sample and/or first sample compared to the amount of the marker in the control sample is an indication of presence of the complement-based ocular disease in the subject. For example, the method indicates the presence of age-related macular degeneration.

An aspect of the invention herein provides a method of identifying in a model system a potential therapeutic agent for treating or preventing a complement based-ocular disease, the method including: contacting a first sample of cells or tissue with a vector including a nucleic acid encoding complement component 3 (C3) to overactivate natural complement takeover in the cells or the tissue, contacting a second sample of the cells or tissue with a control nucleic acid encoding a detectable protein, such that the vector and the control vector include the same promoter sequence operably linked to nucleic acids encoding the C3 and the detectable protein, such that the detectable protein is a control that does not overactivate the natural complement takeover, and contacting at least a third sample of cells or tissue with the nucleic acid encoding the C3 and at least one of a plurality of potential therapeutic agents; and measuring in the first sample, the second sample and the third sample, an amount of the marker, such that the marker is characteristic of the disease, such that the amount of the marker in the third sample compared to that in the first sample and/or the second sample is a measure of treatment and protection by the potential therapeutic agent, such that a decreased amount of the marker in the third sample compared to the first sample is an indication that the agent is therapeutic, thereby identifying the potential therapeutic agent for treating or preventing the complement-based-ocular disease.

In related embodiments of the method, the complement based-eye disease includes AMD condition, for example wet AMD or dry AMD.

In related embodiments of the method, the detectable protein is at least one selected from: a fluorescent protein, an enzyme having a colorimetric assay, and a chemifluorescent protein. In related embodiments, the fluorescent protein is at least one selected from the group of: green fluorescent protein, enhanced green fluorescent protein, aequorin, cyan fluorescent protein, DsRed fluorescent protein, and yellow fluorescent protein.

In related embodiments, the promoter includes a cytomegalovirus (CMV) promoter, for example a human CMV promoter or mouse CMV promoter. In related embodiments, the vector includes a viral vector, for example the viral vector is an adenovirus, an adeno-associated virus, a retrovirus, a herpesvirus, or a lentivirus.

In related embodiments of the method, the marker includes a protein, an enzyme, a lipid, a carbohydrate, or a nucleic acid. In related embodiments, the vector is selected from the viral vector encoding a DNA or an RNA, a naked DNA vector, and a microencapsulated DNA or RNA.

In related embodiments, the marker includes at least one selected from the group of: MAC or a MAC protein, glial fibrillary acidic protein, vascular endothelial growth factor, and *Griffonia simplicifolia* lectin I.

In related embodiments, measuring further includes observing a localization of the marker in the cells or the tissue contacted by at least one of the first sample, the second sample, and the third sample. For example, the method includes observing the localization of the marker within the cytoplasm or in a nucleus.

In related embodiments of the method, prior to contacting, the cells or the tissues are cultured in vitro. For example the cells or tissue are cultured in a tube, a flask, or a plate.

In related embodiments of the method, contacting is in an animal model in vivo. In related embodiments of the method, contacting includes injecting the cells or the tissue, for example by at least one route of administration selected from: intra-ocular, invitreal, subconjunctival, subretinal, and subtenon. In related embodiments of the method, contacting includes administering topically, for example to an ocular tissue or mucosal lining.

In related embodiments of the method, prior to contacting, the method includes engineering the vector having the nucleic acid encoding the C3 to express the C3 as a soluble protein.

In related embodiments, measuring further includes observing cellular staining or tissue staining, for example staining of a cellular membrane or nucleus. For example, measuring further includes observing the marker specifically located on the cells or the tissue, for example retinal pigment epithelium or retina.

In related embodiments, measuring further includes observing cellular morphology, cell viability, or tissue functionality in the samples. For example, the method includes observing decreased ocular functionality (e.g., retinal functionality) in the first sample compared to the second sample and/or third samples.

In related embodiment of the method, measuring further includes observing in the samples at least one selected from the group consisting of: retinal detachment, cellular pathology, and tissue pathology. In related embodiment of the method, measuring further includes performing electroretinography.

An aspect of the invention herein provides a kit for diagnosing or prognosing an ocular pathology and/or identifying a potential therapeutic agent for treating or preventing a complement based-ocular disease including: a vector including a nucleic acid encoding a component 3 (C3) that overactivates natural complement takeover in cells or tissue; a container; and, instructions for use. For example the instructions for use include methods described herein for identifying the potential therapeutic agent or for diagnosing or prognosing an ocular pathology.

In related embodiments, the kit further includes an anti-C3 antibody or an anti-MAC antibody. In related embodiments, the kit further includes a control vector including a control nucleic acid encoding a detectable protein absent the C3, such that the vector and the control vector include the same promoter sequence operably linked to nucleic acids encoding the C3 and the detectable protein, such that the detectable protein does not overactivate the natural complement takeover in the cells or the tissue. In related embodiments, the instructions for use in kits herein include any of the methods described herein. In various embodiments, the vector is at least one selected from: an adenovirus, an adeno-associated virus, a retrovirus, a herpesvirus, and a lentivirus. In a related embodiment, the kit further includes a plurality of cells and/or a culture medium.

An aspect of the invention provides a kit for diagnosing a complement based-ocular disease in a subject including: a vector including a nucleic acid encoding a component 3 (C3) to overactivate natural complement takeover in cells or tissue, for example the vector is a viral vector; a container; and, instructions for use.

In related embodiments, the kit further includes a control nucleic acid encoding a detectable protein, such that the vector and the control vector include the same promoter sequence operably linked to nucleic acids encoding the C3 and the detectable protein, such that the detectable protein does not overactivate the natural complement takeover in the cells or the tissue. In various embodiments, the kit further includes control cells or tissue from a normal subject that is not infected by any complement-based ocular disease. The kit further includes in a related embodiment a culture medium. In various embodiments, the instructions for use include any of methods, compositions, and kits described herein.

BRIEF DESCRIPTION OF THE DRAWINGS

FIG. 1 panel A is a set of photomicrographs showing immunostaining of human embryonic retinoblasts contacted with recombinant adenovirus a gene encoding C3 (AdemvC3; left graphs), or green fluorescent protein, GFP (AdcmvGFP; right graphs). Immunohistochemical analysis was performed with anti-mouse GFP antibody or anti-mouse C3 antibody, followed by an appropriate Cy3 conjugated secondary antibody. GFP staining was observed in the nucleus and cytoplasm of AdemvGFP-infected cells (GFP filter), and C3 staining was observed primarily in the cytoplasm of AdcmvC3-infected cells (CY3 filter). Bright field increased magnifications of the highlighted portions of the photomicrographs are shown in the insets. Unless otherwise indicated, magnification of photomicrographs is indicated at the bottom of each photomicrograph by the number preceding the X. For example, FIG. 1 panel A magnification is 10× (top row) and 40× (bottom row).

FIG. 1 panel B is a set of photographs of Western blots of lysates and media of human embryonic retinoblasts contacted with AdcmvC3 or AdcmvGFP, or control retinoblasts that were not injected with adenovirus, and analyzed under non-reducing (left) or reducing (right) conditions using a monoclonal antibody specific for binding to human C3 protein. Data show correct processing of C3 intracellularly and efficient secretion into the media for retinoblasts contacted with AdcmvC3. Under non-reducing conditions, the disulfide-linked α and β chains of C3 are observed in the media and lysates of AdcmvC3-contacted cells. Under reducing conditions, the α chain and β chain of C3 in the media migrate separately. AdcmvC3-contacted cells showed dark bands at the predicted molecular weights, 107 kDa and 62 kDa, of α chain and β chains of C3. Unfd, uninfected; NHS, Normal Human Serum.

FIG. 3 panel A is a set of photomicrographs for eyes injected with AdcmvGFP and then visualized for GFP fluorescence (left) and stained with DAPI (right). GFP fluorescence for AdcmvGFP-contacted eyes was observed in the RPE.

FIG. 3 panel B is a set of photomicrographs showing intense FITC-GSL I staining, particularly in an area of retinal detachment, in AdcmvC3-contacted retinas (left) compared with the control AdcmvGFP-contacted retinas (right). Representative images from two independent injections for each virus are shown (top row and bottom row respectively). GSL I staining was observed in the choroid indicated on the photomicrographs as an asterisk (*) in each of the AdcmvGFP-contacted eyes. GSL I staining was also observed in retinas of particular AdcmvGFP-contacted subjects specifically in areas of retinas close to the site of injection (<). However, the GSL I staining observed for retinas of AdcmvGFP-contacted eyes was much reduced compared to staining observed for retinas of AdcmvC3-contacted eyes. Both AdcmvC3-contacted retinas and AdcmvGFP-contacted retinas were stained across the region of injection, including the area of GFP-positive RPE cells. The AdcmvGFP sections shown for FITC-GSL I staining did not contain GFP-positive RPE cells, and were representative of GSL I staining across the region of injection.

FIG. 3 panel C is a set of photomicrographs at 10× magnification showing that injection of eyes with AdcmvGFP or AdcmVC3 resulted in strong GSL I staining at the RPE/retinal junction and throughout the retina in AdcmvC3-contacted eyes. GSL I binding was observed mostly in the choroid within the region of injection in AdcmvGFP-contacted eyes.

FIG. 4 panel A shows photomicrographs showing disruption to the RPE/choroid of AdcmvC3-injected eyes (top row) and no disruption to the RPE/choroid of AdcmvGFP-injected eyes (bottom row). Data show that cells in the RPE/choroid of AdcmvC3-injected eyes stained positive for GSL I. In a number of eyes (2/6) examined, it was observed that pigmented cells migrated into the retina (see inset). In AdcmvGFP-injected eyes the GSL I staining was observed to be restricted primarily to the choroid, and the RPE cell layer remaining intact. Photomicrograph magnification was 20×.

FIG. 4 panel B is a set of magnified (40×) photomicrographs showing AdcmvC3-contacted retinas visualized with BF (left) and stained with GSL I (right). The AdemvC3-contacted retinas showed a dramatic loss of RPE cells and pigment along the RPE/choroid region.

FIG. 5 panel A is a set of photomicrographs of FITC-GSL I stained eyes subretinally injected with either AdcmvC3 (left) or AdcmvGFP (right). Increased staining was observed at the site of injection (<) for eyes injected with either AdcmvC3 or AdcmvGFP. Staining in AdcmvC3-injected eyes extended beyond the region of injection. Discontinuous (dashed) lines delineate the border of the eyecups.

FIG. 5 panel B is a bar graph showing quantitation of area ($mm^2$) of GSL I staining in eyecups on the ordinate as a function of the adenovirus subretinal injection (abscissa). Murine subjects were injected with either AdemvC3 or AdemvGFP. Data show a significantly greater area of staining in eyecups of AdcmvC3-contacted eyes compared to eyecups of AdemvGFP-contacted eyes (*$p<0.05$). AdcmvC3 (n=13), AdcmvGFP (n=6).

FIG. 5 panel C is a bar graph showing quantitation of retinal detachment ($\mu M$) in eyecups on the ordinate as a function of each of the adenovirus vectors injected into the eyes, AdcmvC3 or control AdcmvGFP (abscissa). Retinal detachment was significantly increased (2.6-fold) in AdcmvC3-injected eyes compared to AdemvGFP-injected (*$p<0.05$). AdcmvC3 (n=5), AdcmvGFP (n=4).

FIG. 5 panel D is a set of photomicrographs of eyes injected with 0.25% sodium hyaluronate (SH) and illuminated with bright field (top row) and stained with GSL I (bottom row). Data show GSL I staining confined to endothelial cells of the inner nuclear layer, with a few pigmented cells at the RPE/retinal interface (<) staining GSL I-positive (n=3).

FIG. 5 panel E is a photograph, 40× objective magnification, of the RPE/choroid of a representative eye injected with 0.25% SH. Data show an intact RPE cell layer. BF, bright-field; C, choroid; R, RPE; O/I, outer/inner nuclear layer.

FIG. 6 panel. A is a set of photomicrographs of retinas contacted by injection with either AdcmvC3 (top row) or control AdcmvGFP (bottom row) and illuminated with bright field (first column) and stained with DAPI (second and third columns). DAPI staining of AdcmvC3-contacted retinas showed perturbations in the photoreceptor cell layer, with little or no disturbance to the INL. Proliferation of cells was observed also in the ganglion cell and inner plexiform layers (*). DAPI staining of AdcmvGFP-contacted retinas showed no perturbations in the photoreceptor cell layer and no disturbances to the INL. Higher magnifications of boxed regions in the second column are shown in the third column.

FIG. 6 panel B is a set of photomicrographs of retinas contacted by injection with either AdcmvC3 (left) or AdcmvGFP (middle) or control eyes not injected (right), and stained with an antibody specific for rhodopsin. Rhodopsin (RHO) staining showed a loss of outer segments in AdcmvC3-contacted retinas, the RHO staining was observed predominantly in the outer segments of both AdcmvGFP-contacted retinas and uninjected retinas. Low levels of non-specific staining were observed in the sclera of some subjects.

FIG. 6 panel C is a set of photomicrographs of retinas contacted by injection with either AdcmvC3 (left) or AdcmvGFP (middle) or control eyes not injected (right), and stained for glial fibrillary acidic protein (GFAP), a protein found in glial cells. Data show an altered distribution of GFAP in the Muller cells of AdcmvC3-contacted retinas, specifically, GFAP staining was observed throughout the Muller cell from inner to outer limiting membranes. It was observed that Muller cells in AdcmvGFP-injected retinas showed GFAP staining that extended towards the outer retina. GFAP is typically localized to astrocytes and to the end feet of non-reactive Muller cells at the inner limiting membrane, as was observed in uninjected retinas.

FIG. 9 panel A shows photomicrographs of AdcmvC3-injected retinas visualized by BF (top row) and stained with DAPI (second row) or an anti-human C5b-9 antibody for MAC staining (bottom row). Data show MAC deposition on cells at the RPE/retinal interface. The MAC stained cells also stained positive for GSL I. Higher magnification images (right column) of boxed regions (left column) show punctate MAC staining characteristic of complement.

FIG. 9 panel B is a set of photomicrographs of AdcmvC3-injected retinas visualized by BF (top row, left) and stained with DAPI (top row, right), an anti-human C5b-9 antibody for MAC staining (bottom row, left), or GSL I (bottom row, right). Intense MAC staining was observed on the remaining outer segments of the photoreceptors of the AdcmvC3-contacted eyes.

FIG. 9 panel C is a set of photomicrographs of AdcmvGFP-injected retinas visualized by BF (top row, left) or GFP fluorescence (bottom row, right) and stained with DAPI (top row, right), or an anti-human C5b-9 antibody for MAC staining (bottom row, left). Strong MAC staining was observed in transduced RPE cells at the site of injection for AdcmvGFP-contacted retinas, and little or no MAC staining was observed in the retina.

FIG. 10 panel A is a drawing showing an adenovirus vector expressing a gene encoding either human CD46 protein (hCD46) or GFP protein under control of the chicken beta actin promoter. Also shown is a control empty vector expressing no transgene. Expression cassettes encoding hCD46, GFP, or control vector were cloned into the deleted E1 region (ΔE1) of a first generation adenovirus vector. Symbols used: CAG, cytomegalovirus chicken β-actin β-globin promoter; pA, polyadenylation signal; LITR, left inverted terminal repeat; RITR, right inverted terminal repeat; Ψ, Ad packaging signal; MLT, major late transcript; E, early region labels.

FIG. 10 panel B is a set of photographs of Western blots of lysates of human embryonic retinoblasts cells contacted with AdCAGCD46 (left column), AdCAGpA having no transgene (middle column) or control cells not contacted (right column), and then analyzed using a monoclonal antibody specific for binding to either human CD46 (top photograph) or beta (β)-actin (bottom photograph).

FIG. 10 panel C is a set of photomicrographs of mouse Hepa1c1c7 cells contacted with AdCAGCD46 (top row) or AdCAGpA (bottom row), visualized with BF (left column) and stained with mouse anti human CD46 (MEM258; right column) or DAPI (middle column). Hepa1c1c7 cells contacted with AdCAGCD46 were observed to have human CD46 localized on the cell membrane. No CD46 expression was observed for Hepa1c1c7 cells contacted with AdCAGpA.

FIG. 11 panels A-C are a set of bar graphs and photomicrographs showing that AdCAGCD46 protected mouse Hepa1c1c7 cells specifically from alternative pathway-mediated MAC deposition. Hepa1c1c7 cells were pre-treated with adenovirus then contacted with either 25 μg/ml emmprin antibody followed by 10% NHS to activate both classical and alternative pathways, or with 10 mM ethyleneglycoltetraacetic acid (MgEGTA)-treated NHS for inhibition of the classical pathway (i.e., activation of the alternative complement only). Data show that AdCAGCD46 selectively protected cells from alternative pathway-mediated MAC deposition.

FIG. 11 panel A is a set of bar graphs showing percent propidium iodide (PI) uptake on the ordinate for mouse hepa-1c1c7 cells as a function of contact with media from AdCAGCD46-contacted cells (right column) or media from AdCAGpA-contacted cells (third column from left). To activate both the alternative and classical complement pathways, cells were further contacted for 30 minutes at 4° C. with 25 μg/ml rat anti mouse emmprin (Abd Serotec Inc., MCA2283) in either NHS (left column) or HI-NHS (second column from the left). Reduced PI uptake was observed for cells contacted with HI-NHS compared to cells contacted with NHS. Cells contacted with media from AdCAGCD46-contacted cells showed slightly decreased PI uptake and cell death compared to cells contacted with media from AdCAGpA contacted cells. Data show that expression of hCD46 using an AdCAGCD46 injection had no significant effect on MAC deposition on mouse Hepa1c1c7 cells following activation of all pathways of the complement system. NHS=normal human serum; HINHS=heat-inactivated normal human serum; ns=not significant; PI=propidium iodide; BF=brightfield; MAC=membrane attack complex.

FIG. 11 panel B shows a set of bar graphs showing fluorescence-activated cell sorter (FACS) cell lysis analysis for the alternative pathway monitored by percent PI uptake on the ordinate in contacted mouse hepa-1c1c7 cells as a function of contact with media from AdCAGCD46-contacted cells (right column) or media from AdCAGpA-contacted cells (third column from left). The alternative pathway only was activated by contacting cells for 30 minutes at 4° C. with 7 mM magnesium and 10 mM EGTA in either NHS (left column) or HI-NHS (second column from the left). Control cells were not contacted with adenovirus vector and were contacted with NHS or HI-NHS only. In control cells, PI uptake was observed to be greater for cells contacted with NHS than for cells contacted with HI-NHS. Data show that cells contacted with AdCAGCD46 were effectively protected from cell lysis mediated by the alternative pathway. AdCAGCD46-contacted cells had 30-40% less PI uptake (i.e., less cell death) than cells contacted with AdCAGpA.

FIG. 11 panel C is a set of photomicrographs of mouse Hepa1c1c7 cells contacted with AdCAGCD46 (top row) or AdCAGpA (bottom row), contacted with 7 mM magnesium and 10 mM EGTA and NHS to activate the alternative complement pathway only, and then visualized with BF (left column) and stained for MAC (right column). Data show that Hepa1c1c7 cells contacted with AdCAGCD46 had healthier cell morphology and cell characteristics and had less MAC deposition on cellular membranes than cells contacted with AdCAGpA. Photomicrographs are representative of three separate experiments performed in duplicate each time.

FIG. 12 panel A is a set of photomicrographs of mouse hepa-1c1c7 cells contacted with either AdCAGCD46 (top row) or AdCAGpA (bottom row) and then incubated with EGTA in NHS and visualized by BF (left column) and stained for MAC deposition (right column). Media conditioned by AdCAGCD46 contacted cells reduced MAC deposition on hepa-1c1c7 cells compared to media conditioned by AdCAG-GFP contacted cells. Cell morphology of the hepa-1c1c7 cells treated with AdCAGCD46 was relatively normal and unchanged, and cells generally showed reduced MAC deposition compared to cells contacted with AdCAGpA. MAC staining intensity was faint and not uniform on cells contacted with AdCAGCD46. AdCAGpA infected cells displayed strong uniform MAC deposition.

FIG. 12 panel B is a graph of quantification of mean MAC pixel (staining) intensity on the ordinate as a function of media from adenovirus-contacted cells and serum to which mouse hepa-1c1c7 cells were contacted (abscissa). The hepa-1c1c7 cells were contacted with either AdCAGpA (left column) or AdCAGCD46 (right column) and then contacted with EGTA in NHS to produce alternative pathway MAC deposition. Quantification of MAC pixel intensity shows an overall reduction in staining intensity of $21\pm1.9\%$ ($p=0.04$) for AdCAGCD46 contacted RPE cells compared to AdCAGpA contacted RPE cells.

FIG. 14 panel A is a set of photomicrographs of a flat-mount of murine eyecups with the RPE cells exposed. Data show a patch of CD46 expression eight days after a sub-retinal injection of AdCAGCD46. Two views of the eyecups are shown including a higher magnification (right) of the boxed region of MAC staining (left).

FIG. 14 panel B shows BF visualizations (top row) and hCD46 expression staining (bottom) of cross sections through the injection site of subjects injected with AdCAGCD46. Data show visualizations of the un-injected side (left column) and the injected side (right column). It was observed that hCD46 expression was strongest on the basal and lateral surface of the RPE cells and that there was little or no detectable hCD46 expression in the un-injected region of the same eye.

FIG. 15 panel A is a set of photomicrographs showing the visualization of GFP (left column) and immunohistochemistry staining for MAC complex (right column) of eyes injected with either a mixture of AdCAGpA and AdCAGGFP (top row) or a mixture of AdCAGCD46 and AdCAGGFP (bottom row). A substantial decrease in MAC pixel intensity was observed for eyes injected with a mixture of AdCAGCD46 and AdCAGGFP compared to eyes injected with a mixture of AdCAGpA and AdCAGGFP. Arrows in the inset demarcate the periphery of the injected area.

FIG. 15 panel B is a set of photomicrographs using a higher magnification of the boxed regions of MAC staining for the eyecups injected with either a mixture of AdCAGpA and AdCAGGFP (left) or a mixture of AdCAGCD46 and AdCAGGFP (right) as shown in FIG. 15 panel A.

FIG. 15 panel C is a bar graph showing quantification of MAC pixel intensity of eyecups on the ordinate as a function of the mixture injected into the eyes (abscissa). Eyes were injected with either a mixture of AdCAGpA and AdCAGGFP or a mixture of AdCAGCD46 and AdCAGGFP, on the abscissa. Data show a $24\pm4.5\%$ ($p=0.0001$) reduction in MAC staining in AdCAGCD46-contacted eyecups compared to AdCAGpA-contacted eyecups. Data are representative images for assays. AdCAGpA n=7 and AdCAGCD46 n=9.

FIG. 15 panel D is a photomicrograph of a cross-section of an uninjected eye exposed to serum then stained for MAC. Data show that most of the MAC was deposited on the apical surface of RPE cells.

FIG. 16 panel A is a drawing showing an adenovirus vector expressing under control of the chicken beta actin promoter a gene encoding either hCD55 or GFP protein, and a control vector expressing no transgene. Expression cassettes were cloned into the deleted E1 region of serotype 5 adenovirus in an anti-sense orientation with respect to the E1 enhancer. hCD55 and GFP were expressed from a CAG promoter. Symbols used: CAG, cytomegalovirus chicken $\beta$-actin $\beta$-globin promoter; pA, polyadenylation signal; LITR, left inverted terminal repeat; RITR, right inverted terminal repeat; $\Psi$, Ad packaging signal; MLT, major late transcript; E, early region labels.

FIG. 16 panel B is a set of photographs of Western blots of human embryonic retinoblasts (HER) cell administered lysates (L) or media (M) contacted with adenovirus vector expressing a gene encoding hCD55 (AdCAGCD55) or a control adenovirus vector encoding no transgene (AdCAGpA). Western blots were analyzed using a monoclonal antibody specific to hCD55 (top photograph) or a monoclonal antibody specific to $\beta$-actin (bottom photograph). Control lysates or media were not contacted with adenovirus (Uninfected). Data show detectable hCD55 expression in AdCAGCD55-contacted HER cells and not in AdCAGpA-contacted HER cells.

FIG. 16 panel C is a set of photomicrographs of mouse Hepa1c1c7 cells contacted with media conditioned with AdCAGpA (top row) or AdCAGCD46 (bottom row). Cells were visualized with BF (left column) and were stained with mouse anti human CD55 (right column) Photomicrographs were visualized at 40× magnification. It was observed that AdCAGCD55-contacted mouse hepa1c1c7 cells showed hCD55 expression and localization at the cell membrane.

FIG. 17 panel A is a bar graph showing percent cell lysis on the ordinate of hepa1c1c7 cells as a function of adenovirus vector (abscissa): uninfected, AdCAGpA, or AdCAGCD55. Cells were injected at a multiplicity of infection (MOI) of 1000 viral particles in 10% NHS (open bars) or HI-NHS (closed bars). Data show greater cell lysis for hepa1c1c7 cells contacted with NHS compared to cells contacted with HI-NHS. Cells contacted with AdCAGCD55 were four- to five-fold less likely to lyse than cells contacted with AdCAGpA or control cells not injected. Data were collected from four independent experiments (n=10).

FIG. 17 panel B are printouts of cell sorting data showing results of human serum cell lysis assays with extent of propidium iodide (PI) labeling of injected cells shown on the abscissa (acquired in the FL3-H channel) and the number of cells on the ordinate. Hepa1c1c7 were contacted with AdCAGpA (middle) or AdCAGCD55 (right), or control cells were not injected (left), and then treated with either NHS or HI-NHS. Data show that untreated cells treated with HI-NHS sorted to a location of lesser PI uptake than untreated cells treated with NHS (i.e., greater PI uptake and cell lysis). Cells contacted with AdCAGGFP vector were observed to sort similarly to untreated cells. Data show that substantially all of the cells treated with vector AdCAGCD55 sorted to the same position as those treated with HI-NHS, i.e., susceptibility to NHS was substantially decreased or even entirely eliminated by pretreatment with AdCAGCD55. These data show that cells were protected from cell lysis due to expression of human CD59 from the AdCAGCD59 vector, rather than from contact with control adenovirus vector.

FIG. 18 panel A is a set of representative photomicrographs of murine hepa1c1c7 cells contacted with either AdCAGpA (top row) or AdCAGCD55 (bottom row) at a MOI of 1000 viral particles, incubated with 10% NHS, and then visualized with BF (left column) and stained with a monoclonal antibody specific for MAC (right column). Photomicrographs show dramatically reduced MAC staining for cells contacted with AdCAGCD55 compared to cells contacted with AdCAGpA.

FIG. 18 panel B is a bar graph showing quantification of MAC fluorescence intensity (MAC staining) of murine hepa1c1c7 cells on the ordinate as a function of adenovirus vector (abscissa): AdCAGpA (left) or AdCAGCD55 (right). Data show 61% reduction in staining in AdCAGCD55-contacted cells compared to AdCAGpA-contacted cells. Results were obtained from four independent experiments (n=11). ***p<0.0001 (paired t test).

FIG. 19 panel A is a set of photomicrographs showing GFP fluorescence (left column) and hCD55 expression (right column) for flatmounts of eyecups injected with a mixture of vectors AdCAGpA and AdCAGGFP (top row) or a mixture of vectors AdCAGCD55 and AdCAGGFP (bottom row). Immunohistochemistry of AdCAGCD55-injected eyes showed a section/patch of hCD55 expression coincident with the GFP expression at the site of injection. A portion of eye cup that folded onto itself is indicated by (*).

FIG. 19 panel B is a set of photomicrographs of representative cross sections through an injection site of an eye injected with a mixture of vectors AdCAGCD55 and AdCAGGFP. It was observed that hCD55 expression was located on the apical, basal and lateral surface of the RPE cells.

FIG. 20 panel A is a set of photomicrographs of flatmounts of eyecups contacted with a mixture of vectors AdCAGCD55 and AdCAGGFP (top row) or a mixture of vectors of AdCAGpA and AdCAGGFP (bottom row), and then contacted with NHS. Flatmounts were visualized for GFP fluorescence (left column in each set), and then stained for MAC staining (middle column in each set) with anti-human C5b-9 antibody. Merge (right column in each set) is an overlay of the GFP and the MAC dissected tissue photograph. MAC staining of flat mounted eyecups injected with a mixture of AdCAGCD55 and ADCAGGFP and incubated with NHS showed reduced MAC deposition compared to eyecups injected with a mixture of AdCAGpA and ADCAGGFP. The expression of hCD55 in the eyes caused reduction of MAC deposition. Images are representative of three independent experiments (AdCAGCD55, n=11; AdCAGpA, n=8). Boxes indicate regions shown below flatmounts at higher magnification. Higher magnification of individual RPE cells is shown in lower left.

FIG. 20 panel B is a bar graph of quantification of percentage of MAC staining intensity relative to the uninjected region (ordinate) as a function of adenovirus vector pretreatment of flatmount eyecups (abscissa). Eyecups were pretreated with a mixture of AdCAGpa and AdCAGGFP (left bar) or a mixture of AdCAGCD55 and AdCAGGFP (right bar). Data show that adenovirus-delivered hCD55 (AdCAGCD55) resulted in a significant reduction (55.7%) in flatmount MAC deposition on mouse RPE compared to adenovirus-delivered AdCAGpA. ***p<0.0001 (paired t test).

FIG. 22 panel B is a photograph of a Western blot of media of human RPE (ARPE19) cells contacted with AdCAGSTAC (right columns) or AdCAGGFP (left columns) and analyzed using a monoclonal antibody specific for binding to either human CD59, human CD46, or human CD55. The Western blot shows presence of antigen from each of human CD59 protein, human CD46 protein, and human CD55 protein in medium of cells contacted with AdCAGSTAC. Dark bands were observed at approximately 130 kD and faint bands were observed at approximately 150 kD in the medium of the ARPE19 cells (FIG. 22 panel B right three columns). Human CD59, human CD46, and human CD55 signal were not detected in medium from ARPE19 cells contacted with AdCAGGFP control vector (FIG. 22 panel B left three columns).

FIG. 23 panel A is a set of photomicrographs of mouse hepa-1c1c7 cells contacted with media conditioned by ARPE19 cells contacted by either AdCAGGFP (top row) or AdCAGSTAC (bottom row) and then incubated with 10% (v/v) normal human serum (NHS) and visualized by antibody stain for deposition of membrane attack complex (MAC). The left column shows hepa-1c1c7 cells visualized by bright field (DIC) microscopy. The right column shows the same hepa-1c1c7 cells stained for both for DAPI, which stains the nucleus, and MAC. Increased magnifications of the highlighted portions of the photomicrographs are also shown. Medium conditioned by ARPE19 cells contacted by AdCAGSTAC reduced MAC deposition on hepa-1c1c7 cells after NHS incubation compared to medium conditioned by AdCAGGFP contacted ARPE19 cells. Cell morphology of the hepa-1c1c7 cells treated with medium conditioned by AdCAGSTAC contacted ARPE19 cells was relatively normal and unchanged.

FIG. 23 panel B is a graph of quantification of MAC pixel (staining) intensity, ordinate, as a function of source of media from adenovirus-contacted ARPE-19 cells and serum to which mouse hepa-1c1c7 cells were contacted, abscissa. The hepa-1c1c7 cells were contacted with medium conditioned by ARPE19 cells contacted by either AdCAGGFP (left most bars) or AdCAGSTAC (right most bars) and then contacted with NHS (on the left in each pair) or heat inactivated (Hi) NHS (on the right in each pair). The treated hepa-1c1c7 cells were contacted with: AdCAGGFP medium and NHS (left), AdCAGGFP medium and HI-NHS (right), AdCAGSTAC medium and NHS (left), or AdCAGSTAC medium and HI-NHS (right). Cells deposited lower levels of MAC after contact with HI-NHS compared with NHS. Lower levels of MAC were also observed for cells contacted with medium conditioned by AdCAGSTAC contacted ARPE19 cells compared to cells contacted with medium conditioned by AdCAGGFP contacted ARPE19 cells.

FIG. 23 panel C is a line graph showing cell lysis monitored by percent propidium iodide (PI) uptake (ordinate) in contacted mouse hepa-1c1c7 cells as a function of concentration of NHS or heat inactivated (HI) NHS (% NHS; abscissa). Reduced PI uptake was observed for cells contacted with HI-NHS compared to cells contacted with NHS. Contact of cells with medium from AdCAGSTAC-contacted ARPE19 cells resulted in decreased cell death even with 2% percent NHS compared to contact of cells with medium from AdCAGGFP-contacted ARPE19 cells. Contact with medium from AdCAGSTAC-contacted ARPE19 cells resulted in 4.5-fold less PI uptake in cells compared to contact with medium from ARPE19 cells contacted with AdCAGGFP vector. Cells contacted with the medium from AdCAGGFP-contacted ARPE19 cells showed 70% PI uptake lysis of cells even at lower percent NHS.

FIG. 24 panel A is a set of photographs of DIC staining (left photomicrograph) and GFP fluorescence (right photomicrograph) of liver sections of a subject seven days after injection with AdCAGGFP vector. The images show transduction of the adenovirus on the liver capsule.

FIG. 24 panel B is a set of photographs of DIC staining (left photomicrograph) and MAC staining (right photomicrograph) of cross sections taken from the center of the left liver lobes of subjects injected with AdCAGGFP vector (top row) or AdCAGSTAC vector (bottom row), then seven days later injected with anti-mPECAM1/NHS into the left ventricle. The liver sections from the subject injected with AdCAGSTAC vector showed little or no MAC staining compared to the subject injected with AdCAGGFP vector (p=0.0014).

FIG. 24 panel C is a bar graph showing mean pixel intensity (ordinate) of MAC staining in subjects injected with an adenovirus prior to injection with anti-mPECAM1/NHS (abscissa). The injected adenovirus vector strain used was control AdCAGGFP (left bar), or AdCAGSTAC (right bar). A reduced mean pixel intensity of MAC staining was observed in liver sections from mice injected with AdCAGSTAC compared to in liver sections from mice injected with AdCAGGFP. Data were obtained from seven mice injected with AdCAGGFP and eight mice injected with AdCAGSTAC (p=<0.0001).

DETAILED DESCRIPTION

Figure 1A:
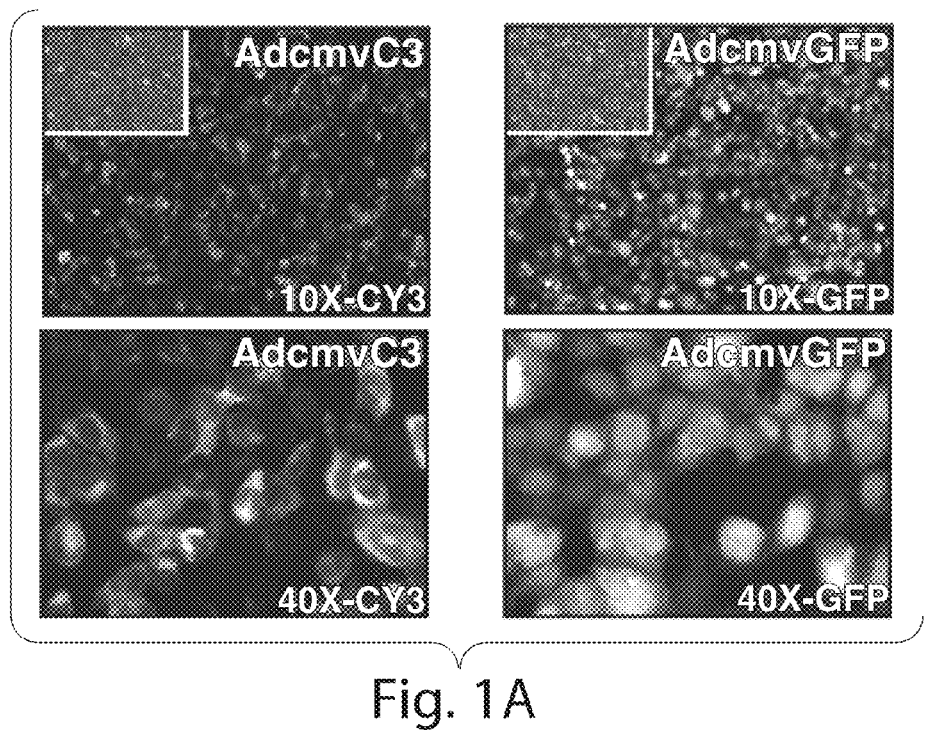
FIG. 1 panels A-B are a set of photomicrographs and photographs of Western blots showing efficient secretion of C3 expressed from adenovirus in vitro.

Dysregulation of the complement system is considered to be one of the major factors contributing towards the etiology of AMD, one of the leading causes of blindness in the elderly (Gehrs et al. 2010 Arch Ophthalmol 128: 349-358). The most devastating form of the disease affects approximately 10% of patients (Klein 2008 Ophthalmology 115: 1026-1031), and involves the growth of attenuated blood vessels from the choroidal vasculature through Bruch's membrane and into the retina. The plasma released by these "ill-formed" vessels damages photoreceptors and other retinal cells, eventually leading to a severe loss of vision. The vast majority of AMD patients, however, present with extracellular deposits which occur between the retinal pigment epithelium (RPE) and Bruch's membrane called drusen and which eventually lead to atrophy of the RPE (geographic atrophy).

A potential role for complement in AMD was considered because complement proteins were identified in drusen of AMD eyes (Johnson et al. 2001 Exp Eye Res 73: 887-896; Johnson et al. 2000 Exp Eye Res 70: 441-449; Mullins et al. Eye (Lond) 15: 390-395; and Mullins et al. 2000 FASEB J 14: 835-846). Polymorphisms have been identified in a number of complement genes and were observed to be either strongly predictive of or protective against AMD. A single amino acid change, Y402H, in factor H accounts for as much as 40-50% of AMD in aging eyes (Edwards et al. 2005 Science 308: 421-424; Hageman et al. 2005 Proc Natl Acad Sci USA 102: 7227-7232; and Haines et al. 2005 Science 308: 419-421).

Haplotype variants in both Factor B and complement component 2 (C2) result in a significantly reduced risk of developing AMD (Gold et al. 2006 Nat Genet. 38: 458-462), and an R80G substitution in complement component 3 (C3) increased the risk of having AMD to as much as 22% (Yates et al. 2007 N Engl J Med 357: 553-561). The factor B (32Q) variant has been shown to have a 4-fold lower binding affinity for C3b, with a reduced ability to form the convertase (Montes et al. 2009 Proc Natl Acad Sci USA 106: 4366-4371). In addition, polymorphisms in C2, C3, and factor B have been shown to be significantly linked with progression to both types of advanced AMD disease, choroidal neovascularization and geographic atrophy (Klein 2008 Ophthalmology 115: 1026-1031; Maller et al. 2007 Nat Genet. 39: 1200-1201; and Reynolds et al. 2009 Invest Ophthalmol Vis Sci 50: 5818-5827).

Evidence for complement-induced retinal pathology has been primarily found for AMD, and indications of a role for complement activation in other retinal diseases is accumulating. Deposition of complement proteins has been observed in the choriocapillaris of patients with diabetic retinopathy (Gerl et al. 2002 Invest Ophthalmol Vis Sci 43: 1104-1108), as well as in retinal vessels of diabetic subjects (Zhang et al. 2002 Diabetes 51: 3499-3504). The retinal vessels exhibited a significant reduction in expression of complement regulatory proteins CD55 and CD59. Complement components have also been observed in the epiretinal membranes of patients suffering from proliferative vitreoretinopathy (PVR), and upregulation of the classical pathway initiator protein, C1q, as well as altered expression of other proteins of the cascade have been observed in glaucomatous eyes (Baudouin et al. 1990 Am J Ophthalmol 110: 593-598; Stasi et al. 2006 Invest Ophthalmol Vis Sci 47: 1024-1029; and Tezel et al. 2010 Invest Ophthalmol Vis Sci 51(11): 5697-707).

There are few animal models that directly investigate the role of complement in retinal function and pathology. Most of these models have analyzed at the impact of different complement proteins in the development of laser-induced choroidal neovascularization (CNV) in the mouse retina. Other studies have demonstrated the dependence of retinal pathology on the alternative pathway, rather than classical or lectin pathway, and on the formation of the membrane attack complex (Bora et al. 2007 J Immunol 178: 1783-1790; Bora et al. 2006 J Immunol 177: 1872-1878; and Bora et al. 2005 J Immunol 174: 491-497). Previous studies have demonstrated a significant role played by the anaphylatoxins, C3a and C5a, in the development of CNV (Nozaki et al. 2006 Proc Natl Acad Sci USA 103: 2328-2333). Aged mice with deficiency of factor H exhibited altered architecture in Bruch's membrane, RPE and photoreceptors, and reduced ERGs (Coffey et al. 2007 Proc Natl Acad Sci USA 104: 16651-16656), and manifested a loss of integrity of retinal vessels (Lundh von Leithner et al. 2009 Am J Pathol 175: 412-421). The alternative complement pathway has been implicated also as a major factor in light-induced retinal degeneration which has been shown to be significantly reduced in a mouse deficient in Factor D (Rohrer et al. 2007 Invest Ophthalmol Vis Sci 48: 5282-5289). Ganglion cells of C3-deleted mice exhibited transient, but significant, protection from degeneration due to retinal ischemia reperfusion (Kuehn et al. 2008 Exp Eye Res 87:89-95).

One of three distinct complement pathways (classical, lectin or alternative) initiates the complement cascade (Markiewski et al. 2007 Am J Pathol 171: 715-727) and these pathways converge at the point in the pathway of the breakdown of C3 into C3a and C3b. The breakdown of C3 initiates the final part of the pathway that culminates in the formation of the membrane attack complex (MAC), a pore-like structure which inserts in the membranes of self- or non-self cells causing their lysis. In addition to the potential for cell lysis by the production of the opsonin C3b, activation of C3 generates the anaphylatoxins, C3a and C5a, both of which are powerful and pleiotropic effectors of inflammation. Unlike the classical or lectin pathways, the alternative pathway is constitutively active with small amounts of C3 hydrolysis and conversion to the convertase occurring in the serum. The effects of complement over-expression in mouse retina, specifically by determining the consequences of an increased local expression of C3 in mouse retina on retinal anatomy and function are analyzed in Examples herein. Without being limited by any particular theory or mechanism of action, it is here envisioned that a local increase in C3 expression resulted in a local increase in C3 hydrolysis and conversion to the convertase. Methods, compositions and kits described herein increased expression of C3 by injection into the sub-retinal space of an adenovirus expressing murine C3 regulated by the cytomegalovirus (CMV) promoter. Scotopic electroretinograpy, fluorescein angiography and histological analyses in Examples herein showed that that increased expression of C3 in murine RPE caused significant functional and anatomical changes in the murine retina.

C3

Inhibitors of complement, such as factor H and CD59, have been shown to impact the development of choroidal neovascularization in response to laser-induced damage of Bruch's membrane (Bora et al. 2005 J Immunol 174: 491-497; Bora et al. 2006 J Immunol 177: 1872-1878; Bora et al. 2007 J Immunol 178: 1783-1790; and Rohrer et al. 2009 Invest Ophthalmol Vis Sci 50: 3056-3064). Aged Factor H-deficient mice were observed to have deposition of C3 and C3b in retinal vasculature, which resulted in attenuation of retinal vessels and reduced blood flow (Lundh von Leithner 2009 Am J Pathol 175: 412-421). Examples herein show consequences of local C3 over-expression in the RPE of murine retina. Adenovirus expressing either murine C3 or GFP from a CMV promoter were injected into the mouse sub-retinal space and eight days or 14 days post-injection, eyes were analyzed to determine the effect of local exogenous C3 production. Without being limited by any particular theory or mechanism of action, it is envisioned that an increased expression of C3 in murine RPE increased local C3 hydrolysis, convertase production, and complement activation.

A large proportion of patients with advanced AMD present with a spurious growth of new blood vessels from the choroid into the subretinal space (Klein et al. Ophthalmology 115: 1026-1031), and a significant subset of neovascular patients present with new vessels originating from the inner retina (Yannuzzi et al. 2001 Retina 21: 416-434). These immature blood vessels leak fluid causing retinal detachment and degeneration. The relationship between complement activation and growth of new and "leaky" blood vessels in AMD eyes was unclear. Animal models have shown that regulators of complement, such as Factor H and CD59, can significantly reduce neovascularization in the laser-induced model of CNV (Bora et al. 2007 J Immunol 178: 1783-1790; and Rohrer et al. 2009 Invest Ophthalmol Vis Sci 50: 3056-3064). Murine subjects deficient in receptors for C3a and C5a exhibited significantly reduced laser-induced endothelial cell proliferation (Nozaki et al. 2006 Proc Natl Acad Sci USA 103: 2328-2333). The anaphylatoxin, C3a, increases vascular permeability through structural changes in the endothelium (Markiewski et al. 2007 Am J Pathol 171: 715-727) and C5b-9 has been shown to affect endothelial cell proliferation and migration in models of atherosclerosis (Rohrer et al. 2009 Invest Ophthalmol Vis Sci 50: 3056-3064), and to induce the release of growth factors such as basic fibroblast growth factor (Benzaquen et al. 1994 J Exp Med 179: 985-992). Local exogenous expression of C3 was observed in Examples herein to induce both leakiness of blood vessels and proliferation of endothelial cells in murine retina. C3-injected eyes exhibited signs of leakage as little as eight days after administration of the virus, a time-point at which a significant amount of endothelial cell staining was also observed throughout the choroid and retina. Deposition of MAC was evident on endothelial cells at the RPE-retinal interface, as well as on remnants of the photoreceptor outer segments. The retinal detachment observed within the region of endothelial cell proliferation/migration in C3-injected retinas occurred as a result of leakage of fluid from the vasculature into the subretinal space. C3-injected eyes examined 14 days following injection exhibited significant levels of leakiness.

AMD patients generally initially present with pigmentary changes in the RPE, manifesting as areas of both hyper- and hypo-pigmentation (Klein et al. 2007 Ophthalmology 114: 253-262). The pigmentary changes progress in approximately 40% of advanced AMD cases to geographic atrophy in which areas of RPE cell loss through which choroidal vessels and an overlying area of photoreceptor degeneration are observed. Previous studies have observed transdifferentiating and migrating RPE cells in intimate association with choroidal neovascular membranes of AMD patients (Lopez et al. 1996 Invest Ophthalmol Vis Sci 37: 855-868). RPE cells have also been shown to migrate into the retina in proliferative vitreoretinopathy (Fisher et al. 2005 Prog Retin Eye Res 24: 395-431; and Hiscott et al. 1999 Prog Retin Eye Res 18: 167-190).

Retinas contacted with adenovirus expressed C3 showed a loss of RPE cells and pigmentation, and a loss of photoreceptor outer segments in the region of endothelial cell proliferation. The C3-contacted retinas were observed to have pigmentary deposits in close association with cells staining positive for the endothelial cell marker, GSL I, and in some cases these cells could be observed penetrating the retina. An increase in endothelial cell staining was also observed within the region of injection in the choroid (and in some cases the retina) of GFP-contacted eyes, however these proliferating endothelial cells did not penetrate the RPE. An Ad5 expressing red fluorescent protein from a CMV promoter has been shown not to cause CNV when injected into the subretinal space (Cashman et al. 2006 Invest Ophthalmol Vis Sci 47: 3496-3504). A titer of adenovirus was used in Examples herein that was approximately 20-fold less than was used in this previous analysis.

Increased VEGF has been observed in the eyes of AMD patients, and inhibitors of VEGF and VEGF receptors are highly effective in controlling and reducing exudative disease (Ozkiris 2010 Expert Opin Ther Pat 20: 103-118). The anaphylatoxins, C3a and C5a, have been shown to induce VEGF in the mouse RPE (Nozaki et al. 2006 Proc Natl Acad Sci USA 103: 2328-2333). The complex relationship between CNV development and angiogenic factors such as VEGF, bFGF and HGF has been investigated in the laser-induced model of neovascularization (Flu et al. 2009 Exp Eye Res 88: 79-91).

Increased VEGF expression for C3-contacted eyes three days following injection was observed herein. The VEGF increase was not linked to C3 expression as a similar increase was observed in GFP-contacted eyes. Data show that increased VEGF expression was not detectable in C3-contacted retinas eight days following injection. Without being limited by any theory or particular mode of action, it is envisioned that the decline in VEGF mRNA levels observed at eight days post-injection was due to significant changes in VEGF-producing cells, such as the RPE and Muller cells (Saint-Geniez et al. 2004 Int J Dev Biol 48: 1045-1058) VEGF may have a role in development of the phenotype or the adenovirus itself may have contributed to the development of the pathology of AdcmvC3-injected retinas as activation of mouse complement has been observed previously for adenovirus (Tian et al. 2009 J Virol 83: 5648-5658).

Patients with either exudative AMD or with geographic atrophy show reduced cone and rod function as measured by electroretinography (Gerth 2009 Doc Ophthalmol 118: 63-68). The reduction in scotopic a- and b-wave amplitudes was observed to correlate with increasing light intensity (Walter et al. 1999 Graefes Arch Clin Exp Ophthalmol 237: 962-968). C3-contacted eyes were observed herein to have significantly reduced a-wave amplitudes, as measured by scotopic ERG, at the higher light intensity but not at the lower light intensity. B-wave amplitudes were also observed in Examples herein to be reduced at both light intensities compared to both GFP-contacted eyes or uninjected murine subjects. The observed reduction in retinal function indicates the loss of photoreceptor segments observed in C3-injected mice. Loss of outer segments is caused by vascular leakage and/or deposition of the MAC complex, which was observed on the remnant segments. Deposition of MAC at sub-lytic concentrations is associated with inhibition of apoptosis (Cole 2003 Clinical Science 104: 455-466), which explains the absence of TUNEL staining in AdcmvC3-injected retinas. No significant loss in ERG amplitudes was observed in GFP-injected mice compared with uninjected mice.

Activation of Muller cells (reactive gliosis) is a common feature of damage, e.g. retinal detachment, to the retina (Bringmann et al. 2006 Prog Retin Eye Res 25: 397-424). Muller cells have been shown to play a pivotal role in retinal detachment associated with fibrocontractive disorders such as proliferative vitreoretinopathy (PVR) and proliferative diabetic retinopathy, PDR (Guidry 2005 Prog Retin Eye Res 24: 75-86). Due to the intimate relationship between Muller cell processes and retinal blood vessels, increased vascular permeability is a concern during reactive gliosis. In addition, in human retinas distribution of the C3a receptor is consistent with presence of the receptor on Muller cells (Vogt et al. 2006 Exp Eye Res 83: 834-840). Examples herein show C3-contacted eyes had altered expression and distribution of the intermediate filament protein GFAP, indicating activation of Muller cells.

Mouse models of AMD exist that include transgenic mice requiring considerable aging of the mouse in addition to other special treatments such as high-fat diet to recapitulate some of the pathologies observed in AMD eyes (Edwards et al. 2007 Angiogenesis 10: 119-132; and Elizabeth-Rakoczy et al. 2006 Exp Eye Res 82: 741-752). These models are impractical for accelerated development of therapies for this disease. An ex-vivo model of human MAC deposition on murine RPE has been used to test complement regulators such as CD59 and CD55 (Ma et al. 2010 Invest Ophthalmol Vis Sci 51: 6776-6783; and Ramo et al. 2008 Invest Ophthalmol Vis Sci 49: 4126-4136). These models are laser-induced and VEGF-overexpression models that developed AMD-like symptoms quickly (within days or weeks of insult), and are primarily representative of the exudative form of the disease (Baffi et al. 2000 Invest Ophthalmol Vis Sci 41: 3582-3589; Grossniklaus et al. 2010 Prog Retin Eye Res 29(6): 500-519; Spilsbury et al. 2000 Am J Pathol 157: 135-144; and Wang et al. 2003 Invest Ophthalmol Vis Sci 44: 781-790), however the laser-induced CNV model has shown potential in elucidating the role of complement in CNV (Bora et al. 2007 J Immunol 178: 1783-1790; and Rohrer et al. 20096 Invest Ophthalmol Vis Sci 50: 3056-306). A system and assay are provided herein involving local increased expression of C3 in mouse retina using an adenovirus that models many of the pathologies observed in AMD eyes—neovascularization, increased vascular permeability, RPE atrophy, hypo-pigmentation, retinal detachment, photoreceptor degeneration, and reduced retinal function, but does so within one to two weeks of virus administration. The systems, methods, compositions and kits described herein are useful in further elucidating the role of complement not only in AMD, and in other retinal diseases such as PVR and PDR, and in the development of therapies for complement-mediated retinal diseases, such as AMD.

Examples herein show systems, compositions, methods and kits for assaying potential therapeutic agents for treatment of complement-based ocular diseases. The systems, methods and kits include assays showing an animal model of complement-based ocular diseases through the overactivation of natural complement takeover. The assays are for example in vitro or in vivo. For example the natural complement takeover is overactivated using adenovirus vectors having a nucleic acid that encode C3.

Without being limited by any particular theory or mechanism of action, it is here envisioned that increased expression of C3 in ocular cell or on ocular tissues such as the retinal pigment epithelium increases C3 hydrolysis, C3-convertase production, and complement activation. The activation of the complement cascade forms different products including anaphylatoxins such as C3a and C5a, and membrane attack complex that causes cell lysis and significant functional and anatomical negative changes to ocular cells and tissue including damaged photoreceptor cells and vascular leakage in the retina. These changes are associated with ocular diseases and conditions, which are retinal pathologies that affect millions of patients throughout the world.

Systems, methods and kits are provided for identifying a therapeutic agent that treats or prevents a complement-associated ocular disease that affects an ocular cell or ocular tissue. The phrase "complement-associated ocular disease" as used herein and in the claims includes without limitation a "complement-based ocular disease" and refers to an ocular disease, pathology or condition associated with complement activation or overactivation or natural complement takeover. The phrase "ocular tissue" as used herein and in the claims includes without limitation an "ocular surface" and refers to a tissue or surface of the eye or the ocular mucosa. Examples of ocular tissues include retinal pigment epithelium, pupil, cornea, iris, lens, aqueous humor, retina, choroid, sclera, fovea, eye muscles such as ciliary muscles or orbital muscles, glands such as the lacrimal glands, and the conjunctiva. A complement-based ocular disease as used herein refers to a disease characterized by function of complement proteins or overactivation of natural complement takeover in an ocular cell or tissue, for example complement-based ocular diseases include age-related macular degeneration, glaucoma, retinal pigmentosa, and proliferative vitreoretinopathy.

In various embodiments, the methods and kits herein include a C3 protein or a vector having a nucleic acid that encodes C3 exemplified by amino acid sequence shown. See Bednarczyk, J. L. et al.1988 Scand J Immunol 27: 83-95; and Van den Berg, C. W. et al., 1989 J Immunol Methods 122: 73-78. Additional exemplary amino acid sequences are obtained by mutating the nucleic acid sequence encoding C3 to obtain point mutations, substitutions or deletions having a nucleic acid sequence that encodes a modified amino acid sequence, encoding a protein that retains the binding function capable of binding the therapeutic agent or imaging agent to the ocular cell or ocular tissue.

The C3 herein is envisioned to include conservative sequence modifications in residues of the protein or in residues modified by conservative amino acid changes that do not reduce the overactivation of natural complement takeover function. As used herein, the term "conservative sequence modifications" refers to amino acid modifications that do not significantly affect or alter the functional characteristics of the protein or peptide. Such conservative modifications include amino acid substitutions, additions and deletions. Modification of the amino acid sequence of C3 is achieved using any known technique in the art e.g., site-directed mutagenesis or PCR based mutagenesis. Such techniques are described in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

Conservative amino acid substitutions are changes in the C3 in which an amino acid residue is replaced with a different amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the amino acid sequence of the C3 is substantially identical to that of a wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 30% identity, or at least 40%, 50%, 60%, 70%, 75%, 80%, 85%, 90%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., Nuc. Acids Research 22:4673, 1994 (www.ebi.ac.uk/clustalw), BL2SEQ by Tatusova and Madden, FEMS Microbiol. Lett. 174:247, 1999 (www.ncbi.nlm.nih.gov/blast/b12seq/b12.html), SAGA by Notredame and Higgins, Nuc. Acids Research 24:1515, 1996 (igs-server.cnrs-mrs.fr/~cnotred), and DIALIGN by Morgenstern et al., Bioinformatics 14:290, 1998 (bibiserv.techfak.uni-bielefeld.de/dialign).

An aspect of the invention herein provides a model system for diagnosing or prognosing an ocular pathology or for screening potential therapeutic agents including: a first sample of cells or tissue contacted with a vector including a nucleic acid encoding complement component 3 (C3) to overactivate natural complement takeover in the cells or the tissue; a second sample of cells or tissue contacted with a control nucleic acid encoding a detectable protein, such that the vector and the control vector include the same promoter sequence operably linked to nucleic acids encoding the C3 and the detectable protein, such that the detectable protein is a control that does not overactivate the natural complement takeover, such that the second sample of the cells or tissue are otherwise identical to the first sample of the cells or tissue contacted with the vector; a control sample of cells or a tissue from a normal subject, such that the normal subject is not affected by a complement-based ocular disease or the ocular pathology; and a marker associated with complement activation for measuring in each of the first sample, the second sample and the control sample, such that the marker is characteristic of the disease and retinal pathology, such that an amount of the marker in the third sample compared to amounts in the first sample and the second sample is a measure of prognosis or diagnosis of the complement-based ocular disease or the ocular pathology.

In various embodiments of the system, the C3 is a mammalian C3 for example C3 derived from a human, a mouse, a cow, a pig, a rabbit, a goat, or a dog.

In related embodiments of the system, the vector includes a viral vector, for example an adenovirus, an adeno-associated virus, a retrovirus, a herpesvirus, and a lentivirus. In related embodiments, the vector includes a plasmid vector.

In related embodiments of the system, the detectable protein is at least one selected from: a fluorescent protein, an enzyme having a colorimetric assay, and a chemifluorescent protein, for example the fluorescent protein is at least one selected from the group consisting: green fluorescent protein, enhanced green fluorescent protein, aequorin, cyan fluorescent protein, DsRed fluorescent protein, and yellow fluorescent protein.

In related embodiments of the system, the marker includes at least one selected from: a membrane attack complex protein, glial fibrillary acidic protein, vascular endothelial growth factor, and *Griffonia simplicifolia* lectin I. In related embodiments of the system, the marker is a complement component or complement protein such as an anaphylatoxin, such as C3a or C5a.

In related embodiments, prior to contacting, the cells or the tissues are cultured in vitro. In related embodiments, the cells or tissue are contacted in an animal model in vivo. For example the animal model is a mouse model. In related embodiments, the cells or the tissue includes ocular cells or ocular tissues, respectively.

In related embodiments, the cells or tissue are contacted by injection, for example by at least one route of administration selected from: intra-ocular, invitreal, subconjunctival, subretinal, and subtenon. In various embodiments, the cells or tissue are contacted topically.

In related embodiments, the marker includes at least one selected from the group of: a membrane attack complex protein, glial fibrillary acidic protein, vascular endothelial growth factor, and *Griffonia simplicifolia* lectin I. In related embodiments, measuring includes observing cellular staining or tissue staining, for example staining of a cellular membrane or nucleus.

In related embodiments of the system, measuring includes observing at least one from the group of: increased vascular permeability, increased endothelial cell proliferation and migration, RPE atrophy, loss of photoreceptor outer segments, reactive gliosis, increased drusen formation, Muller cell activation, formation of membrane attack complex, retinal detachment, and reduced retinal function. For example, the first sample of the cells or the tissue is characterized as having loss of integrity of retinal vessels.

An aspect of the invention herein provides a method for diagnosing a complement-based ocular disease in cells or tissue from a subject, the method including: contacting a first sample of the cells or tissue from the subject with a vector including a nucleic acid encoding complement component 3 (C3), such that the C3 overactivates natural complement takeover in the cells or the tissue; measuring an amount of a marker in the first sample, such that the marker is characteristic of the disease; and comparing amounts of the marker in the first sample to amount of the marker in a second sample of cells or tissue from the subject not so contacted to the vector and otherwise identical, such that amount of the marker in the first sample of cells is compared to that in the cells or the tissue from the subject, such that a substantially similar amount or even greater amount of the marker in the second sample compared to the amount of the marker in first sample is an indication of the diagnosis of the complement-based ocular disease in the subject. In related embodiments of the method, the cells or the tissue includes ocular cells or ocular tissues, respectively.

In related embodiments, the method further includes obtaining a control sample of cells or tissue from a normal subject, such that the normal subject is not affected by the complement-based ocular disease, and measuring an amount of the marker in the control sample, such that a greater amount of the marker in the second sample and/or first sample compared to the amount of the marker in the control sample is an indication of presence of the complement-based ocular disease or ocular pathology in the subject. For example, the method indicates the presence of age-related macular degeneration.

An aspect of the invention herein provides a method of identifying in a model system a potential therapeutic agent for treating or preventing a complement based-ocular disease, the method including: contacting a first sample of cells or tissue with a vector including a nucleic acid encoding complement component 3 (C3) to overactivate natural complement takeover in the cells or the tissue, contacting a second sample of the cells or tissue with a control nucleic acid encoding a detectable protein, such that the vector and the control vector include the same promoter sequence operably linked to nucleic acids encoding the C3 and the detectable protein, such that the detectable protein is a control that does not overactivate the natural complement takeover, and contacting at least a third sample of cells or tissue with the nucleic acid encoding the C3 and at least one of a plurality of potential therapeutic agents; and measuring in the first sample, the second sample and the third sample, an amount of the marker, such that the marker is characteristic of the disease, such that the amount of the marker in the third sample compared to that in the first sample and/or the second sample is a measure of treatment and protection by the potential therapeutic agent, such that a decreased amount of the marker in the third sample compared to the first sample is an indication that the agent is therapeutic, thereby identifying the potential therapeutic agent for treating or preventing the complement-based-ocular disease.

In related embodiments of the method, the complement based-eye disease includes age-related macular degeneration (AMD) condition, for example wet AMD or dry AMD.

In related embodiments of the method, the detectable protein is at least one selected from: a fluorescent protein, an enzyme having a colorimetric assay, and a chemifluorescent protein. In related embodiments, the fluorescent protein is at least one selected from the group of: green fluorescent protein, enhanced green fluorescent protein, aequorin, cyan fluorescent protein, DsRed fluorescent protein, and yellow fluorescent protein.

In related embodiments, the promoter includes a cytomegalovirus (CMV) promoter, for example a human CMV promoter or mouse CMV promoter. In related embodiments, the vector includes a viral vector, for example the viral vector is an adenovirus, an adeno-associated virus, a retrovirus, a herpesvirus, or a lentivirus.

In related embodiments of the method, the marker includes a protein, an enzyme, a lipid, a carbohydrate, or a nucleic acid. In related embodiments, the vector is selected from the viral vector encoding a DNA or an RNA, a naked DNA vector, and a microencapsulated DNA or RNA.

In related embodiments, the marker includes at least one selected from the group of: membrane attack complex (MAC) or a MAC protein, glial fibrillary acidic protein, vascular endothelial growth factor, and *Griffonia simplicifolia* lectin I.

In related embodiments, measuring further includes observing a localization of the marker in the cells or the tissue contacted by at least one of the first sample, the second sample, and the third sample. For example, the method includes observing the localization of the marker within the cytoplasm or in a nucleus.

In related embodiments of the method, prior to contacting, the cells or the tissues are cultured in vitro. For example the cells or tissue are cultured in a tube, a flask, or a plate.

In related embodiments of the method, contacting is in an animal model in vivo. In related embodiments of the method, contacting includes injecting the cells or the tissue, for example by at least one route of administration selected from: intra-ocular, invitreal, subconjunctival, subretinal, and sub-tenon. In related embodiments of the method, contacting includes administering topically, for example to an ocular tissue or mucosal lining.

In related embodiments of the method, prior to contacting, the method includes engineering the vector having the nucleic acid encoding the C3 to express the C3 as a soluble protein.

In related embodiments, measuring further includes observing cellular staining or tissue staining, for example staining of a cellular membrane or nucleus. For example, measuring further includes observing the marker specifically located on the cells or the tissue, for example retinal pigment epithelium or retina.

In related embodiments, measuring further includes observing cellular morphology, cell viability, or tissue functionality in the samples. For example, the method includes observing decreased ocular functionality (e.g., retinal functionality) in the first sample compared to the second sample and/or third samples.

In related embodiment of the method, measuring further includes observing in the samples at least one selected from the group consisting of: retinal detachment, cellular pathology, and tissue pathology. In related embodiment of the method, measuring further includes performing electroretinography.

An aspect of the invention herein provides a kit for diagnosing or prognosing an ocular pathology and/or identifying a potential therapeutic agent for treating or preventing a complement based-ocular disease including: a vector including a nucleic acid encoding a component 3 (C3) that overactivates natural complement takeover in cells or tissue; a container; and, instructions for use. For example the instructions for use include methods described herein for identifying the potential therapeutic agent or for diagnosing or prognosing an ocular pathology.

In related embodiments, the kit further includes an anti-C3 antibody or an anti-MAC antibody. In related embodiments, the kit further includes a control vector including a control nucleic acid encoding a detectable protein absent the C3, such that the vector and the control vector include the same promoter sequence operably linked to nucleic acids encoding the C3 and the detectable protein, such that the detectable protein does not overactivate the natural complement takeover in the cells or the tissue. In related embodiments, the instructions for use in kits herein include any of the methods described herein.

In various embodiments, the methods and kits herein identifying a potential therapeutic agent for exudative choroidal diseases, herododystrophic diseases, retinal vascular disorders, and other diseases that associated with complement protein or the immune response. Methods and kits herein are useful for identifying a therapeutic agent that treats any of these diseases or conditions resulting in vision loss and ocular disease dysfunction.

Therapeutic Agents for Complement-related Conditions

Data in examples herein show regulation of complement activity by membrane-attached and soluble forms of human complement regulators CD46, CD55, and CD59 using mouse cells, e.g., RPE cells. (See Kumar-Singh PCT application PCT/US09/000,947 filed Feb. 13, 2009; Ramo et al. 2008. Invest Ophthalmol Vis Sci 49: 4126-4136; Ma et al. 2010 Invest Ophthalmol Vis Sci 51: 6776-6783, and Sweigard et al. 2011 Gene Therapy 18: 613-621, each of which is hereby incorporated by reference herein in its entirety). CD46 prevents formation of C3 convertase by acting as a cofactor for factor I mediated decay of C3b, an important regulator of complement. CD55 acts by dissociating the C3 convertase. CD59 regulates the complement pathway by preventing formation of the MAC complex. Data herein show that CD46, CD55 and CD59 individually and in combination were therapeutic agents that effectively eliminated and modulated complement-based cell lysis and disease.

CD46

CD46, also known as MCP (complement membrane cofactor protein), is a type I membrane protein that has cofactor activity for inactivation of complement components C3b and C4b by serum factor I (Barilla-LaBarca et al., J Immunol, 2002. 168(12): 6298-6304). Mature human CD46 protein is composed of 392 amino acids and has a molecular weight of about 48 kD to about 68 kD. CD46 is found in leukocytes, platelets, epithelial cells, sperm cells, and fibroblasts. Numerous transcript variants encoding different isoforms have been identified for this gene. Structures of different CD46 proteins are shown for example in U.S. Pat. No. 5,846,715 issued Dec. 8, 1998 to Purcell et al. which is incorporated by reference herein in its entirety.

Isoforms of human CD46 C1, C2, BC1, and BC2 have distinct molecular weights. For example, C1 and C2 have a molecular weight of about 56 kD and BC1 and BC2 have a molecular weight of about 66 kD. Isoforms ABC1 and ABC2 have a molecular weight of about 76 kD (358 amino acids and 365 amino acids respectively).

CD46 has four N-terminal short consensus (SCR) modules that are referred to as Sushi domains which are known motifs in protein-protein interactions. Sushi domains contain four cysteines forming two disulfide bonds in a 1-3 and 2-4 pattern. SCR modules 2-4 function in C3b/C4b binding and regulatory activity. CD46 is post-transcriptionally modified by glycosylation. See Stern et al. 1986 J Immunol 137: 1604-1609; Seya et al. 1986 J Exp Med 163: 837-855; Post et al. 1991 J Exp Med 174: 93-102; Russell et al. 1992 Eur J Immunol 22: 1513-1517; Okada et al. 1995 Proc Natl Acad Sci USA 137: 3689-3695; and Thorley et al. 1997 Eur J Immunol 27: 726-734.

Mutations in CD46 have been identified as a major risk factor for developing diseases associated with chronic alternative pathway activity, such as aHUS (Kavanagh et al. 2008 Annu Rev Med 59: 293-309). Although the importance of CD46 expression has been defined for aHUS, its role in AMD has not been fully evaluated. Analysis of the expression pattern for CD46 in normal human eyes revealed that it is expressed on the basal and lateral surfaces of RPE cells (Vogt et al. 2006 Exp Eye Res 83(4): 834-840). As the basal surface of RPE cells are exposed to drusen, CD46 is in a prime location to dampen alternative pathway activity. However, the levels of endogeneous CD46 may not be sufficient to protect the RPE cells from complement mediated attack or a state of chronic inflammation, such as occurs with AMD. Without being limited by any particular theory or mechanism of action, it is here envisioned that increasing the expression of CD46 in RPE cells by contact with CD46 or a source of CD46 protein restores the balance between alternative complement activation and regulation in AMD patients.

A novel murine model of complement activation using C3 to determine the capacity for adenoviral delivery of a human complement regulator to protect against human MAC deposition is shown in Examples herein. See also Ramo, K., S. M. Cashman, and R. Kumar-Singh, Invest Ophthalmol Vis Sci, 2008. 49(9): p. 4126-4136, hereby incorporated herein by reference. This and other humanized murine models provide convenient platforms to evaluate the role of CD46 protein, CD55 protein and STAC protein in the murine retina. Data herein show that complement activation occurred primarily through the alternative pathway and that human CD46 protected murine RPE cells from alternative pathway mediated complement attack.

Recent evidence has indicated that increased activity of the complement system plays a significant role in the pathogenesis of AMD. Further evidence includes the presence of fragments of the complement cascade closely associated with drusen (Hageman et al. 2001 Prog Retin Eye Res 20(6)705-732) or presence of MAC on the surface of RPE and choroidal blood vessels (Anderson et al. 2002 Am J Ophthalmol 134(3) 411-31. Genetic studies have identified polymorphisms in complement genes of both alternative and classical pathways, including Factor H, Factor B, C2 and C3 (Reynolds et al. 2009 Invest Ophthalmol Vis Sci, 50(12): 5818-5827). The most significant risk of developing AMD, however, is associated with polymorphisms in the alternative pathway regulator factor H (Edwards et al. 2005 Science 308(5720): 421-424). As the complement cascade is an important first line of defense for the immune system, a regulator such as CD46 that functions locally in ocular tissues and would dampen the alternative pathway which is the portion of the complement cascade that has been implicated as being over-active in this disease was analyzed in Examples herein.

Data herein show that CD46 despite robust expression on the membrane of mouse hepatocytes transduced with a CD46-expressing adenovirus vector, displayed no inhibition of complement-mediated cell lysis conferred in the presence of all pathways, and offered 39±0.88% protection against lysis that was specifically mediated by the alternative pathway. Without being limited by any particular theory or mechanism of action, it is here envisioned that CD46 has a higher binding affinity for proteins of the alternative pathway component C3b relative to the classical component C4b. It may take longer for CD46 to cleave C3b and C4b than does a regulator such as CD59 to disrupt the MAC complex due to requirement of CD46 as a co-factor for cleavage, requiring binding of the serine protease factor I to cleave C3b and C4b. Therefore, limiting the process of MAC deposition to the alternative pathway allows enough time for CD46 to bind C3b and recruit factor I before the convertase is formed. Furthermore, after the convertase is fainted, CD46 no longer binds to either C3b or C4b (Gao et al. 2009 BMC Cancer 9: 384; Brodbeck et al. 2000 J Immunol 165(7): 3999-4006), so that once convertase has assembled on the cell membrane, the rate of C3 cleavage is rapid and the amount of C3b exceeds that of CD46.

Figure 14A:
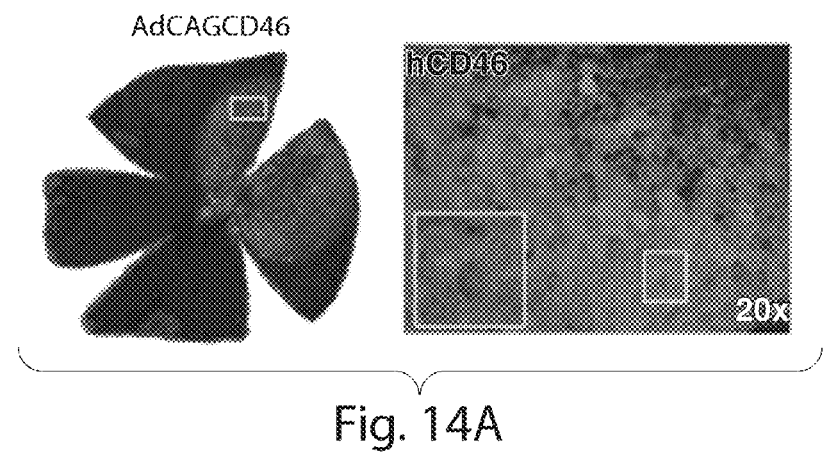
FIG. 14 panels A-B are a set of photomicrographs showing that hCD46 was expressed on mouse RPE cells following a sub-retinal injection of AdCAGCD46. Eight days after injection with AdCAGCD46, subjects were sacrificed and the lens, cornea and retina were removed from the eye to expose the RPE cells. Control subjects received no adenovirus vector injection. The eyecups were incubated in rate anti-mouse emmprin and NHS containing calcium and magnesium. Tissues were visualized with BF and stained with an antibody specific for human CD46.
Figure 14B:
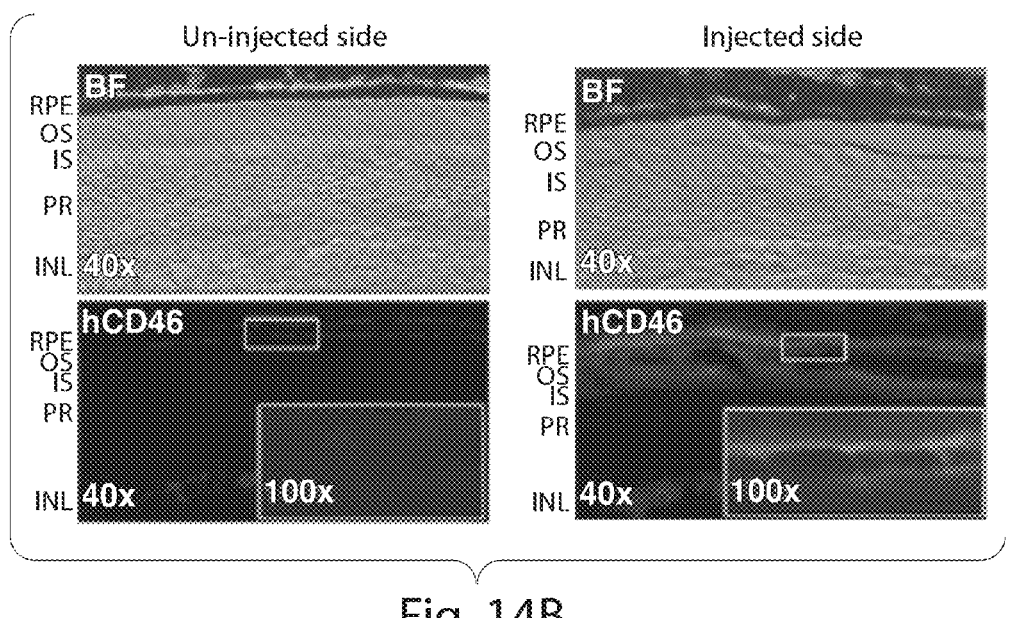
Figure 15A:
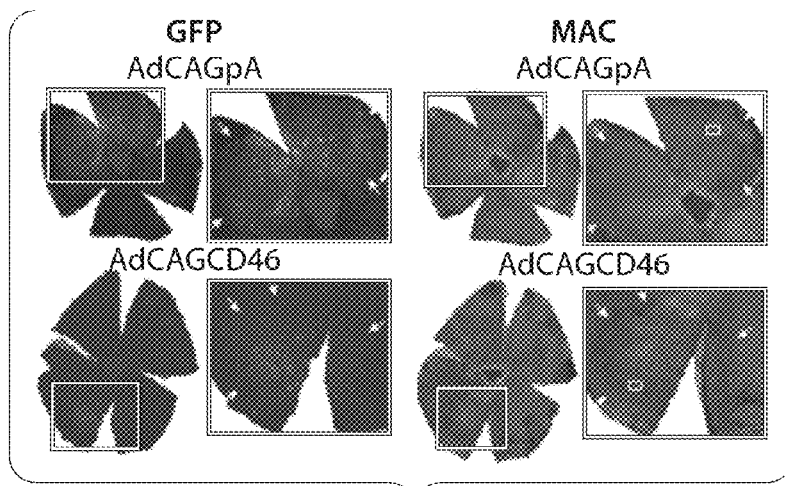
FIG. 15 panels A-D a bar graph and a set of photomicrographs showing that sub-retinal delivery of AdCAGCD46 reduced the amount of alternative pathway-mediated MAC deposition on RPE cells. Murine eyes were injected with either a mixture of AdCAGpA and AdCAGGFP (9:1 ratio) or a mixture of AdCAGCD46/AdCAGGFP (9:1 ratio) and the eyes were then visualized for GFP fluorescence and stained for expression of MAC. AdCAGGFP was included in each mixture to facilitate visualization of the injection site.
Figure 15B:
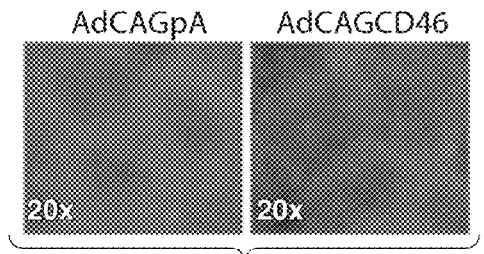
Figure 15C:
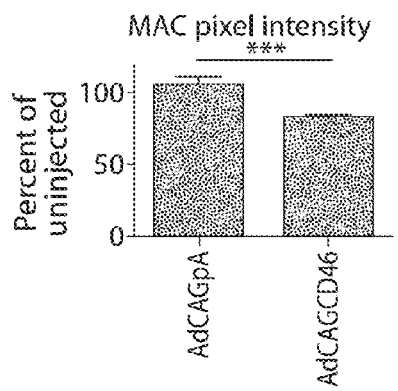
Figure 15D:
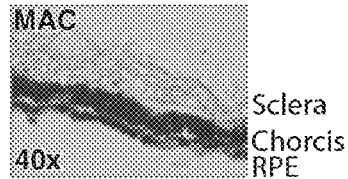

CD46 in human retinal tissue is localized to the basal and lateral surface of RPE cells (Vogt et al. 2006 Exp Eye Res 83(4): 834-840). This places CD46 close to the site of complement activation in AMD patients in which MAC deposition has been observed in RPE cells, drusen, and choroidal endothelial cells. Also CD46 expression is reduced on the RPE of AMD patients. Polymorphisms in CD46 have been linked to the kidney disease aHUS (Richards et al. 2003 Proc Natl Acad Sci USA 100(22): 12966-12971), another disease resulting from over-activation in the alternative arm of complement (Kavanagh et al. 2008 Annu Rev Med 59: 293-309). Renal allographs, which provide wild type expression of CD46, have been a viable therapy for patients suffering from aHUS due to CD46 polymorphisms (Caprioli et al. 2006 Blood 108(4): 1267-1279; Kavanagh et al. 2006 Semin Thromb Hemost, 32(2): 155-159). Examples herein show that expression of CD46 from an engineered adenovirus vector in vivo in mice resulted in 24±4.5% protection against an acute insult from human complement attack mediated by the alternative pathway. FIG. 14 panels A-B show that CD46 is most abundantly localized to the basal surface of mouse RPE cells after injection of AdCAGCD46, with some expression also on the apical and lateral surfaces. This pattern of expression is normal for human RPE (Vogt et al. 2006 Exp Eye Res, 2006. 83(4): 834-840). The apical side of the RPE is exposed directly to emmprin antibody and human serum in Examples herein such that MAC deposition and CD46 protection occurred almost exclusively on the apical surface. Further assays showed that CD46 blocked MAC deposition on the basal surface.

The strong linkage observed between polymorphisms in factor H and AMD prompt consideration of CD46 as a viable therapeutic option, as both proteins act at the same step of the complement cascade. CD46 in fact can compensate for the loss or reduction in factor H activity in human serum (Barilla-LaBarca, M. L., et al., J Immunol, 2002. 168(12): 6298-6304), a situation analogous to that proposed for AMD patients with factor H polymorphisms.

Data in Examples herein show that CD46 compositions including a STAC protein that includes amino acid sequences of CD46 protein are useful to treat ocular diseases including macular degeneration, by inhibiting MAC deposition and preventing lysis of retina cells. The phrase "ocular tissues" is used interchangeably with the phrase "ocular surfaces" and refers to any tissue or surface of the eye or the ocular mucosa. Examples of ocular tissues include retinal pigment epithelium, pupil, cornea, iris, lens, aqueous humor, retina, choroid, sclera, fovea, eye muscles such as ciliary muscles or orbital muscles, glands such as the lacrimal glands, and the conjunctiva.

In certain embodiments, the CD46 composition or STAC protein composition that includes amino acid sequences of CD46 protein provided used herein lacks the primary amino acid sequence for a functional hydrophobic transmembrane spanning domain. A functionally equivalent protein includes a modified hydrophobic transmembrane spanning domain amino acid sequence hence is defective in the ability to target a membrane. A sCD46 is an example of a recombinant membrane-independent CD46 (rmiCD46). Additional methods of obtaining membrane-independent CD46 include non-recombinant methods such as using an inhibitor of membrane association, for example, synthesizing CD46 in vivo or in vitro such that the transmembrane domain is lacking. Methods of obtaining the membrane-independent CD46 are shown in examples herein. Additional recombinant techniques for altering the nucleic acid sequence and amino acid sequence of a molecule are well known in the art of genetics and molecular biology.

In various embodiments, the composition includes a CD46 protein that includes a full length nucleic acid of CD46 that was recombinantly modified to remove the signal sequence for attachment of a hydrophobic transmembrane spanning domain. Alternatively the nucleic acid sequence of CD46 is modified by point mutations, substitutions or deletions to obtain a nucleic acid sequence that encodes an amino acid sequence that has a modified amino acid sequence at the a hydrophobic transmembrane spanning domain location, such that the protein is unable to attach to a membrane of a cell.

The term "membrane independent" as used herein refers to a CD46 amino acid sequence that lacks a a hydrophobic transmembrane spanning domain or has a modified a hydrophobic transmembrane spanning domain that lacks functional ability to bind to a cell membrane or a cell-membrane-associated structure such as a membrane-bound protein.

The CD46 protein herein is envisioned to include conservative sequence modifications. As used herein, the term "conservative sequence modifications" refers to amino acid modifications that do not significantly alter the characteristics of the CD46 protein or membrane-independent CD46 containing the amino acid sequence, i.e., amino acid sequences of CD46 that present amino acids having chemically-related side chains at the same relative positions and that will function in a manner similar to human CD46. Such conservative modifications include amino acid substitutions, additions and deletions. Modification of the amino acid sequence of CD46 is achieved using any known technique in the art e.g., site-directed mutagenesis or PCR based mutagenesis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

Conservative amino acid substitutions are changes in the CD46 protein in which an amino acid residue is replaced with a different amino acid residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine).

In certain embodiments, the CD46 amino acid sequence is substantially identical to that of the wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., *Nuc. Acids Research* 22:4673, 1994 (www.ebi.ac.uk/clustalw), BL2SEQ by Tatusova and Madden, *FEMS Microbiol. Lett.* 174:247, 1999 (www.ncbi.nlm.nih.gov/blast/bl2seq/bl2.html), SAGA by Notredame and Higgins, *Nuc. Acids Research* 24:1515, 1996 (igs-server.cnrs-mrs.fr/~cnotred), and DIALIGN by Morgenstern et al., *Bioinformatics* 14:290, 1998 (bibiserv.techfak.uni-bielefeld.de/dialign).

CD55

CD55 is known also as complement decay-accelerating factor or decay-accelerating factor (DAF), and is a protein complement regulator. See Lublin et al. 1989 Annu Rev Immunol 7: 35-58, Sims et al. U.S. Pat. No. 5,955,441 issued Sep. 21, 1999 and Martens et al. U.S. Pat. No. 7,008,775 issued Mar. 7, 2006, each of which is incorporated by reference herein in its entirety. CD55 is a glycosyl phosphatidyl inositol (GPI)-anchored glycoprotein of molecular weight of approximately 70 kDa expressed on the plasma membrane of all cell types that come into contact with plasma complement proteins. The protein is a constituent of the extracellular matrix. The human gene has been cloned (Medof et al 1987 Proc. Natl. Acad. Sci. USA, 84: 2007-2011) and the protein shares amino acid repeat motifs and functional similarities with other complement proteins. A variety of splice variants that are expressed in almost all tissues tested and vary in their expression patterns have been reported (Osuka et al 2006 Clin Cancer Res 12: 6367-6372). CD55 variants include soluble forms of CD55 secreted after glycosylation.

The human CD55 protein is uniformly GPI-anchored, which is referred to as DAF-GPI or GPI-DAF or CD55a. Mice possess two closely related genes, termed decay-accelerating factor 1 (DAF1) and decay-accelerating factor 2 (DAF2), also referred to as CD55b. The genes encoding Cd55a and CD55b share 93% identity in their coding regions. See Clift et al. 2009 Journal of Reproductive Immunology Vol. 81(1): 62-73; and Yamada et al. 2004 The Journal of Immunology vol. 172 (6): 3869-3875.

The term "membrane independent CD55" as used herein refers to a CD55 amino acid sequence that lacks a GPI anchor or has a modified GPI anchor that lacks function and ability to bind to a cell membrane or a cell-membrane-associated structure such as a membrane-bound protein. The CD55 protein herein used to engineer the CD55 composition or STAC protein composition including CD55 protein is envisioned to include conservative sequence modifications including deletions, substitutions, and additions as has been described herein.

Inflammatory processes and specifically activated complement has been implicated in the pathogenesis of a number of diseases including Alzheimer's disease (Tenner et al. 2001 Neurobiol Aging 22: 849-861), atherosclerosis (Niculescu et al. 2004 Immunol Res 2004 30: 73-80), and glomerular basement membrane kidney disease (Fang et al. 2008 Blood 111: 624-632; and Licht et al. 2009 Thromb Haemost 101: 271-278). A role for complement has been recently established in the pathogenesis of AMD. Consequently, a number of phase I/II clinical trials aimed at attenuating complement activation in AMD patients have recently been initiated. These trials target either C3 (compstatin/POT-4 peptide), C5 (eculizumab antibody, ARC 1905 aptamer), or Factor D (TNX-234 antibody). See Gehrs et al. 2010 Arch Ophthalmol 128: 349-358; and Ricklin et al. Nat Biotechnol 25: 1265-1275).

Compositions, methods and kits using CD55 to attenuate complement activation by accelerating the concomitant decay of the classical and alternative C3 convertases on RPE cells of mice are developed. Without being limited by any particular theory or mechanism of action, it is here envisioned that a perturbation upstream in complement activation through C3 convertase activity using CD55 significantly altered levels of MAC assembled in the terminal pathway. As MAC is a major component of complement-mediated cellular damage, levels of MAC deposition on RPE cell surfaces, a tissue intimately involved in AMD pathogenesis, were quantified. Examples herein show that expression of hCD55 mediated reduction of MAC deposition on ocular tissues.

Limited data on the localization of the different complement regulators in the human retina exists. However, previous studies have indicated that the complement regulators hCD55 and hCD59 are found primarily in the inner retina, whereas hCD46 is present exclusively in a polarized fashion on the RPE (Vogt et al. 2006 Exp Eye Res 83: 834-840). Further Y402H variant of factor H that is associated with AMD decreased binding of factor H to the RPE, ultimately leading to reduced protection of these cells from complement-mediated attack (Skerka et al. 2007 Mol Immunol 44: 3398-3406)

Increased RPE resistance to MAC-mediated damage is shown in Examples herein to result from increasing the cell surface levels of complement regulator hCD55 protein. Phase I clinical trials of adenoviral vector-mediated ocular gene transfer for the treatment of ocular disorders such as AMD4 (Campochiaro et al. 2006 Hum Gene Ther 17: 167-176) and vitreous tumor seeding from retinoblastoma (Chevez-Barrios et al. 2005 J Clin Oncol 23: 7927-7935) have demonstrated that intraocular injections of adenoviral vectors is a safe and well-tolerated approach. Adenovirus vectors are engineered to express transgenes for extended periods of up to 1 year— the longest time period examined (Kim et al. 2001 Proc Natl Acad Sci USA 98:13282-13287; Kreppel et al. 2002 Invest Ophthalmol Vis Sci 43: 1965-1970; and Lamartina et al. 2007 J Gene Med 9: 862-874). Thus adenovirus vectors carrying a gene encoding CD55 as described herein are able to provide long-term expression of the protein on ocular tissues including the RPE, a tissue where CD55 is not normally found at high levels.

Cross-species differences exist in some complement proteins as well as key differences between the complement system of humans and rodents limit testing the efficacy of human complement regulatory proteins in non-human systems (Kim et al. 2006 Clin Immunol 118: 127-136) Humans for example have one CD55 gene, mice have two, CD55a, CD55b (Post et al. 1990 J Immunol 144: 740-744), similarly humans have one CD59 gene, mice contain two, CD59a, CD59b (Powell et al. 1997 J Immunol 158: 1692-1702; and Qian et al. 2000 J Immunol 165: 2528-2534). CD55b and CD59b are exclusively expressed in the mouse testis whereas CD55a and CD59a are expressed broadly. Accordingly, Examples herein show that adenovirus-mediated delivery of hCD55 to murine RPE protects those cells against human complement mediated lysis and MAC formation. The protection conferred by attenuating the C3 convertases through hCD55 was as potent an approach as blocking the assembly of MAC directly on the cell surface via the expression of hCD59.

An aspect of the invention herein provides a method for treating AMD in a subject, the method involving contacting retinal pigment epithelium (RPE) of the subject with a CD55 protein composition, in which the retina is treated for AMD.

In related embodiments of the method, contacting the RPE is delivering at least one composition selected from the group consisting of: a nucleic acid vector with a gene encoding CD55 protein; CD55 protein; or CD55 expressed directly from naked nucleic acid.

In related embodiments of any of the above methods, the vector is a viral vector or a plasmid; for example, the viral vector is derived from a genetically engineered genome of at least one virus selected from the group consisting of adenovirus, adeno-associated virus, a herpesvirus, and a lentivirus. For example, the lentivirus is a retrovirus.

In various embodiments of the method, delivery of protein or nucleic acid is by at least one injection route selected from the group consisting of intravenous, intra-ocular, intra-muscular, subcutaneous, and intraperitoneal. In an embodiment of the method, the macular degeneration is dry.

An aspect of the invention provides a method of assaying extent of human MD in a model cell system or a method in a model cell system of assaying a serum complement component for prognosis or diagnosis of macular degeneration (MD), the method including: exposing a first sample of cells to serum and measuring resulting lysis, and comparing extent of lysis to that in a second sample of control cells not so exposed to serum, such that the extent of lysis in the first sample compared to that in the second sample is a measure of complement-induced MD.

An aspect of the invention provides a method of assaying in a model cell system potential therapeutic agents for human MD, the method including: contacting a first sample of cells to serum and measuring resulting lysis, and contacting a second sample of otherwise identical control cells with serum and a source of human CD55 and measuring resulting lysis; and contacting at least a third sample of cells to a candidate therapeutic composition and otherwise identically to serum, such that the extent of lysis of the third sample compared to that in the first and second sample is a measure of protection by the candidate composition, thereby providing the method of assaying for potential therapeutic agents.

A related embodiment of the above methods further includes contacting cells or tissues with a recombinant vector having a gene capable of expressing CD55. Lysis is measured for example by propidium iodide uptake and cell sorting. In a related embodiment of the above methods, the cells are hepatocytes. In related embodiments the cells are of murine origin. In a related embodiment of the above methods, the source of CD55 is human. In a related embodiment of the above methods the serum is normal human serum. Alternatively, the serum is from a diseased subject, for example, the diseased subject has MD.

An aspect of the invention provides a method of diagnosing or prognosing presence or progression of macular degeneration, the method including determining extent of membrane attack complex (MAC) deposition on retina. In a related embodiment of the method, determining extent of MAC deposition is analyzing by immunohistochemistry with antibodies that are specific for human MAC.

An aspect of the invention provides a pharmaceutical composition for treating macular degeneration including CD55 protein or a source of expression of CD55 protein in vivo, in which the composition is formulated for ocular delivery, in a dose effective to treat macular degeneration. In various related embodiments of the composition, the CD55 protein or source of expression of CD55 protein is at least one selected from the group consisting of: a nucleic acid vector with a gene encoding CD55 protein; a viral vector with a gene encoding CD55 protein; and a CD55 protein.

In related embodiments of the composition, the composition formulated for ocular delivery is at least one selected from the group consisting of: injection, eye drop, and ointment. In a related embodiment of the composition, injection is at least one selected from the group consisting of: intraocular injection, subconjunctival injection, and subtenon injection. In a related embodiment, the composition further includes at least one drug selected from the group consisting of: anti-tumor, antiviral, antibacterial, anti-mycobacterial, anti-fungal, anti-proliferative and anti-apoptotic. In a related embodiment, the CD55 protein is expressed as a soluble protein. In a related embodiment, the CD55 protein has a deletion encoding a glycosyl phosphatidyl inositol (GPI) anchoring domain.

An aspect of the invention provides a kit for assaying MAC deposition on ocular tissue or cells and for screening agents that inhibit deposition, the kit includes anti-MAC antibody, a container, and instructions for use with normal human serum. In a related embodiment, the kit further includes anti-emmprin antibody and/or normal human serum. In another related embodiment, the kit further includes CD55 protein as a positive control and the CD55 protein is a soluble form or a membrane-bound form, the latter for example embedded in a liposome preparation. In other related embodiments of the kit, at least one of the antibody, the serum, and the CD55 protein is a lyophil.

An aspect of the invention provides a method in a model cell system of assaying a serum complement component for prognosis or diagnosis of macular degeneration (MD), the method including: contacting detectably labeled cells with serum from a subject and measuring amount of extracellular and/or intracellular detectable agent for contacted cells; and comparing extracellular and/or intracellular agent in the cells to that in detectably labeled control cells not exposed to the serum and otherwise identical, such that amount of extracellular and/or intracellular agent in the contacted cells is compared to that in the control cells, such that a greater amount of extracellular detectably labeled agent in cells contacted with serum compared to the control cells is an indication of prognosis or diagnosis of MD.

An aspect of the invention provides a method of assaying in a model cell system a potential therapeutic agent for efficacy in treatment of human macular degeneration (MD), the method including: contacting a first sample of detectably labeled cells with serum from a subject and measuring amount of extracellular and/or intracellular detectable agent, and contacting a second sample of otherwise identical detectably labeled control cells with serum and a source of human CD55 protein and measuring amount of extracellular and/or intracellular detectable agent; and contacting at least a third sample of detectably labeled cells to at least one candidate therapeutic composition and otherwise identically to serum and measuring amount of extracellular and/or intracellular detectable agent, such that the amount of extracellular and/or intracellular detectable agent of the third sample compared to that in the first sample and the second sample is a measure of protection by the candidate composition, such that a greater amount of extracellular detectably labeled agent is an indication of MD, thereby assaying for a potential therapeutic agent for efficacy in treatment of human MD.

In various embodiments of the above methods, the detectable agent is at least one composition selected from the group consisting of a recombinant vector having a gene capable of expressing a detectable protein, a fluorescent agent, a colorimetric agent, an enzymatic agent, and a radioactive agent. For example, the detectable protein is at least one fluorescent protein selected from the group consisting: green fluorescent protein, aequorin, cyan fluorescent protein, DsRed fluorescent protein, enhanced green fluorescent protein, and yellow fluorescent protein. In other embodiments, the detectable agent is not a protein, for example, the detectable agent is at least one fluorescent agent selected from the group consisting of: Indocyanine Green, Doxorubicin, Riboflavin, Chlorophyll, and Porphyrin. In other embodiments, the detectable protein is enzyme, for example, β-galactosidase or alkaline phosphatase.

In embodiments of the above methods, the cells are hepatocytes. In embodiments of the above methods, the source of CD55 protein is human. In certain embodiments of the above methods, the serum is normal human serum. Alternatively, the serum is from a diseased subject. In general, the subject is in need of diagnosis or prognosis of MD. In other embodiments, the CD55 protein is soluble. In other embodiments the protein is membrane-bound.

STAC Protein

Previously a membrane bound CD59 was observed to protect cells from complement-mediated disease, however the site of expression of the regulator, yielded only a "patch" of protection in the ocular tissue such as the RPE. Thus, a secreted regulator of CD59 (sCD59 or rmiCD59) is here engineered, which was capable of diffusing through the retina and offer protection to the entire affected region (Kumar-Singh international application PCT/US09/00947 filed Feb. 13, 2009 which is hereby incorporated by herein in its entirety).

Soluble sCD59 was previously considered an inefficient regulator of complement in vivo unless it was fused with a membrane targeting moiety (Mizuno et al. 2001 Arthritis Rheum 44: 2425-2434; Bora 2010 J Biol Chem 285: 33826-33833; Song et al. 2003 J Clin Invest 111: 1875-1885; and Zhang et al. 1999 J Clin Invest 103: 55-61). However, recent data show that a membrane-independent sCD59 expressed in vivo in murine ocular tissue via an adenovirus or AAV vector significantly reduced MAC deposition and laser-induced choroidal neovascularization in a mouse model of neovascular AMD (Cashman et al. 2011 A Non Membrane-Targeted Human Soluble CD59 Attenuates Choroidal Neovascularization in a Model of Age Related Macular Degeneration PLoS ONE 6(4): e19078, which is hereby incorporated by reference in its entirety). Adenovirus-delivered sCD59 was observed to inhibit human MAC deposition even on murine liver vasculature.

Without being limited by any particular theory or mechanism of action, it is here envisioned that a recombinant fusion protein containing at least two of CD59 protein, CD46 protein and CD55 protein is a potent regulator of a number of complement pathways and proteins. Examples herein provi methods for engineering a novel chimeric soluble terminator of activated complement (STAC) having small functional units of each of CD46 protein, CD55 protein, and CD59 protein that are effective for treating complement-related conditions by modulating the complement cascade, and provide the composition. The resulting STAC protein composition includes functional units of CD46 protein, CD55 protein, and CD59 protein that in certain embodiments are operably linked. For example, the functional units are connected by amino acid linkers that do not affect the function of the components or the structural stability of the protein. Furthermore, the protein in certain embodiments is mutated to remove or delete a sequence encoding a protein membrane anchor. In a related embodiment, an exemplary STAC protein includes a secretory signal at the N-terminus. The STAC protein is approximately 130 KDa and was obtained retaining only the units/domains of each component protein that are involved in complement regulation. Other soluble complement regulators such as factor H (150 kDa) and sCR1 (200 kDa) are larger, and these have been used to regulate complement (Ripoche et al. 1984 Biochem J 221: 89-96; and Yoon et al. 1985 J Immunol 134: 3332-3338).

The recombinant STAC protein engineered herein is differs from naturally occurring regulators because it includes multiple complement regulatory domains from different combinations of CD59, CD46, and CD55 proteins and is membrane independent. Hence STAC protein is capable of diffusing and blanketing a large group of affected cells or tissue for treatment after a single administration at one time. For example the STAC protein includes an amino acid sequence from at least two of a CD46 protein, a CD55 protein, and a CD59 protein. For example, the STAC protein includes at least one of: the CD46 protein and the CD59 protein, the CD46 protein and the CD55 protein, and the CD55 protein and the CD59 protein. Alternatively, the STAC protein includes each of CD59 protein, CD46 protein and CD55 protein, operably linked and expressed for example in a soluble form. In various embodiments, the CD46 protein, the CD55 protein, and the CD59 protein are derived from mammalian proteins (e.g., human, mouse, and rabbit). For example the STAC protein comprises a CD46 protein and a CD59 protein that are human proteins and a CD55 protein that is a murine protein, or comprises each of CD46, CD55, and CD59 that are human proteins. Thus in various embodiments the STAC protein comprises proteins that are from the same mammal type, or from different types of mammals.

Without being limited by any particular theory or mechanism of action, it is here envisioned that the STAC protein synergistically blocks complement activation at mutiple steps in the complement pathway, including each of the complement pathways regulated by each of CD59 protein, CD46 protein, and CD55 protein. The STAC protein is shown in Examples herein to inhibit MAC deposition in vivo when delivered by an adenovirus vector, and is therefore potentially effective as an anti-complement therapy for treating or even preventing complement-associated diseases or conditions.

In various embodiments, the STAC protein or composition includes a CD46 protein encoded by a full length nucleic acid of CD46 which was modified to remove the amino acid sequences for signal sequence and hydrophobic transmembrane spanning domains. Alternatively the nucleic acid sequence of CD46 protein is modified by point mutations, substitutions or deletions to obtain a nucleic acid sequence that encodes a modified amino acid sequence with the modification located in the hydrophobic transmembrane spanning domain, such that the resulting protein fails to attach to cell membranes.

The term "membrane independent CD46" as used herein refers to a CD46 amino acid sequence that lacks a hydrophobic transmembrane spanning domain or has a modified hydrophobic transmembrane spanning domain that lacks functional ability to bind to a cell membrane or a cell-membrane-associated structure such as a membrane-bound protein. The scope of the CD46 protein herein is envisioned to include conservative sequence modifications including deletions, substitutions, and additions as has been described herein.

As used herein, the term "conservative sequence modifications" refers to amino acid modifications that do not significantly affect or alter the characteristics of the CD46 protein containing the amino acid sequence, i.e., amino acid sequences of CD46 protein that present these side chains at the same relative positions will function in a manner similar to human CD46 protein. Such conservative modifications include amino acid substitutions, additions and deletions. Modification of the amino acid sequence of CD46 protein is achieved using any known technique in the art e.g., site-directed mutagenesis or PCR based mutagenisis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the CD46 amino acid sequence is an amino acid sequence that is substantially identical to that of the wild type sequence. The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60% identity, or at least 75%, 85%, 95%, 96%, 98%, or 99% identity.

In various embodiments, the STAC protein or composition includes a CD55 protein and/or a CD59 protein. In various embodiments, the CD55 protein includes a full length nucleic acid of CD55. Alternatively, the CD55 protein is a portion or homologue of full length nucleic acid sequence or amino acid sequence as described herein. In certain embodiments, the CD55 protein includes conservative sequence modifications CD59 protein.

Mature human CD59 protein is composed of 77 amino acids and has a molecular weight of about 18 kD to about 21 kD. Precursor human CD59 protein includes an amino-terminal signal peptide of 25 amino acids and a carboxyl-terminal peptide of 26 amino acids which allows for attachment of a membrane anchor. Amino acid sequences of precursor human CD59 protein, a mature human CD59 protein, and CD59 protein of other mammals, e.g., baboon, African green monkey, owl monkey, marmoset, HVS-15, pig, rabbit, rat, and mouse, are shown in Sims et al. U.S. Pat. No. 7,166,568 issued Jan. 23, 2007 which is incorporated herein by reference in its entirety.

The protein structure of CD59 is characterized as a single cysteine-rich domain, having a hydrophobic core with three loops and a small fourth helical loop (Yu et al., Journal of Experimental Medicine, 185(4):745-753, 1997). Disulfide-bonded cysteine pairs connect each of these loops (Yu et al., 1997).

The structure of the gene encoding CD59 has been characterized (Fodor et al. U.S. Pat. No. 5,624,837, issued Apr. 29, 1997). The gene is located on the short arm of chromosome 11 in humans, specifically chromosome 11p13 and 11p14 (On-line Mendelian Inheritance in Man accession number and 107271), and consists of 4 exons spanning 20 kb (Petranka et al. Proc. Nat. Acad. Sci. 89:7876-7879, 1992). An untranslated first exon is preceded by a G and C-rich promoter region that lacks a consensus TATA or CAAT motif. The second exon encodes the hydrophobic leader sequence of the protein, and the third exon encodes the N-terminal portion of the mature protein. The fourth exon encodes the remainder of the mature protein, including the hydrophobic sequence for glycophosphoinosital anchor attachment to a cell membrane.

CD59 is a glycosylphosphatidylinositol-anchored glycoprotein that is expressed on human peripheral blood leukocytes, erythrocytes, and many cell lines. The protein is expressed on both hematopoietic and non-hematopoietic non-hemopoietic cells, for example on endothelial cells, peripheral nerve fibers, neurons, microglia, oligodendrocytes, astrocytes, ependymal cells, epithelial cells, acinar cells of the salivary glands, bronchial epithelium, renal tubules and squamous epithelium. See Nose, M. et al. 1990 Immunology 70(2): 145-149; Vedeler, C. et al. 1994 Immunology 82(4): 542-547; and Hidestima, T. et al. 1990 Immunology 69(3): 396:401. A cDNA encoding CD59 was reported by Sawada, R. et al. 1989 Nucleic Acids Res 17(16) 6728. cDNA encoding CD59 has also been cloned from human T-cell leukemia (YT) and human erythroleukemia (K562) cell lines, and CD59 has been transiently expressed in COS cells (Walsh, L.A. et al. 1990 Eur J. 1 mmol 21(3): 847-850). Human CD59 is encoded by a nucleic acid sequence including 26 amino acids located at the C terminus, which contains a signal sequence for attachment of a GPI anchor at amino acid asparagine at position 77. The amino acid sequence of full length cDNA of CD59 is shown in Fodor et al., U.S. Pat. No. 5,624,837 issued Apr. 29, 1997.

Analysis of the physical association of CD59 with components of MAC show that separate binding sites for CD59 are contained within the α-chains of each of human C8 and human C9 (See Kimberley et al. 2007 Mol Immunol 44: 73-81). The binding site for interactions of human CD59 with human C9 has been identified as amino acid residues 42 to 58 in the sequence of mature human CD59, that bind to the region of human C9 corresponding to human amino acid residues 334 to 418 of that protein, more particularly human C9 amino acid residues 359 to 384, immediately C-terminal to the predicted membrane-inserting domain of C9 (Sims et al. PCT/US96/17940 filed Nov. 8, 1996, which is incorporated herein by reference in its entirety).

The active surface exposed amino acid residue side chains that are available to bind C8/C9, identified from solution structure of mature human CD59 from published NMR data and the knowledge of the active portion of the CD59 molecule, are histidine at position 44, asparagine at position 48, aspartic acid at position 49, threonine at positions 51 and 52, arginine at position 55, and glutamic acid at position 58. NMR structures for CD59 are described in deposits by Kieffer et al., Human Complement Regulatory Protein CD59 (Extracellular Region, Residues 1 70; NMR, 10 Structures), MMDB Id: 891, PDB Id: 1ERH; Kieffer et al., Human Complement Regulatory Protein CD59 (Extracellular Region, Residues 1 70; NMR, Restrained), MMDB Id: 890, PDB Id: 1ERG; Fletcher et al., CD59 Complexed With Glcnac-Beta-1,4-(Fuc-Alpha-1,6)-Glcnac-Beta-1 (NMR, 10 Structures), MMDB Id: 498, PDB Id: 1CDS; Fletcher et al., CD59 Complexed With Glcnac-Beta -1,4-Glcnac-Beta-1 (NMR, 10 Structures), MMDB Id: 497, PDB Id: 1CDR. The 1CDS and 1CDR deposits by Fletcher et al. Amino acid sequences of CD59 that present these side chains at the same relative positions function in a manner similar to human CD59 (Sims et al.), and such variants are within the scope of the methods, kits and pharmaceutical compositions herein.

A CD59 protein in certain embodiments used in construction of the STAC protein herein lacks the primary amino acid sequence for a functional GPI anchor. A functional equivalent protein includes a modified GPI anchor domain amino acid sequence that is functionally defective and lacks the ability to target a membrane. Additional methods of obtaining a STAC protein having a membrane-independent CD59 protein include non-recombinant methods such as providing an inhibitor of membrane association, for example, synthesizing CD59 in vivo or in vitro such that the GPI anchor is lacking. Methods of obtaining the membrane-independent CD59 are shown in examples herein. Additional recombinant techniques for altering the nucleic acid sequence and amino acid sequence of a molecule are well known in the art of genetics and molecular biology.

In various embodiments, the composition includes an amino acid sequence of a CD59 protein having a full length nucleic acid of CD59 protein that was modified to remove the signal sequence for attachment of the GPI anchor at the nucleotides encoding amino acid asparagine at position 77. Alternatively the nucleic acid sequence of CD59 is modified by one or more point mutations, substitutions or deletions to obtain a nucleic acid sequence that encodes an amino acid sequence that has a modified amino acid sequence at the GPI anchor location, such that the protein is unable to attach to a membrane of a cell. The term "membrane independent CD59" as used herein refers to a CD59 amino acid sequence that lacks a GPI anchor or has a modified GPI anchor that lacks function and ability to bind to a cell membrane or a cell-membrane-associated structure such as a membrane-bound protein.

GPI anchoring involves a multi-step pathway in the endoplasmic reticulum including the interaction of numerous gene products. Many proteins including CD59 require GPI to be expressed at the cell surface and to function effectively. The mechanism by which structure in a protein signal encodes for attachment of GPI anchors is reviewed by Orlean, P. et al. 2007 JLR 48:993-1011. GPI attachment generally involves an amino acid sequence that contains: a hydrophobic N-terminal secretion signal that targets the protein to the ER, and a C-terminal GPI signal anchor sequence. The amino acid to which the GPI becomes linked is referred to as the omega (ω) residue, with amino acids N-terminal to the omega residue referred to as omega-minus (ω−) and with amino acids C-terminal to the omega residue referred to as omega-plus (ω+). The GPI anchor sequence includes a stretch of about ten polar amino acids (i.e., ω-10 to ω-1), for example arginine, lysine, aspartate, glutamate, asparagine, or glutamate, that form a flexible linker region. The ω residue has been observed to be one of glycine, alanine, serine, asparagine, aspartic acid, or cysteine. Mutation including substitution and deletion of nucleic acids encoding amino acids at omega positions are used to reduce or eliminate the attachment of the GPI anchor or reduce or eliminate the effective functionality of the GPI anchor. For example, such a variation includes substituting the nucleic acids encoding hydrophobic leucine (e.g., nucleic acids CTG) and alanine (e.g., nucleic acids GCA) with nucleic acids encoding glycine (e.g., nucleic acids CAG) and glutamate (e.g., nucleic acids GAA), which are less hydrophobic (i.e., more hydrophilic) amino acids. Alternatively, a variation includes substituting the ω residue with another amino acid, for example substituting a glycine for a tyrosine.

In other portions of the protein not involved in GPI anchoring, the STAC protein herein includes amino acid sequences from a CD59 protein having conservative sequence modifications. As used herein, the term "conservative sequence modifications" refers to amino acid modifications that do not significantly affect or alter the characteristics of the CD59 protein or membrane-independent CD59 containing the amino acid sequence, i.e., amino acid sequences of CD59 that present these side chains at the same relative positions will function in a manner similar to human CD59. Such conservative modifications include amino acid substitutions, additions and deletions. Modification of the amino acid sequence of CD59 is achieved using any known technique in the art e.g., site-directed mutagenesis or PCR based mutagenesis. Such techniques are described in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989. Conservative amino acid substitutions are ones in which the amino acid residue is replaced with an amino acid residue having a similar side chain such as replacing a small amino acid with a different small amino acid, a hydrophilic amino acid with a different hydrophilic amino acid, etc.

Examples herein include methods, compositions and kits having a chimeric soluble terminator of activated complement (STAC) protein with amino acid sequences from each of a CD46 protein, a CD55 protein, and a CD59 protein, and a nucleic acid expressing the recombinant STAC protein, such that the STAC negatively modulates classical and alternative complement pathways and treats complement-related conditions. Alternatively, the STAC protein includes an amino acid sequences from at least two of a CD46 protein, a CD55 protein, and a CD59 protein. The phrase "complement-related" as used herein and in the claims includes without limitation "complement-associated", and refers to any cell or tissue that is affected by a complement pathway. Examples of complement-related disorders or conditions include macular degeneration, lupus nephritis, Sjögren's syndrome, organ graft rejection, asthma, and chronic obstructive pulmonary disease.

In various embodiments, the STAC protein composition has an amino acid sequence shown in SEQ ID NO: 1 or a portion thereof. Additional exemplary amino acid sequences are obtained by mutating the nucleic acid sequence encoding the STAC protein to obtain point mutations, substitutions or deletions having a nucleic acid sequence that encodes a modified amino acid sequence, encoding a protein that retains the binding and inhibitory functions and is thereby capable of treating or preventing a complement-related disorder or condition.

The STAC protein herein is envisioned to include conservative sequence modifications in residues of the protein or in residues modified by conservative amino acid changes that do not affect the therapeutic function resulting from inhibition of complement pathways, whether involved in binding the binding the protein to a target cell, a complement protein, a complement protein precursor, or involved in targeting in a complement pathway. As used herein, the term "conservative sequence modifications" refers to amino acid modifications that do not significantly affect or alter the functional characteristics of the protein. Such conservative modifications include amino acid substitutions, additions and deletions. Modification of the amino acid sequence of the STAC protein is achieved using any known technique in the art e.g., site-directed mutagenesis or PCR based mutagenesis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

Conservative amino acid substitutions are changes in the STAC protein in which an amino acid residue is replaced with a different amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

In certain embodiments, the amino acid sequence of the STAC protein is substantially identical to SEQ ID NO:1 or a portion. The term "substantially identical" is used herein to refer to a first amino acid sequence that contains a sufficient or minimum number of amino acid residues that are identical to aligned amino acid residues in a second amino acid sequence such that the first and second amino acid sequences can have common structural domains and/or common functional activities. For example, amino acid sequences that contain a common structural domain have at least about 30% identity, or at least 40%, 50%, 60%, 65%, 70%, 75%, 80%, 85%, 90%, 95%, 96%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap that is introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., *Nuc. Acids Research* 22:4673, 1994 (www.ebi.ac.uk/clustalw), BL2SEQ by Tatusova and Madden, *FEMS Microbiol. Lett.* 174:247, 1999 (www.ncbi.nlm.nih.gov/blast/b12seq/b12.html), SAGA by Notredame and Higgins, *Nuc. Acids Research* 24:1515, 1996 (igs-server.cnrs-mrs.fr/~enotred), and DIALIGN by Morgenstern et al., *Bioinformatics* 14:290, 1998 (bibiserv.techfak.uni-bielefeld.de/dialign).

Vectors

Methods herein for treating or preventing a complement-related disorder include contacting cells with a pharmaceutical composition including a C3 protein, a CD46 protein, a CD55 protein, or a STAC protein, which protein is recombinantly produced. The term "recombinant" refers to proteins produced by manipulation of genetically modified organisms, for example micro-organisms.

An exemplary source of the protein includes a polynucleotide sequence that encodes the protein, for example, a nucleotide sequence encoding the protein, or functional equivalent, is inserted into an appropriate expression vector, i.e., a vector that contains the necessary nucleic acid encoding elements that regulate transcription and translation of the inserted coding sequence, operably linked to the nucleotide sequence encoding the amino acid sequence of the recombinant protein.

Methods that are well known to those skilled in the art are used to construct expression vectors containing a sequence encoding a protein operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to carry and express a protein encoding sequence. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989.

Virus vectors include, but are not limited to, adenovirus vectors, lentivirus vectors, adeno-associated virus (AAV) vectors, and helper-dependent adenovirus vectors. For example, virus vectors deliver a nucleic acid sequence that encodes a STAC protein that as shown herein that treat complement-related conditions. Adenovirus packaging vectors are commercially available from American Type Tissue Culture Collection (Manassas, Va.). Methods of constructing adenovirus vectors and using adenovirus vectors are shown in Klein et al., Ophthalmology, 114:253-262, 2007 and van Leeuwen et al., Eur. J. Epidemiol., 18:845-854, 2003.

Adenovirus vectors have been used in eukaryotic gene expression (Levrero et al., Gene, 101:195-202, 1991) and vaccine development (Graham et al., Methods in Molecular Biology: Gene Transfer and Expression Protocols 7, (Murray, Ed.), Humana Press, Clifton, N.J., 109-128, 1991). Further, recombinant adenovirus vectors are used for gene therapy (Wu et al., U.S. Pat. No. 7,235,391).

Recombinant adenovirus vectors are generated, for example, from homologous recombination between a shuttle vector and a provirus vector (Wu et al., U.S. Pat. No. 7,235,391). The adenovirus vectors herein are replication defective, for example, are conditionally defective, lacking an adenovirus region, and a polynucleotide encoding a peptide or protein is introduced at the position from which the coding sequences have been removed. The polynucleotide encoding the gene of interest alternatively is inserted in the another region.

Helper cell lines may be derived from human cells, such as 293 human embryonic kidney cells, muscle cells, hematopoietic cells or other human embryonic mesenchymal or epithelial cells. Alternatively, the helper cells may be derived from the cells of other mammalian species that are permissive for human adenovirus, e.g., Vero cells or other monkey embryonic mesenchymal or epithelial cells. Generation and propagation of these replication defective adenovirus vectors using a helper cell line is described in Graham et al, J. Gen. Virol., 36:59-72, 1977.

Lentiviral vector packaging vectors are commercially available from Invitrogen Corporation (Carlsbad Calif.). An HIV-based packaging system for the production of lentiviral vectors is prepared using constructs in Naldini et al., Science 272: 263-267, 1996; Zufferey et al., Nature Biotechnol., 15: 871-875, 1997; and Dull et al., J. Virol. 72: 8463-8471, 1998.

A number of vector constructs are available to be packaged using a system, based on third-generation lentiviral SIN vector backbone (Dull et al., J. Virol. 72: 8463-8471, 1998). For example the vector construct pRRLsinCMVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the *Aequora* jellyfish GFP driven by the CMV promoter, and the woodchuck hepatitis virus PRE element, which appears to enhance nuclear export. The GFP marker gene allows quantitation of transfection or transduction efficiency by direct observation of UV fluorescence microscopy or flow cytometry (Kafri et al., Nature Genet., 17: 314-317, 1997 and Sakoda et al., J. Mol. Cell. Cardiol., 31: 2037-2047, 1999).

Manipulation of retroviral nucleic acids to construct a retroviral vector containing the gene that encodes for a peptide or protein and packaging cells is accomplished using techniques known in the art. See Ausubel, et al., 1992, Volume 1, Section III (units 9.10.1-9.14.3); Sambrook, et al., 1989. Molecular Cloning: A Laboratory Manual. Second Edition. Cold Spring Harbor Laboratory Press, Cold Spring Harbor, N.Y.; Miller, et al., Biotechniques. 7:981-990, 1989; Eglitis, et al., Biotechniques. 6:608-614, 1988; U.S. Pat. Nos. 4,650, 764, 4,861,719, 4,980,289, 5,122,767, and 5,124,263; and PCT patent publications numbers WO 85/05629, WO 89/07150, WO 90/02797, WO 90/02806, WO 90/13641, WO 92/05266, WO 92/07943, WO 92/14829, and WO 93/14188.

A retroviral vector is constructed and packaged into non-infectious transducing viral particles (virions) using an amphotropic packaging system. Examples of such packaging systems are found in, for example, Miller, et al., Mol. Cell. Biol. 6:2895-2902, 1986; Markowitz, et al., J. Virol. 62:1120-1124, 1988; Cosset, et al., J. Virol. 64:1070-1078, 1990; U.S. Pat. Nos. 4,650,764, 4,861,719, 4,980,289, 5,122,767, and 5,124,263, and PCT patent publications numbers WO 85/05629, WO 89/07150, WO 90/02797, WO 90/02806, WO 90/13641, WO 92/05266, WO 92/07943, WO 92/14829, and WO 93/14188.

Generation of "producer cells" is accomplished by introducing retroviral vectors into the packaging cells, a process of contacting referred to herein as "transducing", "transfecting", or "infecting". Examples of such retroviral vectors are found in, for example, Korman, et al., Proc. Natl. Acad. Sci. USA. 84:2150-2154, 1987; Morgenstern, et al., Nucleic Acids Res. 18:3587-3596, 1990; U.S. Pat. Nos. 4,405,712, 4,980,289, and 5,112,767; and PCT patent publications numbers WO 85/05629, WO 90/02797, and WO 92/07943.

Herpesvirus packaging vectors are commercially available from Invitrogen Corporation, (Carlsbad, Calif.). Exemplary herpesviruses are an α-herpesvirus, such as *Varicella-Zoster* virus or pseudorabies virus; a herpes simplex virus such as HSV-1 or HSV-2; and a herpesvirus such as Epstein-Barr virus. A method for preparing empty herpesvirus particles that can be packaged with a desired nucleotide segment, for example a nucleotide or polynucleotide sequence, in the absence of a helper virus that is capable to most herpesviruses is shown in Fraefel et al. (U.S. Pat. No. 5,998,208, issued Dec. 7, 1999).

The herpesvirus DNA vector can be constructed using techniques familiar to the skilled artisan. For example, DNA segments encoding the entire genome of a herpesvirus is divided among a number of vectors capable of carrying large DNA segments, e.g., cosmids (Evans, et al., Gene 79, 9-20, 1989), yeast artificial chromosomes (YACS) (Sambrook, J. et al., MOLECULAR CLONING: A LABORATORY MANUAL, 2nd Edition, Cold Spring Harbor Press, Cold Spring Harbor, N.Y., 1989) or *E. coli* F element plasmids (O'Conner, et al., Science 244:1307-1313, 1989).

For example, sets of cosmids have been isolated which contain overlapping clones that represent the entire genomes of a variety of herpesviruses including Epstein-Barr virus, Varicella-Zoster virus, pseudorabies virus and HSV-1. See M. van Zijl et al., J. Virol. 62, 2191, 1988; Cohen, et al., Proc. Nat'l Acad. Sci. U.S.A. 90, 7376, 1993; Tomkinson, et al., J. Virol. 67, 7298, 1993; and Cunningham et al., Virology 197, 116, 1993.

AAV is a dependent parvovirus in that it depends on co-infection with another virus (either adenovirus or a member of the herpes virus family) to undergo a productive infection in cultured cells (Muzyczka, Curr Top Microbiol Immunol, 158:97 129, 1992). For example, recombinant AAV (rAAV) virus is made by co-transfecting a plasmid containing the gene of interest, for example, the a gene of interest, flanked by the two AAV terminal repeats (McLaughlin et al., J. Virol., 62(6):1963 1973, 1988; Samulski et al., J. Virol, 63:3822 3828, 1989) and an expression plasmid containing the wild-type AAV coding sequences without the terminal repeats. Cells are also contacted or transfected with adenovirus or plasmids carrying the adenovirus genes required for AAV helper function. Recombinant AAV virus stocks made in such fashion include with adenovirus which must be physically separated from the recombinant AAV particles (for example, by cesium chloride density centrifugation).

Adeno-associated virus (AAV) packaging vectors are commercially available from GeneDetect (Auckland, New Zealand). AAV has been shown to have a high frequency of integration and infects non-dividing cells, thus making it useful for delivery of genes into mammalian cells in tissue culture (Muzyczka, Curr Top Microbiol Immunol, 158:97 129, 1992). AAV has a broad host range for infectivity (Tratschin et al., Mol. Cell. Biol., 4:2072 2081, 1984; Laughlin et al., J. Virol., 60(2):515 524, 1986; Lebkowski et al., Mol. Cell. Biol., 8(10):3988 3996, 1988; McLaughlin et al., J. Virol., 62(6):1963 1973, 1988).

Methods of constructing AAV vectors and using AAV vectors are described, for example in U.S. Pat. Nos. 5,139,941 and 4,797,368. Use of AAV in gene delivery is further described in LaFace et al., Virology, 162(2):483 486, 1988; Zhou et al., Exp. Hematol, 21:928 933, 1993; Flotte et al., Am. J. Respir. Cell Mol. Biol., 7(3):349 356, 1992; and Walsh et al., J. Clin. Invest, 94:1440 1448, 1994.

Recombinant AAV vectors have been used successfully for in vitro and in vivo transduction of marker genes (Kaplitt et al., Nat. Genet., 8(2):148 54, 1994; Lebkowski et al., Mol. Cell. Biol., 8(10):3988 3996, 1988; Samulski et al., EMBO J., 10:3941 3950, 1991; Shelling and Smith, Gene Therapy, 1: 165 169, 1994; Yoder et al., Blood, 82 (Supp.): 1:347 A, 1994; Zhou et al., Exp. Hematol, 21:928 933, 1993; Tratschin et al., Mol. Cell. Biol., 5:3258 3260, 1985; McLaughlin et al., J. Virol., 62(6):1963 1973, 1988) and transduction of genes involved in human diseases (Flotte et al., Am. J. Respir. Cell Mol. Biol., 7(3):349 356, 1992; Ohi et al., Gene, 89(2):279 282, 1990; Walsh et al., J. Clin. Invest, 94:1440 1448, 1994; and Wei et al., Gene Therapy, 1:261268, 1994).

In certain embodiments, the vectors herein are non-viral vectors for example synthetic gene delivery vehicles or vectors that are not related to a virus particle and that specifically deliver the gene material to the target cells or tissue. Examples of non-viral vectors include liposomes, peptides, nanoparticles, emulsions, or encapsulated two or more phase systems or other suitable preparation. Thus, in certain embodiments a method, kit, or composition involves a non-viral vector with nucleic acid that is loaded and contacted to a tissue or cell. For example a liposome containing naked DNA encoding a protein is encapsulated in the liposome and the liposome is contacted to the tissue or cell such that the nucleic acid is effectively delivered to the tissue or cell for treatment of a complement-related disease.

Pharmaceutical Compositions

An aspect of the present invention provides pharmaceutical compositions that include at least one of CD46 protein, a CD55 protein, and a STAC protein or a nucleic acid expressing the protein, for treating a complement-related disorder by negatively modulating complement proteins or pathways. In certain embodiments, the pharmaceutical composition is compounded for systemic delivery to a subject, for example the composition is formulated as an injection. The composition in another embodiment is formulated as an ophthalmologic formulation for administration to the eye and may be compounded for delivery to the fundus, or for release locally at the retina or otherwise formulated to provide effective treatment of the vessels and/or tissue involved in complement disorders negatively affecting the ocular tissues. In related embodiments, the pharmaceutical composition is formulated sufficiently pure for administration to a human subject, e.g., to the vascular system or endothelial system of a human subject. In certain embodiments, these compositions optionally further include one or more additional therapeutic agents.

In certain embodiments, the additional therapeutic agent or agents are selected from the group consisting of growth factors, anti-inflammatory agents, vasopressor agents including but not limited to nitric oxide and calcium channel blockers, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGFs), IGF binding proteins (IGFBPs), epidermal growth factor (EGF), platelet derived growth factor (PDGF), neu differentiation factor (NDF), hepatocyte growth factor (HGF), vascular endothelial growth factor (VEGF), heparin-binding EGF (HBEGF), thrombospondins, von Willebrand Factor-C, heparin and heparin sulfates, and hyaluronic acid.

In certain embodiments, a plurality of therapeutic agents are include in the pharmaceutical composition to treat the same, a concurrent or a related symptom, condition or disease. In some embodiments, the therapeutic agent is a drug that may include without limitation anti-coagulant, anti-tumor, anti-viral, anti-bacterial, anti-mycobacterial, anti-fungal, anti-proliferative or anti-apoptotic agents. Drugs that are included in the compositions of the invention are well known in the art. See for example, Goodman & Gilman's The Pharmacological Basis of Therapeutics, 9th Ed., Hardman, et al., eds., McGraw-Hill, 1996, the contents of which are herein incorporated by reference herein in their entireties.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, the choice of agents and non-irritating concentrations to be determined according to the judgment of the formulator.

Therapeutically Effective Dose

Methods provided herein involve contacting cells or tissues with a pharmaceutical composition, for example, administering a therapeutically effective amount of a pharmaceutical composition having as an active agent at least one of CD46 protein, CD55 protein, and STAC protein, a nucleic acid encoding a protein or a source of expression of the protein, to a subject in need thereof, in such amounts and for such time as is necessary to achieve the desired result including reduction or preventing of indicia of the complement-related condition.

The compositions, according to the method of the present invention, may be administered using any amount and any route of administration effective for treating the complement-related disorder. Thus, the expression "amount effective for treating a complement-related disease or condition", as used herein, refers to a sufficient amount of composition to beneficially prevent or ameliorate the symptoms of the disease or condition.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., intermediate or advanced stage of macular degeneration; age, weight and gender of the patient; diet, time and frequency of administration; route of administration; drug combinations; reaction sensitivities; and tolerance/response to therapy. Long acting pharmaceutical compositions might be administered hourly, twice hourly, every three to four hours, daily, twice daily, every three to four days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model and in vivo model provided herein are also used to achieve a desirable concentration and total dosing range and route of administration. Such information can then be used to determine useful doses and routes for administration in humans.

A therapeutically effective dose refers to that amount of active agent that ameliorates the symptoms or condition or prevents progression of the disease or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

The daily dosage of the products may be varied over a wide range, such as from 0.001 to 1000 mg per adult human per day. For ocular administration, the compositions are provided for example in the form of a solution containing 0.001, 0.01, 0.05, 0.1, 0.5, 1.0, 2.5, 5.0, 10.0, 15.0, 25.0, 50.0, 100.0, 250.0, or 500.0 micrograms of the active ingredient for the symptomatic adjustment of the dosage to the patient to be treated.

A unit dose typically contains from about 0.001 micrograms to about 500 micrograms of the active ingredient, preferably from about 0.1 micrograms to about 100 micrograms of active ingredient, more preferably from about 1.0 micrograms to about 10 micrograms of active ingredient. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day. The compositions may be administered on a regimen of, for example, one to four or more times per day. A unit dose may be divided for example, administered in two or more divided doses.

Administration of a source of expression of a protein is administration of a dose of a viral vector or a nucleic acid vector, for example the dose contains at least about 50, 100, 500, 1000, or at least about 5000 particles per cell to be treated. Alternatively, the dose of a viral vector or a nucleic acid vector is at least about $10^4$ to about $10^5$; about $10^5$ to about $10^6$; $10^6$ to about $10^7$; $10^7$ to about $10^8$; about $10^8$ to about $10^9$; about $10^9$ to about $10^{10}$; or at least about $10^{10}$ to about $10^{11}$. The dose effective for treating a cell number can be calculated from the area in need of treatment by methods known to one of skill in the art.

Administration of Pharmaceutical Compositions

As formulated with an appropriate pharmaceutically acceptable carrier in a desired dosage, the pharmaceutical composition provided herein is administered to humans and other mammals for example topically (as by powders, ointments, or drops), orally, rectally, mucosally, sublingually, parenterally, intracisternally, intravaginally, intraperitoneally, bucally, sublingually, ocularly, or intranasally, depending on preventive or therapeutic objectives and the severity and nature of a complement-related disorder or condition.

Injections include intravenous injection or intra-ocular injection into the aqueous or the vitreous humor, or injection into the external layers of the eye, such by subconjunctival injection or subtenon injection.

Liquid dosage forms for example for intravenous, ocular, mucosal, or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the eye and body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage fauns of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage fowls may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

The following examples and claims are illustrative only and not intended to be further limiting. Those skilled in the art will recognize or be able to ascertain using no more than routine experimentation, numerous equivalents to the specific procedures described herein. Such equivalents are within the scope of the present invention and claims. The contents of all references including issued patents and published patent applications cited in this application are hereby incorporated by reference.

EXAMPLES

Unless, indicated otherwise the following methods and materials were used in the Examples herein.

Example 1

Adenovirus Constructs Carrying a Nucleotide Sequence Encoding C3

An MluI fragment from pCMV-Sport6C3 (ATCC, Image clone ID 5134713; GenBank ID: BC043338; SEQ ID NO: 7) containing a murine C3 cDNA was cloned into the MluI site of pShCMVMCS (a modified version of pShuttle containing the CMV promoter, an SV40 intron and polyA and an MluI-inclusive multiple cloning site). The C3-containing pShuttle was then recombined with pAd-Easy1 and the rescued virus, AdCMVC3, was amplified (Cashman et al. 2002 Mol Ther 6: 813-823). A control virus, AdCMVGFP, that expresses GFP was constructed as described in Cashman et al. 2004 Virology 324: 129-139. For western blot analysis, human embryonic retinoblasts (HERs) were contacted with either AdCMVC3 or AdCMVGFP in Dulbecco's Modified Eagle's Medium supplemented with 2% fetal bovine serum (Invitrogen, Carlsbad, Calif.). Cell lysates and cell media were loaded on a 10% Tris-HCl gel (Bio-Rad Criterion). Membranes were probed with an anti-mouse C3 polyclonal antibody (1:1000; Cell Sciences, Canton, Mass.), followed by a 1:10,000 dilution of HRP-conjugated goat anti-rabbit. Immunocytochemistry was performed by infecting $1.2 \times 10^6$ HERs at an MOI of 600 and fixed with 4% formalin 24 hours post-infection. Cells were incubated with a 1:50 dilution of anti-mouse C3 (MP Biomedicals, Solon, Ohio) followed by a 1:400 dilution of CY3-conjugated donkey anti-goat (Jackson ImmunoResearch Laboratories; West Grove, Pa.). Cells were imaged using an Olympus IX51 with appropriate filters, a Retiga 2000R FAST camera and QCapture Pro 5.0 (QImaging, British; Columbia, Canada) software.

Example 2

Subretinal Administration of Adenovirus

Examples involving animals were conducted in accordance with the Statement for the Use of Animals in Ophthalmic and Vision Research, set out by the Association for Research in Vision and Ophthalmology. C57B16/J mice were purchased from Jackson Laboratories and maintained in 12-hour dark light cycles in accordance with federal, state, and local regulations. Mouse subjects were anesthetized by intraperitoneal injection of 0.1 ml/10 g of ketamine (10 mg/ml)/xylazine (1 mg/ml), followed by application of one drop of proparacaine hydrochloride (0.5%) to each eye. Virus particles ($2 \times 10^9$) were injected into the sub-retinal space of 6-8 week old C57B16/J male mice using a trans-scleral/trans-choroidal approach. Both eyes were injected with the same virus in each subject (See also Cashman et al. 2002 Mol Ther 6: 813-823). A volumne of virus (1 µl) was administered using a 33G needle and a 5 µl glass syringe (Hamilton Inc.; Reno, Nev.).

Example 3

Scotopic Electroretinography

Subjects were kept for overnight dark-adaptation, were anesthetized, and then one drop of 1% tropicamide (Akorn, Inc) was applied to each eye to dilate the pupil. Body temperature of the mouse was maintained using an animal temperature controller (ATC 1000; World Precision Instruments; Sarasota, Fla.). Electroretinograms (ERGs) were recorded at two different light intensities (−10 and 0 dB) using LKC UTAS Visual Diagnostic Test System with Big Shot LED Ganzfeld using contact lens electrodes (LKC). Ten flashes were recorded and averaged for each light intensity.

Example 4

Tissue Harvest, Processing and Staining

Eyes of the subjects were fixed overnight in 4% paraformaldehyde, and were dehydrated in 15-30% sucrose in 0.1M phosphate buffer. The cornea, lens and iris were removed and the eyecups were embedded in Tissue-Tek compound (Adwin Scientific Industrial; Schaumburg, Ill.). Sections (14 µM) were excised using a cryostat (Microm 550). GSL I: Sections were incubated at 37° C. for ten minutes with 500 µg/ml BSA in PBS followed by 100 µg/ml FITC-conjugated *Griffonia simplicifolia* Lectin I (isolectin B4; Vector Labs, Burlingame, Calif.) in PBS for 1 hour at 37° C. Eyecups with retinas removed prior to fixation were stained as for sections, and blocking was performed for 30 minutes with 2.5 mg/ml BSA in PBS. Four relaxing cuts were administered prior to mounting on slides. Sections adjacent to those with representative GSL I stain for each of AdcmvC3 and AdcmvGFP-injected were stained for the following: DAPI: Sections were pretreated with phosphate buffered saline and 0.05% Triton (PBST) for 15 minutes, followed by 1 µg/ml DAPI in PBS for 5 minutes at room temperature (RT). Rhodopsin: After blocking with 6% normal donkey serum (Jackson ImmunoResearch; West Grove, Pa.) in 0.25% PBST for one hour at RT, sections were incubated for 2.5 hours with a 1:250 dilution of mouse monoclonal 1D4 in blocking buffer at RT, followed by a 1.5 hour incubation at RT with a 1:400 dilution of CY3-conjugated goat anti-mouse (Jackson ImmunoResearch). GFAP: Staining was performed as for rhodopsin with a 1:500 dilution of rabbit polyclonal antibody anti-GFAP (Novus Biologicals Inc., Littleton, Colo.) followed by a 1:500 dilution of CY3 goat anti-rabbit (Jackson ImmunoResearch), both in 6% normal goat serum. MAC: After blocking with 6% normal goat serum in 0.3% PBST for 30 minutes at RT, sections were stained for 2.5 hours at RT with a 1:200 dilution of rabbit anti-mouse C9 antibody in PBST, followed by 1:400 dilution of CY3-conjugated goat anti-rabbit (Jackson ImmunoResearch) at RT for 1 hour. In Examples herein, specificity of antibodies was determined using a control antibody of the same isotype. Sections and flatmounted eyecups were imaged using an Olympus IX51 with appropriate filters, a Retiga 2000R FAST camera and QCapture Pro 5.0 (QImaging Inc.; British Columbia, Canada) software.

Example 5

Retinal Detachment

To produce prolonged retinal detachment without adenovirus, six to eight week old C57B16/J mice were injected with 1 µl of 0.25% sodium hyaluronate (Fisher et al. 2005 Prog Retin Eye Res 24: 395-431). The eyes were harvested nine days following the injection and fixed with 4% paraformaldehyde. Cryosections were stained with FITC-GSL I. Retinal detachment was calculated for AdcmvC3-injected and AdcmvGFP-injected eyes by counting the number of sections with retinal detachment and multiplying by the thickness of each section (14 µM). Data were analyzed using an unpaired students t test.

Example 6

Fluorescein Angiography

Murine subjects were anesthetized and a drop of 1% tropicamide was applied to each eye. A volume (200 µl) of 2.5% sodium fluorescein (Akorn) in 1× PBS was injected intraperitoneally. Eyes were coated with 2% methylcellulose and a commercially available coverslip (Corning, No. 1; Corning Inc., Corning, N.Y.) was used to image retinal vessels using a Nikon C-PS160 dissecting microscope and appropriate filters. Eyes were monitored for three to ten minutes and images and then injected with sodium fluorescein. Images were captured five minutes following the fluorescein injection using an Olympus DP20 camera.

Example 7

Quantitative RT-PCR

Eyes were harvested and cornea, lens, iris and optic nerve removed. The remaining tissue was placed in RNA Stat-60 (Tel-Test, Inc) and homogenized using a VWR AHS200. Total RNA was purified as per manufacturer's instructions and treated for DNA contamination using a Turbo DNA-free kit (Applied Biosystems. Total RNA was assayed for C3, VEGF, and β-actin using iScript one-step RT-PCR kit (Bio-Rad Inc., Hercules, Calif.) and the Applied Biosystems assays (Mouse C3: Mm00437858_m1; Mouse VEGF: Mm00437304_m1; Mouse β-actin: part #4352663) on a Bio-Rad iQ5 Multicolor Real-Time PCR Detection System and analyzed using iQ5 Optical System software.

Example 8

Statistical Analysis

Statistical analyses were performed using Prism 5 (GraphPad Software Inc., La Jolla, Calif.). In Examples comparing three conditions, data were analyzed using a one-way ANOVA with a post-Newman-Keuls multiple comparison test for significance. Data using other conditions were analyzed using an unpaired students t-test. For qRT-PCR, a t-test was performed to determine significance in which data from uninjected subjects were assigned the hypothetical value of 1.0 and significance of the fold-difference of C3 and GFP was measured relative to this value.

Example 9

C3 Expression In vitro

C3 is a secreted protein, produced as a single polypeptide precursor, pro-C3, with a predicted molecular weight of 170 kDa. Pro-C3 is cleaved intracellularly to form C3 and consists of an α chain (107 kDa) and β chain (62 kDa) connected by disulfide bonds (Bednarczyk et al. 1988 Scand J Immunol 27: 83-95; and Van den Berg et al. 1989 J Immunol Methods 122: 73-78). Expression of C3 from AdcmvC3 was determined by immunostaining contacted human embryonic retinoblasts (HERs, FIG. 1 panel A left graph). C3 staining in the AdcmvC3-contacted cells was observed to be primarily cytoplasmic. The distribution of GFP in the control AdcmvGFP-contacted cells was diffuse and the GFP was visualized throughout the nucleus and cytoplasm.

Figure 1B:
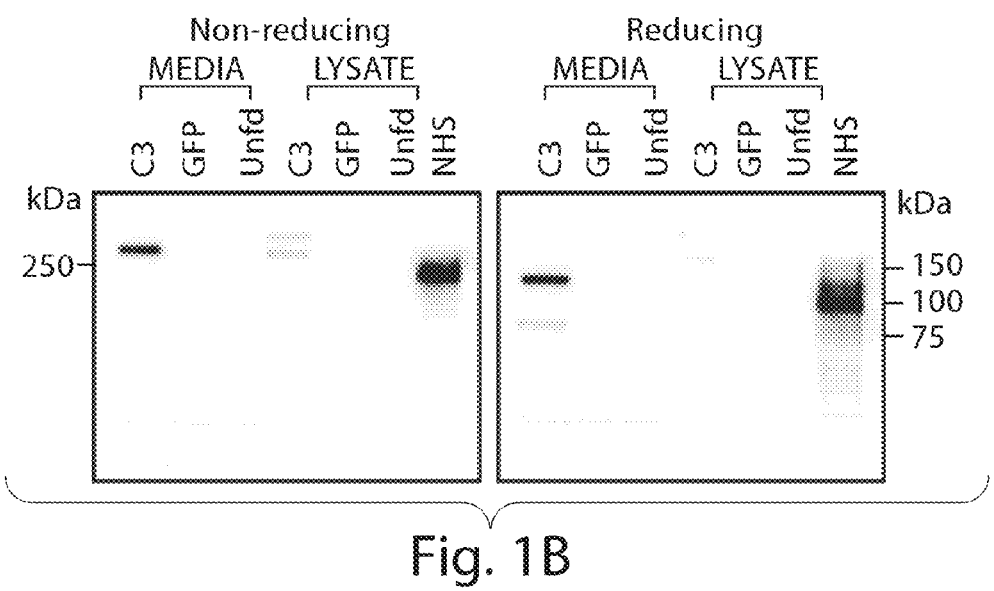

To determine the correct size and processing of C3, western blot analysis was performed for both lysates and media of HER cells contacted with AdcmvC3 using non-reducing (FIG. 1 panel B left) and reducing conditions (FIG. 1 panel B right). Under non-reducing conditions two bands were observed in the lysates of AdcmvC3-contacted cells. The approximate molecular weight of these bands corresponded to C3 and pro-C3. The processed C3 molecular weight band (at about 170 kDa) was the sole band that was observed in the media. Using reducing conditions, the two bands observed in the media were identified as the C3 α chain and β chain. Lysates were observed to have a faint higher molecular weight band consistent with non-reduced C3.

Example 10

Increased Permeability of Blood Vessels in the Presence of High Levels of C3

A key feature of a large proportion of AMD eyes is the spontaneous growth of new and leaky choroidal and retinal blood vessels (Yannuzzi et al. 2001 Retina 21: 416-434). Fluorescein angiography was performed on subjects injected with adenoviruses expressing either C3 or GFP into the subretinal space, at eight days and 14 days following injection.

Figure 2:
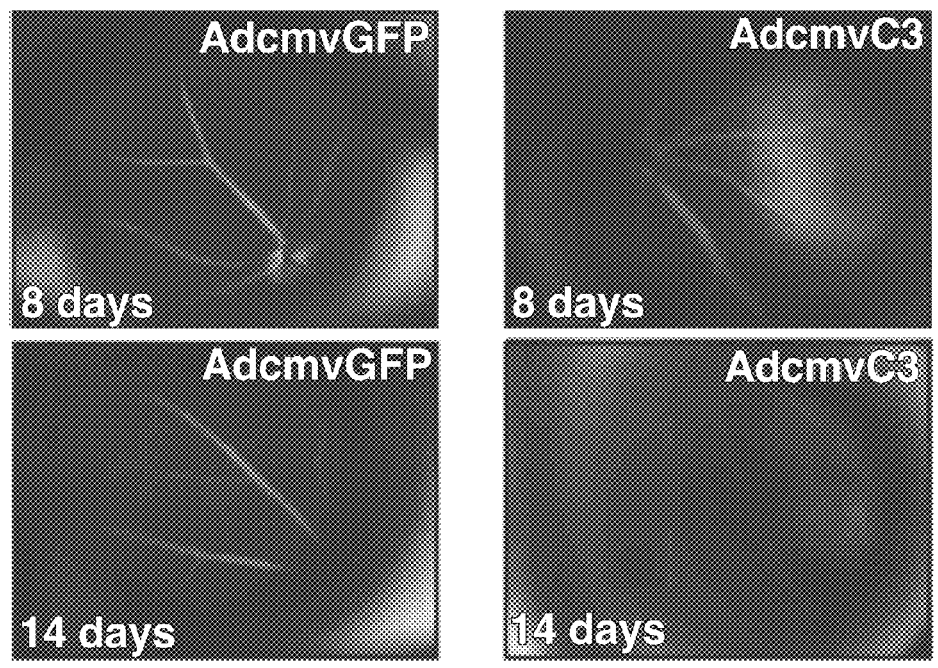
FIG. 2 is set of photomicrographs of murine subjects subretinally injected with recombinant adenovirus AdcmvC3 (right photmicrographs) or AdcmvGFP (left photomicrographs), and analyzed by fluorescein angiography eight days (top row) or 14 days (bottom row) following injection. Eight days post-injection discrete regions of leakage were observed in 25% of eyes injected with AdcmvC3, and 14 days post-injection rapid leakage of fluorescein was observed in 100% of AdcmvC3-injected eyes. No fluorescein angiography leakage was observed in the subjects injected AdcmvGFP either eight days or 14 days following injection. (eight days) n=8 for AdcmvC3, AdcmvGFP; (14 days) n=5 for AdcmvC3, n=4 for AdcmvGFP.

None of the eight AdcmvGFP-injected eyes (GFP-injected) tested showed evidence of leakiness eight days following injection. In contrast 25% (two out of eight) of AdcmvC3-injected (C3-injected) eyes showed fluorescein leakage (FIG. 2) eight days following injection. Fourteen days after injection, rapid diffusion of fluorescein into the vitreous was observed in all five (100%) of the C3-injected eyes tested (FIG. 2). The smaller retinal vessels were no longer visible in the C3-injected eyes. None of the four GFP-injected eyes analyzed 14 days following adenovirus injection showed any fluorescein leakage.

Thus, contacting eyes with AdcmvC3 resulted in increased fluorescein leakage and increased neovascularization was observed in ocular blood vessels of the subjects compared to GFP injected subjects.

Example 11

C3 Over-expression Results in Extensive Proliferation of Endothelial Cells

Neovascularization is typically preceded by proliferation and migration of vascular endothelial cells (Ucuzian et al.

Figure 3A:
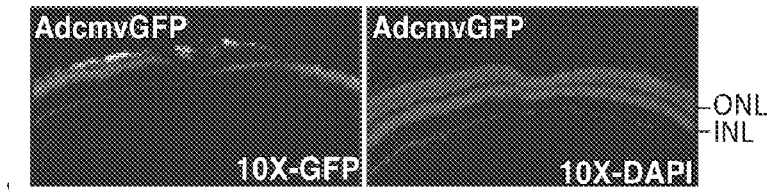
FIG. 3 panels A-C are a set of photomicrographs of murine eyes injected with either AdcmvC3 or AdcmvGFP and then stained with FITC-conjugated *Griffonia simplicifolia* lectin-I (GSL) I isolectin B4, a lectin specific for endothelial cells, or 4'-6-Diamidino-2-phenylindole (DAPI). Eyes were visualized also using GFP fluorescence. ONL/INL, outer/inner nuclear layer; GSL I, *Griffonia simplicifolia* Lectin. n=6 for AdcmvGFP and AdcmvC3.
Figure 3B:
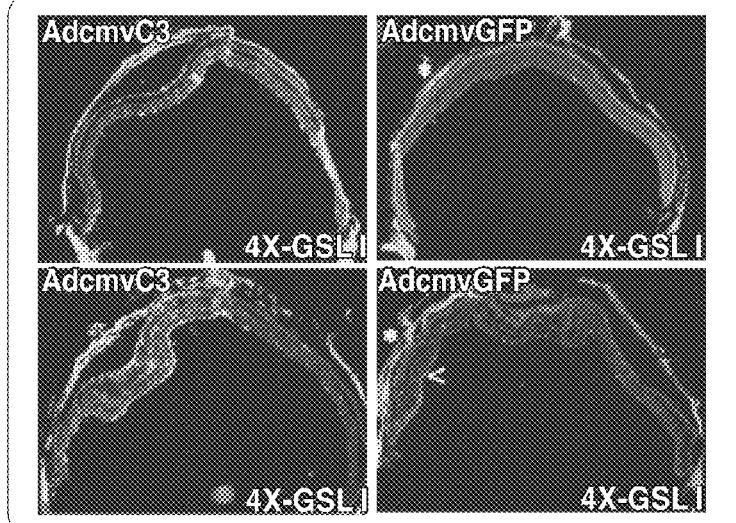
Figure 3C:
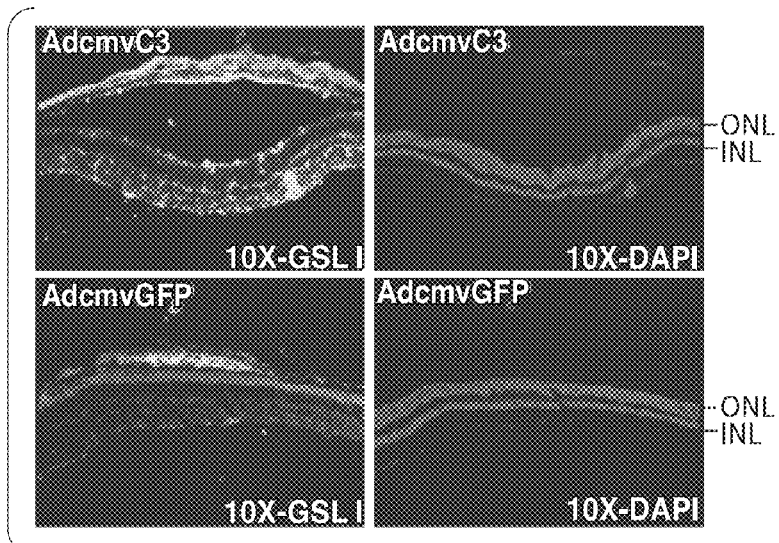

2010 J Burn Care Res 31: 158-175). To determine the occurrence and location of endothelial cell proliferation, C3 adenovirus-injected or control GFP adenovirus-injected eyes were harvested nine days following injection. Cryosections were then stained using the FITC conjugated endothelial cell marker GSL I, isolectin B4. Prior to GSL I staining, cryosections of GFP adenovirus-injected eyes were analyzed for GFP expression (FIG. 3 panel A).

It was observed that the extent of GFP expression varied between injections, and expression was observed only in the RPE cell layer. After staining with GSL I, C3 adenovirus-injected eyes exhibited extensive staining throughout the retina relative to GFP-injected (FIG. 3 panel B). Increased GSL I staining was observed in the region of injection in the choroid of GFP-injected eyes compared to uninjected control eyes. Increased GSL I staining was observed also in the retina in the region of injection in approximately 50% of GFP adenovirus-injected eyes compared to uninjected controls. The observed GSL I staining for was much less intense for GFP adenovirus injected eyes than for eyes injected with C3 adenovirus vector, and staining was limited to the inner retina. Eyes injected with C3 adenovirus vector were observed at a higher magnification to have GSL I-positive cells at the RPE/retinal interface and in each layer of the retina (FIG. 3 panel C). The increased GSL I staining in the GFP adenovirus-injected eyes was restricted mostly to the choroid with some increased staining in the retina, unlike the ubiquitous staining that was observed for the C3 adenovirus-injected eyes (FIG. 3 panel C).

Figure 4A:
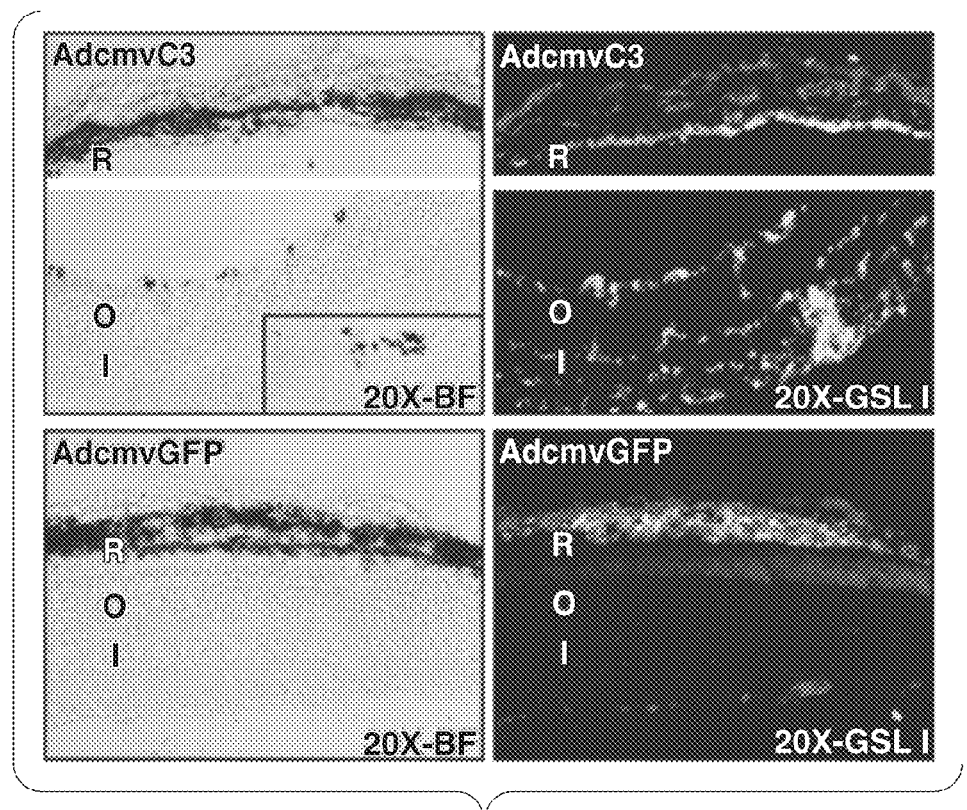
FIG. 4 panels A-B are a set of photographs showing increased disruption of murine RPE and choroid in AdcmvC3-contacted eyes compared to AdcmvGFP-contacted eyes. Bright field illuminated eyes are shown in the left column and eyes stained with FITC-GSL I stain are shown in the right column. BF, bright-field; GSL I, *Griffonia simplicifolia* lectin I; R, RPE; 0, outer nuclear layer; I, inner nuclear layer; C, choroid. n=6 for AdcmvGFP and AdemvC3.
Figure 4B:
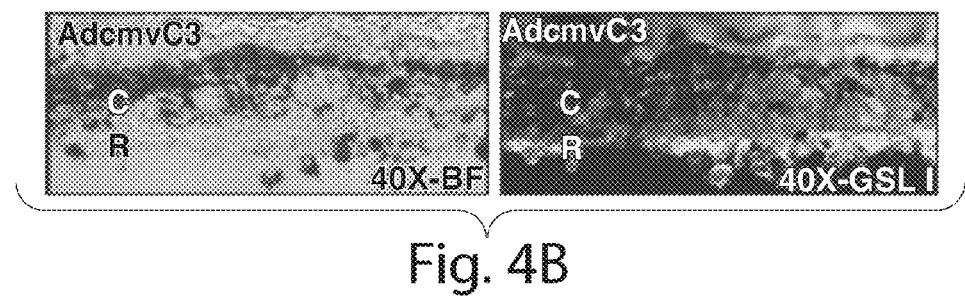
Figure 5A:
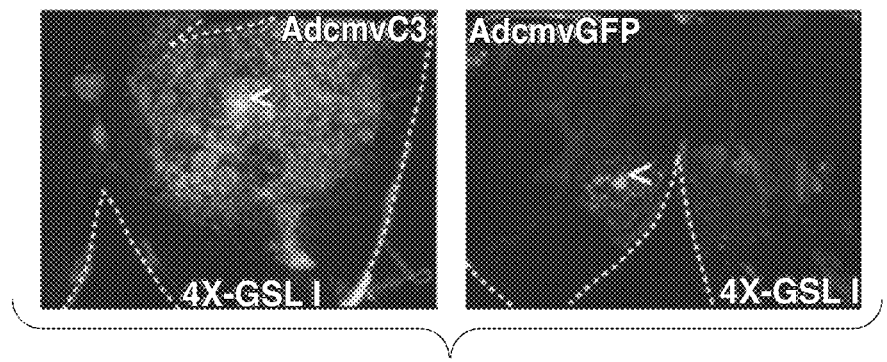
FIG. 5 panels A-E are a set of photomicrographs and bar graphs that show increased retinal detachment in AdcmvC3-contacted murine eyecups.
Figure 5B:
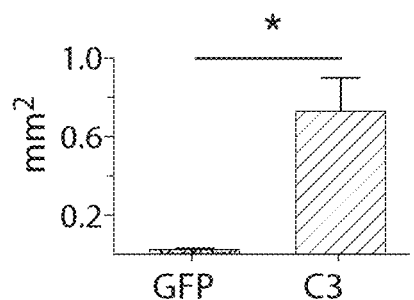
Figure 5C:
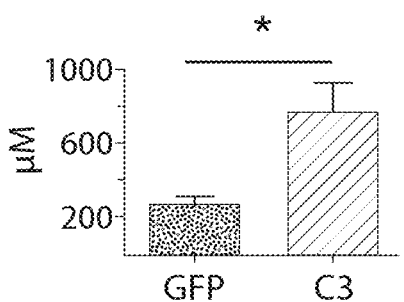
Figure 5D:
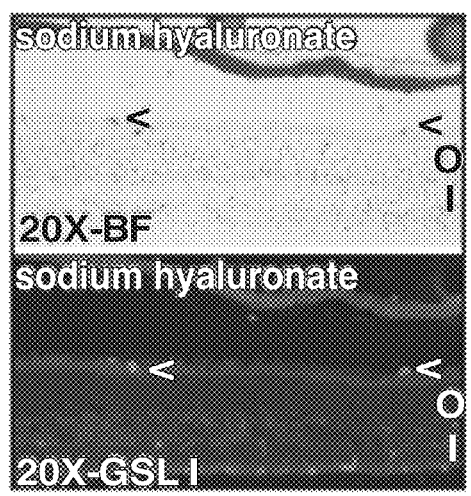
Figure 5E:
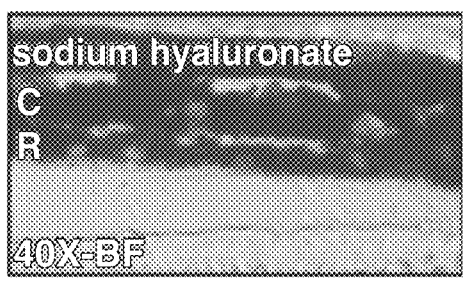

Comparison of brightfield (BF) images with those of FITC-GSL I showed a disruption of the RPE/Choroid within the region of GSL I staining in C3 adenovirus injected eyes (FIG. 4 panel A). Migration of pigmented cells into the retina was observed in a number of eyes (2/6). See FIG. 4 panel inset. The integrity of the RPE cells was maintained in GFP adenovirus injected eyes, and the GSL I-positive endothelial cells did not breach the RPE (FIG. 4 panel A). Closer examination of the RPE/choroid of C3-injected retinas indicated a loss of RPE cells and a loss of pigment, and it was observed that cells in the RPE/choroid region stained positive for GSL I (FIG. 4 panel B).

Example 12

AdcmvC3-injected Eyes Had Increased Retinal Detachment

To quantitate the extent of endothelial cell proliferation in C3-injected subjects compared to GFP-injected subjects, eyecups with retina removed were stained with FITC-GSL I (FIG. 5 panel A). Eyecups injected with C3 adenovirus vector were observed to have a significantly greater area of GSL I staining ($0.73 \pm 0.17$ mm$^2$; $p<0.05$) than control GFP-injected eyecups ($0.03 \pm 0.02$ mm$^2$; FIG. 5 panel B).

Retinal detachment was observed within the region of most intense GSL I staining in each of the C3-injected eyes (FIG. 5 panels A-C). Quantitation of the extent of retinal detachment observed in both GFP-injected and C3-injected mice showed that retinal detachment in C3-injected retinas was significantly greater (2.6-fold, $p<0.05$) than the retinal detachment observed in GFP-injected retinas (FIG. 5 panel C).

To determine whether increased endothelial cell staining and disruption of the RPE/choroid observed in C3-injected mice was caused by a greater amount of retinal detachment, 0.25% sodium hyaluronate was injected into the subretinal space of mice to induce a prolonged retinal detachment (Fisher et al. 2005 Prog Retin Eye Res 24: 395-431). Eyes were harvested, fixed, and cryosections stained with GSL I nine days after injection. GSL I staining was observed almost exclusively in the inner nuclear layer (INL; FIG. 5 panel D), with a small number of pigmented cells at the RPE/retinal interface staining positive for GSL I. Observation of the RPE/choroid at increased magnification in one of the sodium hyaluronate-treated eyes showed an intact RPE layer (FIG. 5 panel E). No GSL I staining was observed in this region of the eye of each of the subjects. These data show that increased endothelial cell staining and disruption of the RPE/choroid observed in C3-injected mice was due to the expression of C3 and not to greater retinal detachment.

Example 13

Photoreceptor Degeneration and Muller Cell Re-activity in C3 Injected Retinas

Figure 6A:
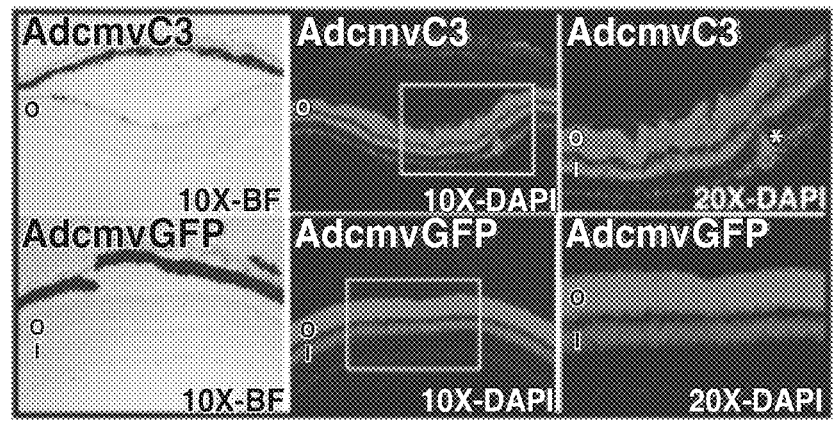
FIG. 6 panels A-C are a set of photomicrographs taken nine days after injection with AdcmvC3, showing disturbance of the outer nuclear layer of murine retinas, outer segment loss, and Muller cell activation. BF, bright-field; O, outer nuclear layer; I, inner nuclear layer; Unjd, uninjected. n=4 for AdcmvGFP and AdcmvC3.
Figure 6B:
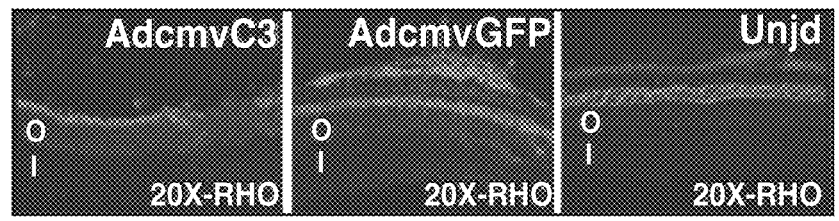
Figure 6C:
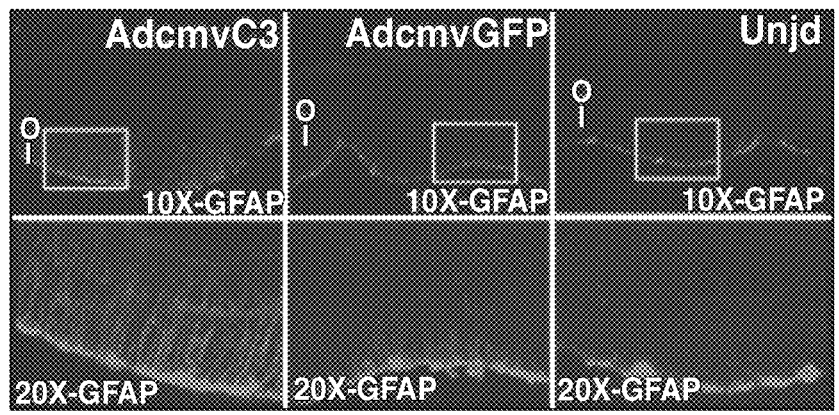

The amount of photoreceptor degeneration resulting from contacting ocular tissues with AdcmvC3 was analyed. Staining of C3-injected retinas with the nuclear stain DAPI indicated a perturbation of the outer nuclear layer (ONL), while the inner nuclear layer (INL) remained relatively undisturbed (FIG. 6 panel A). TUNEL staining of C3-injected retinas was negative, indicating little or no apoptosis in the ONL. To further investigate the effect AdcmvC3 on integrity of photoreceptors, retinal sections were stained for rhodopsin. It was observed that eyes contacted with AdcmvC3 showed substantial loss of outer segments of the retina compared to eyes contacted with AdcmvGFP and control eyes that were not injected (FIG. 6 panel B). The majority of rhodopsin staining in GFP-injected retinas and uninjected retinas was localized in the outer retina segments, with very little staining in the ONL.

Retinal diseases are known to activate certain cells in the eye, specifically Muller cells are known to become activated (Bringmann et al. 2006 Prog Retin Eye Res 25: 397-424). Mulller cell activation in uninjected ocular tissues or ocular tissues injected with AdcmvC3 and AdcmvGFP was determined by analyzing expression of glial fibrillary acidic protein (GFAP). Data show detectable activation of Muller cells in C3-injected eyes. Activation of Muller glia was specifically determined because GFAP was detected throughout the Muller cell, extending from the inner to outer limiting membrane (FIG. 6 panel C). Surprisingly, pockets of little or no staining were also observed within this region of eyes injected with AdcmvC3. The distinctive staining pattern for C3 injected eyes was observed only in the area of retinal detachment. GFAP staining was observed extending into the inner plexiform and nuclear layers of the GFP-injected eyes, indicating some reactivity in these retinas. The uninjected retinas resulted in GFAP staining in astrocytes and muller cell endfeet at the inner limiting membrane. Thus data show that eyes injected with AdcmvC3 showed decreased expression of rhodopsin indicating photoreceptor degeneration compared to eyes injected with AdcmvGFP and control eyes. It was observed also that AdcmvC3 injected into eyes resulted in increased Muller cell activation which indicated the presence or risk of a retinal disease.

Example 14

Increased C3 Expression Resulted in Reduced Retinal Function

ERGs are non-invasive and are used to evaluate function of specific layers or neurons of the eye including the photoreceptors (rods and cones), retina including inner retinal cells such as bipolar and amacrine cells, and the ganglion cells. Abnormal ERGs indicate loss of ocular tissue function and the presence of a disease or negative condition.

Figure 7:
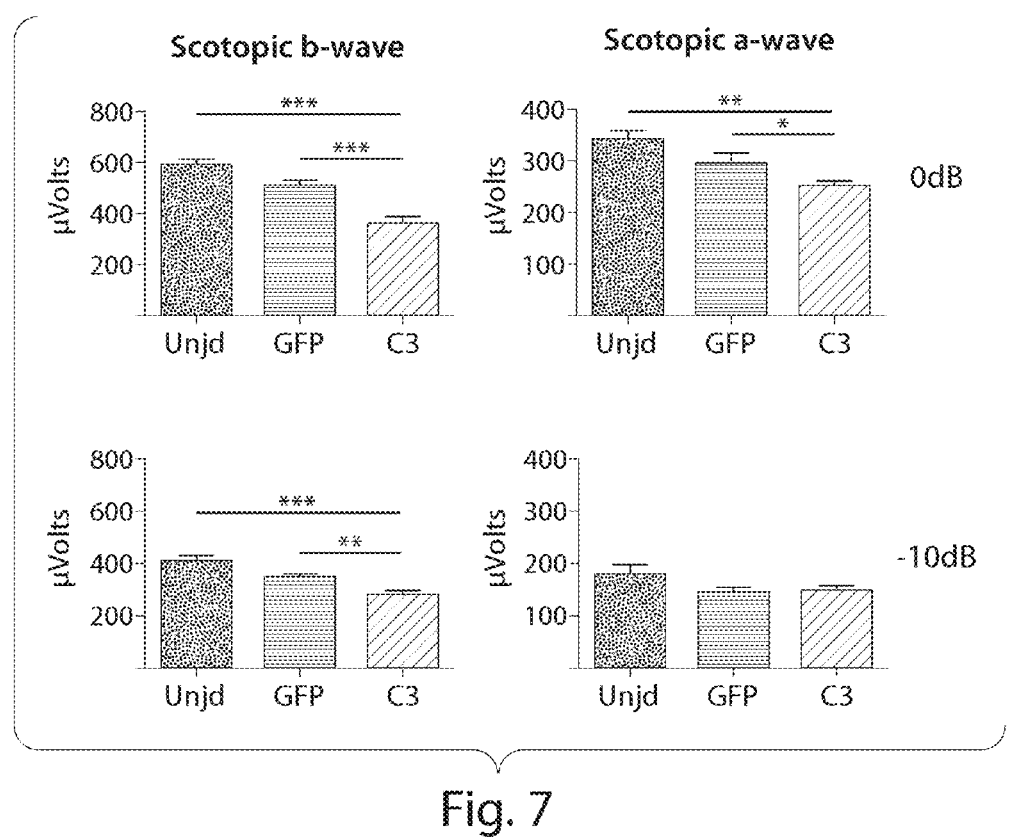
FIG. 7 is a set of bar graphs showing that electroretinogram amplitude values (microvolts, $\mu M$) of murine eyes on the ordinate as a function of the adenovirus vector that was injected in the subretinal space (abscissa). Eyes were injected with either AdcmvC3 (C3) or AdcmvGFP (GFP). Control subjects were not injected (Unjd). After dilating the pupils, electroretinograms (ERGs) for each eye were recorded at two different light intensities, zero decibel units (top row) and minus ten decibel units (dB; bottom row). Data were analyzed using a-wave (a; right column) and b-wave (b; left column) analyses. Data are presented as the mean±standard error. Beta wave amplitudes of AdcmvC3-contacted retinas were observed to be significantly reduced at both higher and lower light intensities compared to both AdcmvGFP-contacted eyes and uninjected control eyes. In contrast, a wave amplitudes for AdemvC3-contacted retinas were observed to be significantly impaired only at the higher light intensity of zero dB compared to both AdcmvGFP-contacted eyes and uninjected control eyes. No significant reduction was observed in retinal function for AdcmvGFP-contacted eyes relative to uninjected eyes. Thus, data showed significantly reduced ocular functionality in AdcmvC3 injected retinas. n=24 for each of AdcmvGFP— and AdcmvC3-injected eyes, n=8 for uninjected.

Eight days following injection with AdcmvC3 or AdcmvGFP, scotopic electroretinograms (ERGs) were recorded at two different light intensities, −10 dB and 0 dB. At both intensities, b-wave amplitudes were observed to be significantly reduced in C3-injected eyes relative to GFP-injected or uninjected eyes, $p<0.05$ (FIG. 7 left graphs). B-wave amplitudes of C3-injected mice were reduced by 29.8±7.4% (0 dB) and 21.5±7.1% (−10 dB) compared to GFP-injected mice. A-wave amplitudes also were observed to be significantly reduced in C3-injected eyes at the higher light intensity (0 dB) compared to both uninjected eyes or GFP-injected eyes, $p<0.05$ (FIG. 7 top row right graph). However, the a-wave amplitudes for the C3-injected eyes were not reduced at the lower light intensity (−10 dB) compared to control and GFP injected eyes (FIG. 7 bottom row right graph). A-waves amplitudes observed in C3-injected mice at 0 dB were observed to be reduced by 18.4±7.3% compared to GFP-injected eyes. The ratio of b-wave amplitudes to a-wave amplitudes was also reduced (15.5±3.9%) significantly in C3-injected mice compared with GFP-injected eyes at the higher light intensity (0 dB, $p<0.05$). However the ratio was comparable to that observed at the lower light intensity (−10 dB). No significant reduction was observed in retinal function for GFP-injected eyes relative to control uninjected eyes.

Example 15

C3-injected and GFP-injected Retinas Differ in Expression of C3 and VEGF

Vascular endothelial growh factor (VEGF) is a signal protein produced by cells and that stimulates vasculogenesis and angiogenesis. Overexpression of VEGF has been associated with vascular disease in the retina of the eye and other parts of the body (Cashman et al. 2006 Invest Ophthalmol Vis Sci 47: 3496-3504). The effect of administering AdcmvC3 to ocular tissues on increase in expression of VEGF was analyzed as follows.

Figure 8A:
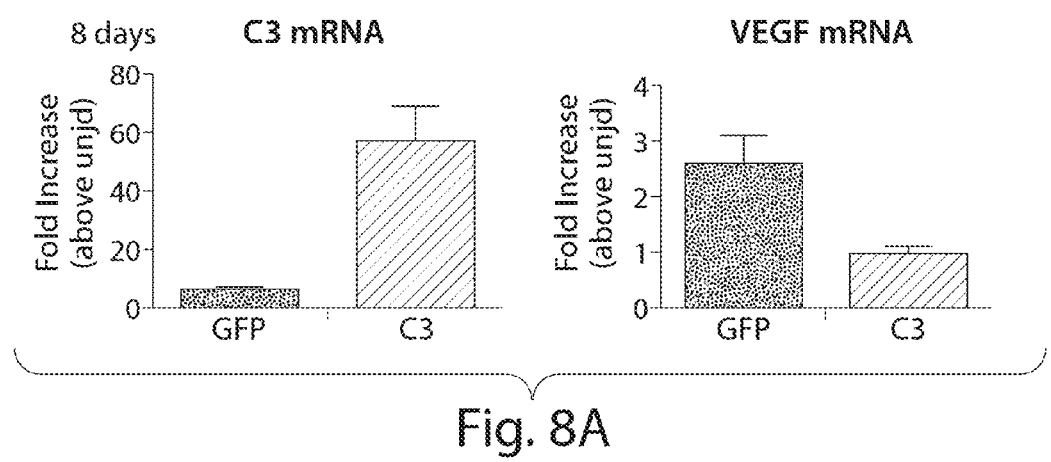
FIG. 8 panels A-B are a set of bar graphs showing that expression of C3 mRNA was increased in AdcmvC3-injected retinas compared to uninjected retinas. The bar graphs show fold increase of mRNA above uninjected subjects on the ordinate as a function of the adenovirus vector injected into the eyes of the mice, AdcmvC3 (C3) or AdcmvGFP (GFP). Three days (FIG. 8 panel B) or eight days (FIG. 8 panel A) after injection, mRNA quantitation was performed to determine amount of C3 (left column) or vascular endothelial growth factor (VEGF). Expression of C3 mRNA was observed to be significantly increased in AdcmvC3-contacted retinas at both three days and eight days following injection compared to AdcmvGFP-contacted retinas. A significant fold-increase in VEGF mRNA in AdcmvC3-injected subjects was observed three days following injection, and no change in VEGF mRNA was observed at eight days following injection. A significant fold-increase in VEGF mRNA was also observed in AdcmvGFP-contacted retinas compared to uninjected retinas. Thus expression of VEGF mRNA increased in both AdcmvGFP-contacted eyes and AdcmvC3-contacted eyes. Data were presented as the mean±standard error. Unjd, uninjected. n=6 for AdcmvGFP and AdcmvC3, and n=12 for uninjected.
Figure 8B:
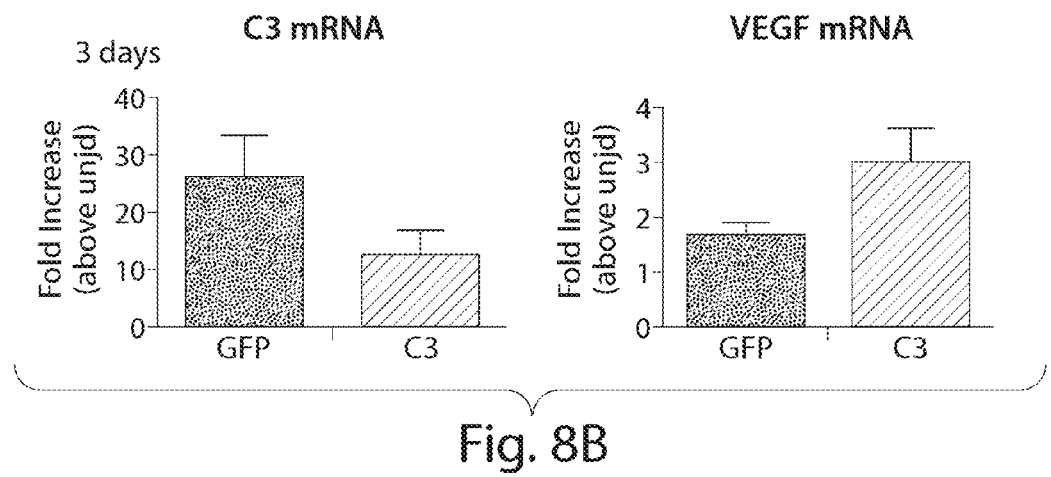

C3-contacted eyes and GFP-contacted eyes were examined for levels of C3 expression and VEGF expression eight days following injection of each adenovirus vector. It was observed that expression of C3 mRNA was significantly increased in both C3-contacted eyes (57.0±11.8-fold, $p<0.01$) and GFP-contacted eyes (6.2±1.2-fold, $p<0.01$) compared to control uninjected eyes (FIG. 8 panel A left graph). Surprisingly, it was observed that C3-contacted eyes showed little or no change in VEGF expression (0.97±0.14-fold above uninjected eyes), and that GFP-contacted eyes had a significant increase in VEGF expression, 2.6±0.5-fold above uninjected eyes, $p<0.05$ (FIG. 8 panel A right graph).

The possibility that VEGF mRNA levels increased in C3-contacted eyes at time prior to eight days following injection, which is shown in FIG. 8 panel A, was explored. Expression of both C3 and VEGF mRNAs in whole eyecups three days following injection was analyzed.

Data showed a significant increase in VEGF mRNA levels in C3-contacted eyes (2.98±0.62-fold above uninjected; FIG. 8 panel B bottom row right graph). Expression of VEGF was significantly greater in C3-contacted eyes than in GFP-contacted eyes, an increase of 1.67±0.21-fold $p<0.05$ (FIG. 8 bottom row right graph). Data show that both GFP— and C3-contacted eyes had significantly increased ($p<0.05$) C3 mRNA expression relative to uninjected at three days after injection (FIG. 8 bottom row left graph). Levels of C3 mRNA (above uninjected eyes) in GFP-contacted eyes were 25.9±7.1-fold higher and in C3-contacted eyes were 12.65±4.02-fold higher respectively (not significant).

Example 16

Deposition of Membrane Attack Complex (MAC) in AdcmvC3-injected Retinas

To determine whether complement was activated in C3-injected eyes, retinas injected with either AdCADC3 or AdCADGGFP were analyzed for MAC staining. Eyecups were harvested nine days following injection and were stained for MAC using a polyclonal antibody to mouse C9 (FIG. 9 panels A-C).

Figure 9A:
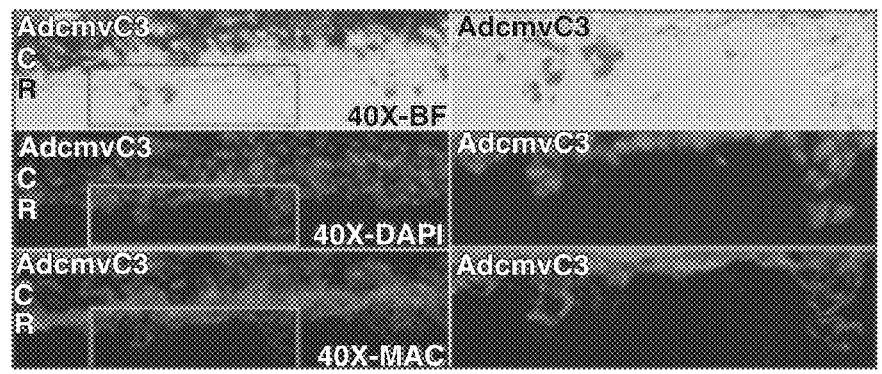
FIG. 9 panels A-C are a set of photomicrographs showing that AdcmvC3-injected retinas exhibited MAC deposition on endothelial cells and outer segments. Murine retinas were subretinally injected with either AdcmvC3 or AdcmvGFP and were visualized by bright field, and stained for DAPI, or for MAC using anti-human C5b-9 antibody. BF, bright-field; C, choroid; R, RPE, O, outer nuclear layer, GSL I, *Griffonia simplificolia* Lectin I; MAC, membrane attack complex.
Figure 9B:
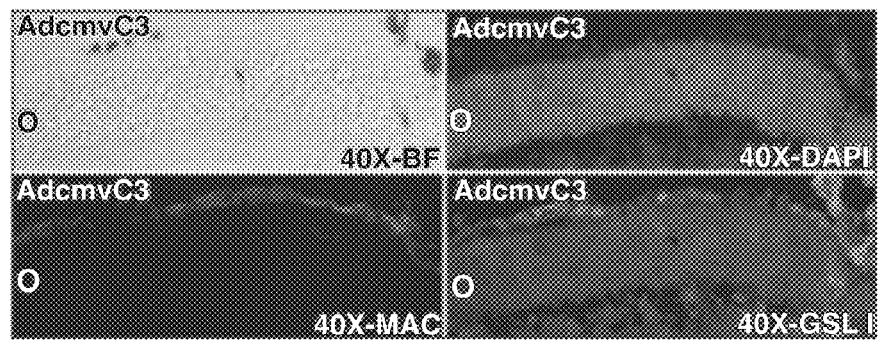
Figure 9C:
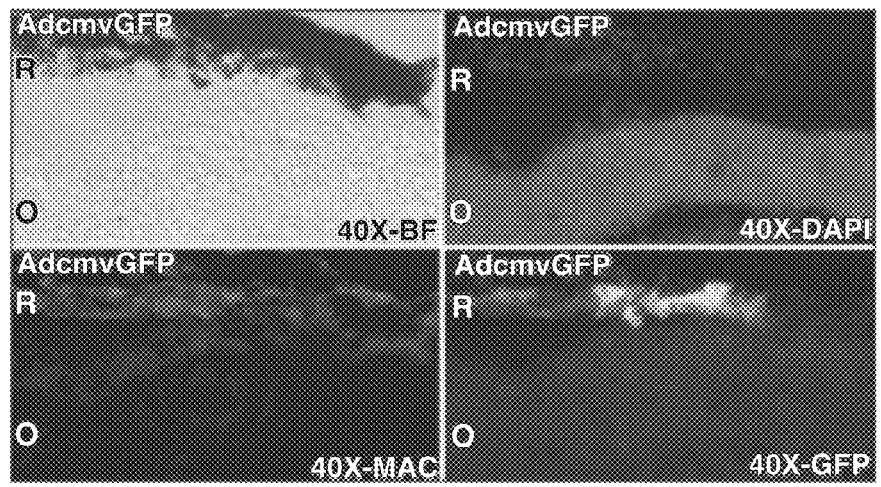

Data show that for eyes contacted with AdcmvC3 MAC deposition was observed on cells at the RPE/retinal interface (FIG. 9 panel A). AdcmvC3-contacted cells stained positive also for FITC-GSL I and a higher magnification image of GSL I-positive endothelial cells showed punctate membrane staining characteristic of MAC deposition at the RPE/retinal interface. Strong MAC staining was observed on the remaining outer segments of the photoreceptors of the eyes contacted with AdcmvC3 (FIG. 9 panel B).

Contacting retinas with GFP-adenovirus vector resulted in MAC staining in the choroid (FIG. 9 panel C), an area of the eye that also stained strongly for GSL I. MAC staining was also observed on some of the AdcmvGFP-transduced RPE cells (FIG. 9 panel C) at the site of injection, but was not observed on adjacent RPE cells and the retina.

An adenovirus vector was constructed carrying a gene that encoded C3 (AdcmvC3) and analysis of cells showed that the adenovirus had mediated delivery of C3 to murine ocular tissues including RPE. AdcmvC3 induced significant negative functional and anatomical changes associated with ocular and retinal diseases such as AMD. These data show that an animal model provided herein is useful in assessing the role of complement in ocular or retinal pathology, and in developing anti-complement therapies for retinal diseases associated with complement activation. Using this and other models for AMD, CD46, CD55 and STAC proteins are shown to be effective therapeutic agents for treating subjects having a complement disorder such as AMD.

Example 17

Cell Lines and Primary RPE Cell Culture

HEPA 1c1c7 and 293 cell lines were obtained from American Type Culture Collection (Manassas, Va.), and used to determine the effectiveness of the therapeutic agents. Cell culture reagents were purchased from Invitrogen Life Technologies. Hepa1c1c7 cells were maintained in αMEM/10% FBS. The 293 cells and human embryonic retinoblast cell line 911 (911) cells were maintained in DMEM/10% FBS (Fallaux et al. 1996 Hum Gene Ther7(2): 215-22).

Primary mouse RPE cells were obtained from six week old to ten week old C57B1/6 mice. Eyes were enucleated, and the lens, cornea, and retina were removed to reveal the RPE cell layer. Eye-cups were incubated for 1 hour at 37° C. in 200 μl of 0.25% trypsin/EDTA. RPE cells were pulled off in sheets and homogenized in 20 μ αMEM/10% FBS. The suspension was placed in the center of an eight well poly-D-lysine coated chamber slide (Becton Dickenson, Franklin Lakes, N.J.) for ten minutes for cells to adhere to the plate, and an additional 130 µl αMEM/10% FBS was added to each well. Cells were kept in a humidified incubator at 37° C. with 5% $CO_2$ for three days prior to use.

This and other models of AMD were used to determine whether CD46, CD55 and STAC proteins are effective therapeutic agents for complement-based conditions of the eye.

Example 18

CD46 Adenovirus Construction

E1/E3-deleted adenovirus serotype 5 was used to construct a vector to express human CD46 (hCD46), or as a control, to express no transgene. hCD46, ATCC (MGC-26544; GenBank ID: BC030594; SEQ ID NO: 3), was excised from pBluescriptR using EcoRI and SspI and inserted into pCAGEN using EcoRI and EcoRV between a CMV enhancer/chicken β-actin promoter (CAG) and a rabbit globin polyadenylation (pA) termination sequence. The sequence containing CAG, hCD46, and pA was excised from pCAGEN using SpeI and HindIII and inserted into pShuttle using XbaI and HindIII (He et al. 1998 Proc Natl Acad Sci 95(5): 2509-2514. The pShuttle was recombined with Adeasy-1 then was linearized and transfected into 293 cells and virus was produced (Cashman et al. 2004. 324(1): 129-39). Following initial transfection virus was amplified in 911 cells. Viral purification was performed using the adenopure purification kit (Puresyn Inc., Malvern, Pa.) and viral titer determined at OD260 using a spectrophotometer then plaque-purified (Kumar-Singh et al. 2000 Methods Enzymol 316: 724-743). The hCD46 or pA expressing viruses are identified herein as AdCAGCD46 and AdCAGpA, respectively (See also Ramo et al. 2008 Invest Ophthalmol Vis Sci 49(9): 4126-36, which is incorporated herein in its entirety).

Example 19

Immunoblotting and Western Blots

Infection/contact of 911 cells was performed with either AdCAGCD46 or AdCAGpA at a multiplicity of infection (MOI) of 1000. After 24 hours, cells were collected by trypsin treatment and centrifugation, and were lysed in lysis buffer (SDS/triton) containing protease inhibitors (leupeptin, aprotinin, PMSF). Lysates were analyzed by electrophoresis and were run in a 12.5% tris HCl pre-cast gel (Biorad Inc., Hercules, Calif.). Following transfer, the nylon membrane was probed with a mouse anti human CD46 antibody (MEM258, serotec) at a dilution of 1:1000, and was then blocked to prevent non-specific binding. The membrane was then contacted with a HRP conjugated secondary antibody which was detection with luminol (PIERCE chemiluminescent subtrate kit).

Example 20

Complement Assay Using Hepa 1c1c7 Cells and ADCAGCD46

Hepa1c1c7 cells were contacted (MOI 1000) for three days with AdCAGCD46 or AdCAGpA in αMEM/2% FBS. For FACS analysis the cells were collected by trypsinization (0.25%/EDTA), were re-suspended in 1× PBS containing 0.5% FBS, centrifuged at 1200 RPM/4° C., and $5 \times 10^5$ cells re-suspended in 500 µl ice-cold Gelatin Veronal Buffer containing $Ca^2$ and $Mg^2$ ($GVB^{2+}$) (Complement Technology).

Complement was then activated on a suspension of $5 \times 10^5$ cells. Each cell was used for FACS analysis so that forward and side scatter was assessed for cell viability. To activate the complement pathways, 25 µg/ml rat anti-mouse emmprin (Serotec MCA2283) was added for 30 minutes at 4° C. followed by 10% Normal Human Serum (NHS) (Sigma), and the mixture was incubated at 37° C. for one hour with constant rotary motion. Other sets of control cells were treated at 56° C. for one hour with 10% Heat Inactivated NHS (HI-NHS). Cell lysis was determined by propidium iodide (PI) exclusion. PI was added to each sample (1 µl PI into 500 µl $GVB^{2+}$) and $2.5 \times 10^4$ cells were counted by FACS (FACS-Calibur) for PI uptake (CellQuest Pro software, Becton Dickinson).

To preferentially activate the alternative pathway, cells were collected as described and were re-suspended in $GVB^{2+}$. A sample containing $5 \times 10^5$ cells was then pre-incubated with 25 µg/ml rat anti-mouse emmprin antibody and incubated for 30 minutes at 4° C. Either 10% NHS or 10% HINHS containing 7 mM Mg/10 mM EGTA (MgEGTA) was added and the mixture was incubated at 37° C. for 1 hour.

For MAC staining of Hepa1c1c7, cells were plated into an eight-well chamber slide (Becton Dickinson) and transfected with either AdCAGCD46 or AdCAGpA for three days (MOI 1000). Each well was incubated with 25 µg/ml emmprin for 30 min. at 4° C. followed by either 10% NHS or 10% HINHS in $GVB^2$ at 37° C. for five minutes with MgEGTA to de-activate the classical pathway. Cells were washed twice with cold 1× PBS, fixed for 15 minutes in 10% neutral buffered formalin, and stored in 1× PBS. Cell lysis was determined using PI exclusion.

Example 21

CD46 Complement Assay on Primary Mouse RPE Cells

Cells were transfected with either AdCAGCD46 or AdCAGpA at an MOI of 1000 for three days in αMEM/10% FBS. The medium was removed and 50 µg/ml rat anti mouse emmprin added and cells were incubated at room temperature for one hour. Following the emmprin treatment, 50% NHS or 50% HINHS containing MgEGTA was added to the cells which were then incubated at 37° C. for one hour. Cells were washed three times in cold 1× PBS, fixed in 10% NBF for 15 minutes, and stored in 1× PBS at 4° C.

Example 22

CD46 Complement Assay Performed with Mouse Eye-cups

Murine subjects were injected subretinally with adenovirus vector, and were sacrificed eight days later using carbon dioxide and each of the lens, cornea, and retina were removed. Each eye-cup was incubated in $GVB^{2+}$ containing 140 µg/ml rat anti mouse emmprin for one hour at 4° C. Either 50% NHS or 50% HINHS was added directly to the $GVB^{2+}$/emmprin mixture and eyecups were incubated for four minutes at 37° C. MgEGTA was added to each eyecup sample which was then incubated at 37° C. for an additional 56 minutes. Samples were washed three times in cold 1× PBS and fixed overnight at 4° C. in 4% paraformaldehyde.

Example 23

Immunohistochemistry

To detect membrane expression of CD46 in hepa1c1c7 and primary RPE cell cultures, cells were incubated in mouse anti human CD46 (clone MEM258, Serotec) (1:50) in 3% normal goat serum (NGS) (Jackson Immunoresearch) at 4° C. for three hours prior to fixation. Cells were fixed at 4° C. in 10% NBF overnight. Secondary antibody detection was performed with Cy3 goat anti mouse (37.5 ng/ml) in 3% NGS for one hour. To detect CD46 in fixed 14 µm frozen sections and mouse eye-cups, samples were pre-treated with 6% NGS and incubated overnight at 4° C. in a 1:100 dilution of mouse anti human CD46 (clone E4.3, BD Pharmingen) containing 0.5% triton. Secondary detection was performed with Cy3 goat anti mouse (37.5 ng/ml) in 0.5% triton for one hour. To detect the MAC complex, samples were incubated with mouse anti human C5b-9 (clone aE11, Abcam) (1:100) containing 6% NGS and 0.05% triton for 2.5 hours. Secondary detection was performed with Cy3 goat anti mouse (37.5 ng/ml) containing 3% NGS and 0.05% triton for 1.5 hours.

Example 24

Expression of Human CD46 from Adenovirus Vectors in Human Embryonic Retinoblasts and Mouse Hepatocytes Human CD46 is a transmembrane protein ranging in molecular weight from about 48 kDa to about 68 kDa (Post et al. 1991 J Exp Med 174(1): 93-102). There are at least four human isoforms, each containing four conserved short consensus sequences (SCR), an O-glycosylated serine/threonine/proline rich area, a hydrophobic transmembrane portion, and an intracellular domain.

Figure 10A:
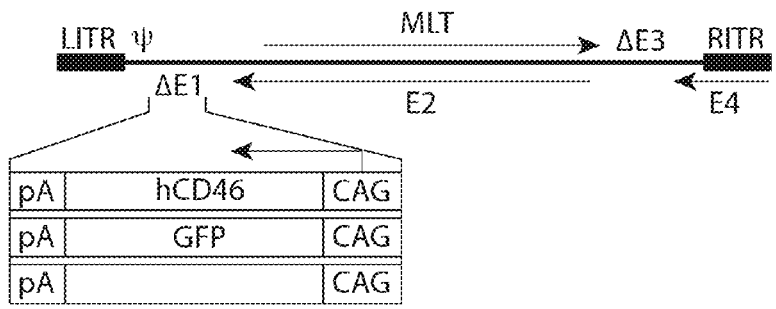
FIG. 10 panels A-C are a drawing and a set of photographs showing human CD46 expressed in HER cells and on the membrane of mouse Hepa 1c1c7 cells.
Figure 10B:
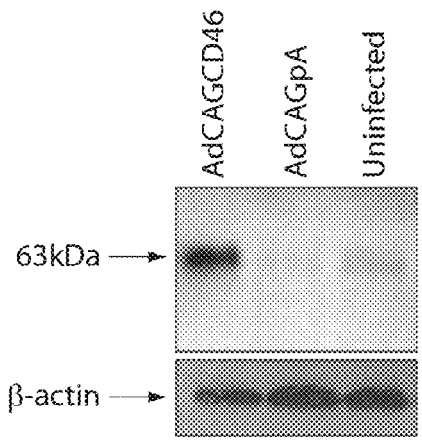
Figure 10C:
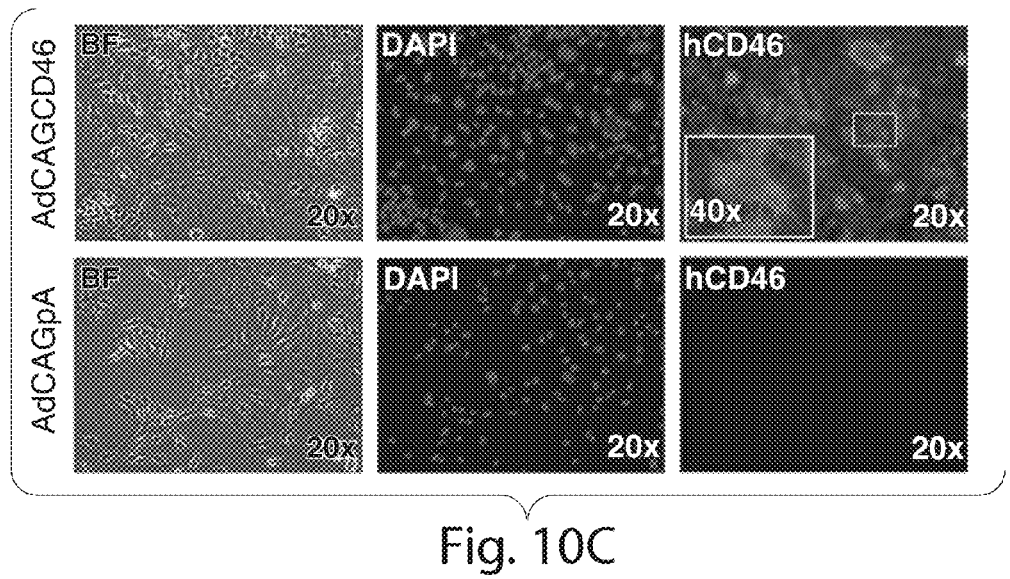

The ability of human CD46 (hCD46) to protect tissues from human complement-mediated insult was evaluated by cloning hCD46 into an adenoviral vector under the control of a chicken β actin promoter (CAG). The adenovirus vector strain encoding CD46 is identified as AdCAGCD46. A control adenovirus that does not have a transgene (AdCAGpA) and an adenovirus expressing GFP (AdCAGGFP) were also generated (FIG. 10 panel A).

Western blot analysis of lysates collected from AdCAGCD46-contacted human embryonic retinoblasts (HERs) showed expression of hCD46. A band at 63 kDa molecular weight was observed (FIG. 10 panel B), which corresponded to the predicted molecular weight of the BC isoform of hCD46 (Post et al 1991 174(1): 93-102). The majority of human cells express a detectable amount of CD46 (McNearney et al. 1989 J Clin Invest 84(2): 538-545) and lysates from AdCAGpA contacted HERs and uninfected control HERS showed a very light band at approximately 63 kDa molecular weight. A substantially greater amount of CD46 was expressed by cells transfected by AdCAGCD46 compared to cells transfected by AdCAGpA.

Immunocytochemistry was performed with non-permeabilized mouse hepatocytes (Hepa 1c1c7) transfected with either AdCAGCD46 or AdCAGpA. AdCAGCD46-transfected hepatocytes showed robust hCD46 expression at the site of the cell membrane. In contrast, no hCD46 was detected in AdCAGpA-contacted cells (FIG. 10 panel C). Thus, it was observed that cells transformed with ADCAGCD46 vector expressed substantial amounts of hCD46 on the cell membrane of contacted cells.

Example 25

AdCAGCD46 Protected Hepatocytes from the Alternative Complement Pathway

Human CD46 has a high affinity for binding C3b than for C4b, resulting in increased inhibition of convertase formation by the alternative pathway (Barilla-LaBarca et al. 2002 J Immunol 168(12): 6298-6304). The ability of AdCAGCD46 to protect cells from complement mediated cell lysis concomitantly from classical and alternative complement pathways was evaluated, in comparison to specific protection of cells only from alternative pathway-mediated cell lysis.

Hepa1c1c7 cells were pre-treated with either AdCAGCD46 or AdCAGpA for three days and then treated with either 25 µg/ml emmprin antibody followed by 10% NHS to activate both classical and alternative pathways, or MgEGTA-treated NHS for inhibition of the classical pathway (i.e., activation of the alternative complement only). Cell lysis was determined by FACs analysis using propidium iodide (PI) uptake. PI, an intercalating agent that fluoresces when bound to DNA, was obtained from Fluka BioChemica (Buchs, Switzerland). PI is excluded from viable cells and identifies non-living cells in a mixed population.

Complement activation was performed using cells in suspension rather than on a plate to eliminate the possibility that dead cells were escaping FACS analysis by separating from the plate. Forward and side scatter did not reveal any difference between these groups, indicating no difference in cell toxicity. Under the circumstances that both the classical and alternative pathways were activated, AdCAGCD46-contacted cells showed no significant protection from cell lysis compared to AdCAGpA-contacted cells (FIG. 11 panel A). However, under the circumstances of the classical pathway being inactivate (i.e., cell lysis occurring because of the alternative pathway), a 39±0.88% (p=0.008) reduction in the amount of PI uptake was observed for AdCAGCD46-contacted eyes compared to AdCAGpA contacted eyes (FIG. 11 panel B). Without being limited by any theory or mechanism of action, it is envisioned that the observed difference in PI uptake between AdCAGCD46 and AdCAGpA-contacted cells correlates with differences in amounts of membrane attack complex (MAC) deposited on the membranes of these cells.

To determine whether reduction if PI uptake correlates with reduced MAC staining, Hepa1c1c7 cells were contacted for three days with either AdCAGCD46 or AdCAGpA, and then the alternative pathway was activated by incubating the cells with 25 µg/ml emmprin followed by incubation in 10% NHS and MgEGTA. Amount of human MAC deposition was determined using a monoclonal antibody specific to the MAC C5b9 complex.

Cells contacted with AdCAGCD46 showed less MAC deposition on cellular surfaces (FIG. 11 panel C) than cells contacted with AdCAGpA. Most important, the morphology of the AdCAGCD46 contacted cells remained largely unaffected by MAC deposition compared to those cells transfected with AdCAGpA, which showed cell rounding indicating abnormal cellular morphology indicative of complement-mediated cell lysis. These data show that AdCAGCD46 protected cells from cell lysis caused by the alternative complement pathway.

Example 26

AdCAGCD46 Protected Mouse Primary RPE Cells from Alternative Pathway Mediated MAC Deposition MAC deposition has been observed on RPE cells in AMD patients and the alternative pathway has been implicated to play a pivotal role in this disease. Whether AdCAGCD46-contacted mouse primary RPE cells were protected from human MAC deposition mediated primarily by the alternative complement pathway was herein determined.

RPE cells are more resistant to MAC deposition than Hepa1c1c7 cells (Mizuno et al. 2001 Arthritis Rheum 44: 2425-2434), and require higher concentrations of antibody and serum. RPE cells were pre-incubated with 50 µg/ml emmprin followed by incubation with MgEGTA and 50% NHS. MAC deposition on RPE cells was detected by immunohistochemistry (IHC).

Figure 12A:
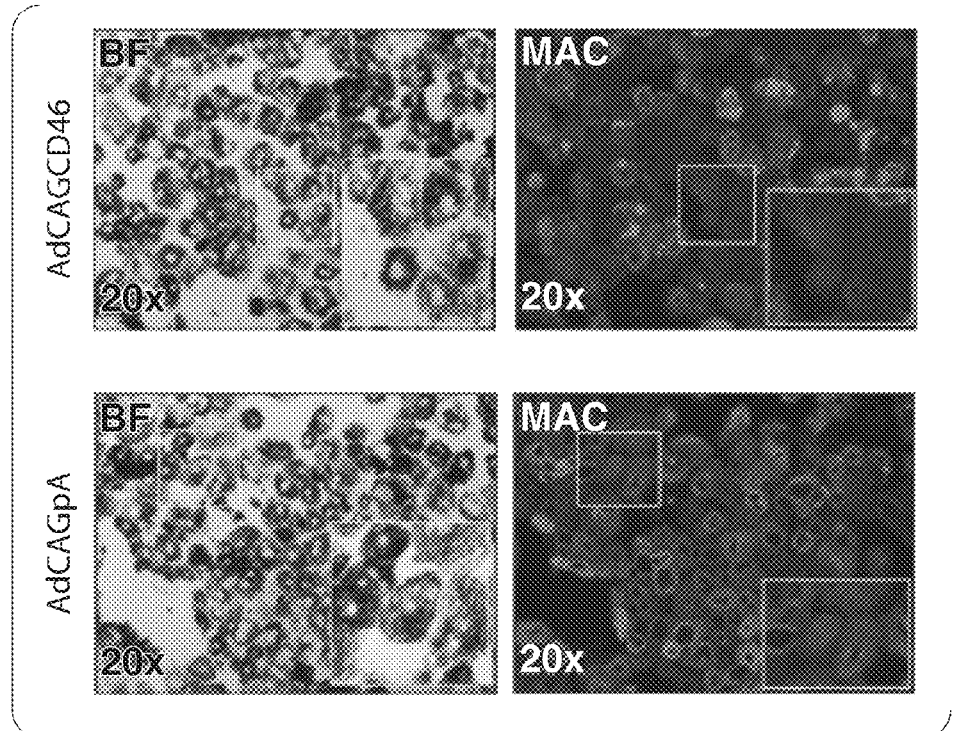
FIG. 12 panels A-B are a bar graph and set of photomicrographs showing that media conditioned by AdCAGCD46 contacted cells protected mouse primary RPE cells from alternative pathway mediated MAC deposition. Images and data are representative of three independent experiments performed in duplicate each time.
Figure 12B:
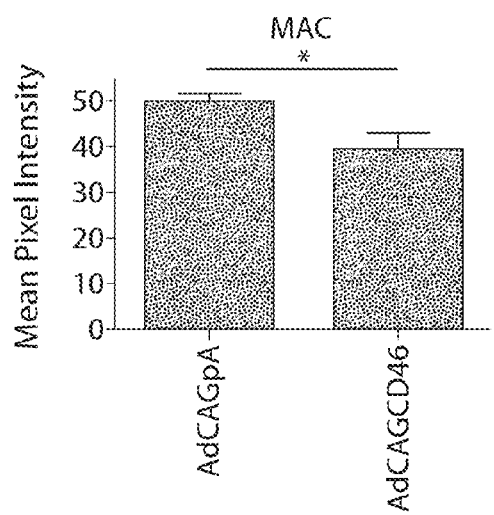

Quantification of MAC staining showed that AdCAGCD46 protected cells from the negative symptoms of the alternative complement pathway. A reduction of 21±1.9% (p=0.04) in MAC deposition intensity was observed for RPE cells contacted with AdCAGCD46 rather than AdCAGpA (FIG. 12 panels A and B).

Additional assays and testing was performed herein to ensure that the data showing reduced MAC staining for RPE cells contacted with AdCAGCD46 compared to hepatocytes contacted with AdCADCD46 was valid. The number of cells after the MAC staining assay was counted to ensure that the reduction in MAC was not caused by serum treatment differentially reducing the number of RPE cells. Equivalent numbers of cells remaining on the AdCAGCD46 treated slides and the AdCAGpA treated slides were observed. The AdCAGCD46-mediated reduction in MAC staining for RPE cells was less than that observed for hepatocytes. Whether the difference in MAC staining between RPE cells and hepatocytes was due to a lower infection rate of RPE cells and/or reduced expression of hCD46 was determined. The expression of hCD46 from AdCAGCD46 in mouse primary RPE cells was analyzed by IHC.

Figure 13:
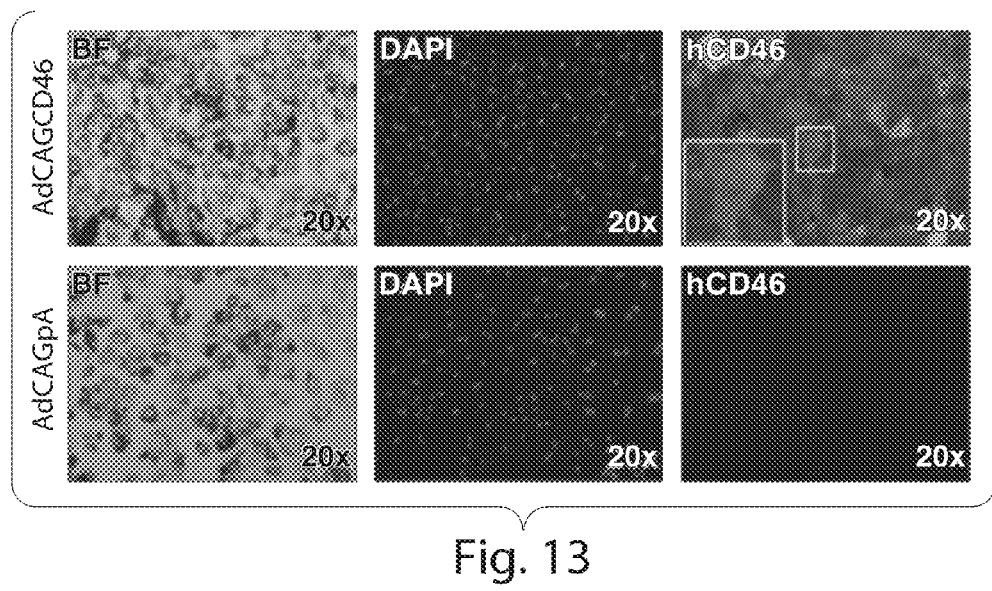
FIG. 13 is a set of photomicrographs showing that hCD46 is expressed in mouse primary RPE cells following transfection (or contacting) with AdCAGCD46. RPE cells were contacted with media conditioned by either AdCAGCD46 (top row) or AdCAGpA (bottom row) and were visualized with BF (left column) and stained with DAPI (middle column) or an antibody specific for human CD46 (right column). Data show that mouse primary RPE cells efficiently expressed hCD46 on their membranes following transfection with AdCAGCD46. Little or no hCD46 was detectable in cells transfected with AdCAGpA.

AdCAGCD46 contacted cells showed almost 100% transduction and showed strong expression of hCD46 on the cell membrane, and AdCAGpA contacted cells had no detectable hCH46 expression (FIG. 13 panel A). Thus, decreased MAC staining for AdCAGCD46 contacted RPE cells compared to AdCAD46 contacted hepatocytes was not a result of differential serum treatment effects, adenovirus infection rates, or hCD46 expression.

Without being limited by any theory or mechanism of action, it is envisioned that the reduced inhibition of MAC deposition observed for AdCAGCD46 contacted RPE cells was due to increased amount of serum antibody and therefore increased activation of classical pathway required to activate complement on this cell type.

Example 27

AdCAGCD46 Expression of hCD46 on Basal and Lateral Surfaces of Mouse RPE Cells

CD46 is expressed in the human eye on both the basal and lateral surfaces of RPE cells (Kimberley et al. 2007 Mol Immunol 44: 73-81). To determine if hCD46 is expressed in a similar pattern in mouse RPE cells in vivo, adenovirus vectors were injected into the sub-retinal space of adult mice. Either 1 µl of an empty vector control mixture containing 9 parts AdCAGpA (total $5 \times 10^7$ particles) and 1 part AdCAGGFP (total $1 \times 10^6$ particles), or CD46 vector containing 9 parts AdCAGCD6 (total $5 \times 10^7$ particles) and 1 part AdCAGGFP (total $1 \times 10^6$ particles) was injected subretinally. Unless indicated otherwise, assays herein were performed in duplicate at least 3 times. Error bars represent SD from the mean. Significance was calculated using student's t-test. Eyes were harvested eight days following injection and were examined for expression of hCD46.

Flat mounts of the eye-cups contacted with a mixture of AdCAGCD6 and AdCAGGFP revealed robust expression of hCD46 in RPE cells with increased intensity of expression observed at the intercellular junctions (FIG. 14 panel A). Cross sections were taken through the injection site of the eyes and compared with an un-injected region of the eye-cup to determine whether hCD46 expression was present also on the basal and lateral surfaces of RPE cells. The injected eye region showed hCD46 expression located primarily on the basal and lateral surface of the RPE cells (FIG. 14 panel B). The observed hCD46 expression pattern on murine tissues was comparable to the previously observed hCD46 expression pattern in human eyes (Kimberley et al. 2007 Mol Immunol 44: 73-81).

Example 28

AdCAGCD46 Protected Mouse RPE Cells from Alternative Pathway Mediated MAC Deposition Whether hCD46 expressed from an adenovirus on mouse RPE cells in vivo offered protection from human MAC deposited by the alternative pathway was determined.

Adult murine subjects were injected in the sub-retinal space with either a mixture of AdCAGCD46 and ADCAG-GFP or a mixture of AdCAGpA and AdCAGGFP. Each mixture included adenovirus expressing GFP to facilitate identification the injection site. Eyes were enucleated eight days following the injection, and the lens, cornea, and retina were removed to expose the RPE cells. Each eyecup was treated with 140 µg/ml emmprin followed by 50% NHS and MgEGTA. MAC formation was detected using a monoclonal antibody to the C5b9 complex.

Data show that prior to serum treatment, the GFP expression observed was robust in each of the eyecups and after serum treatment GFP expression was patchy due to damage of RPE cells by the serum. Within the region of AdCAGCD46 expression there was a significant reduction in the amount of MAC staining relative to AdCAGpA injected eyes (FIG. 15 panels A and B). Data show a 24±4.5% (p=0.0001) reduction in MAC deposition in AdCAGCD46 contacted eyes compared to AdCAGpA contacted eyes (FIG. 15 panel C). To determine whether MAC was deposited equally on the apical and basal surface of the RPE cells, MAC staining assays were performed on un-injected eyes and cross sections through the RPE were prepared. Data show that MAC was deposited almost exclusively on the apical surface of the RPE cells (FIG. 15 panel D).

It was observed that contacting ocular tissues with AdCAGCD46 provided adenovirus-mediated delivery of hCD46 to the basal and lateral surfaces of RPE cells. AdCAGCD46 specifically protected cells from alternative pathway mediated MAC damage and allowed the classical pathway to function unhindered.

A recombinant adenovirus carrying a gene encoding CD55 was engineered, and was tested to determine protection of ocular cells from MAC staining.

Example 29

AdCAG55 Construction and Expression on Ocular Cells

Figure 16A:
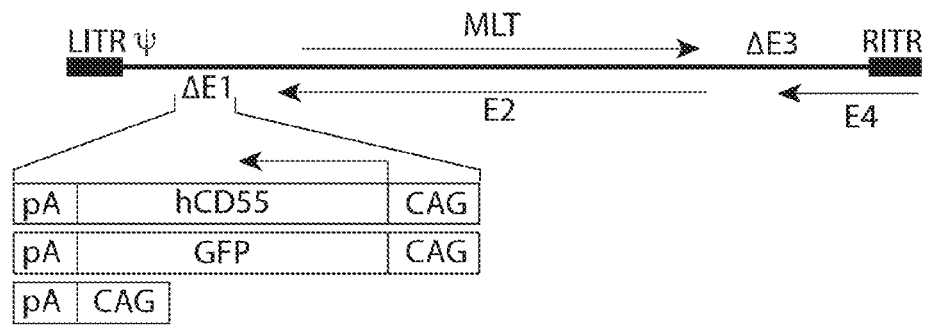
FIG. 16 panels A-C are a drawing and a set of photomicrographs showing that human CD55 (hCD55) expressed in vitro from an adenovirus vector was processed correctly and localized in the cell membrane.
Figure 16B:
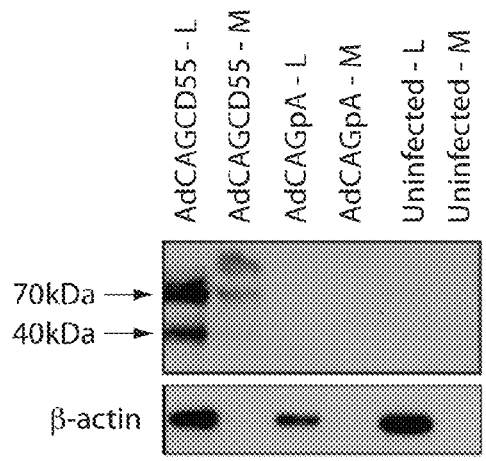
Figure 16C:
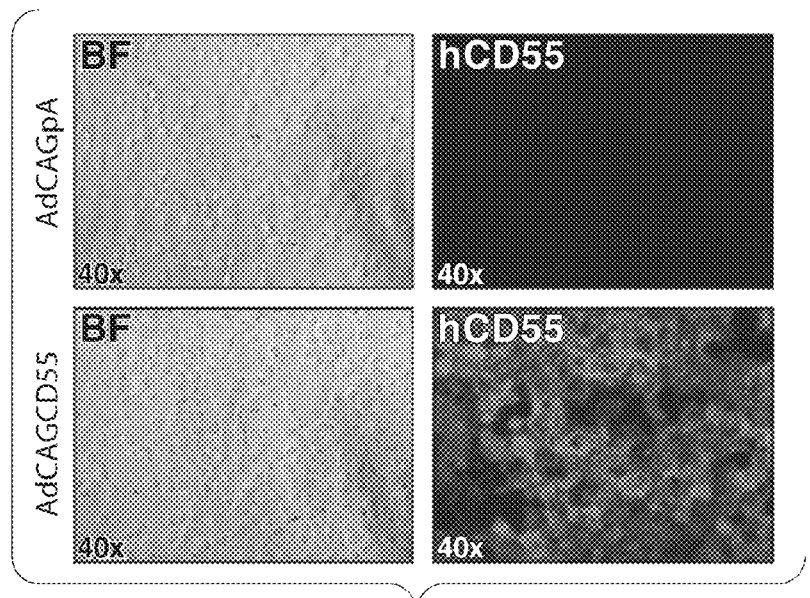

An adenovirus vector expressing human CD55 (hCD55) regulated by a chicken β-actin promoter was constructed and is shown in FIG. 16 panel A. Recombinant adenovirus serotype 5 (Ad5) expressing human CD55 (hCD55) was generated by cloning a Sal I/Not I fragment from a plasmid containing the human CD55 cDNA (ATCC 5830488; GenBank ID: BC001288; SEQ ID NO: 5) into pCAGEN generating pCAGCD55. An Spe I/BamHI fragment containing the entire CD55 expression cassette was inserted into pShuttle (He et al. 1998 Proc Natl Acad Sci USA 95: 2509-2514). The pShuttle was co-transformed with pAdEasy1 into BJ5183 cells to rescue the plasmid pAdCAGCD55 (Ibid.). The hCD55-expressing virus was rescued by transfection of 911 cells with PacI linearized pAdCAGCD55 and virus was purified using the adenopure purification kit (Puresyn, Inc.). Viral titer was determined using a spectrophotometer set at 260λ. Control recombinant Ad5 vector expressing GFP (AdCAGGFP) and a vector Ad5 devoid of a transgene (AdCAGpA) were also constructed (Ramo et al. 2008 Invest Ophthalmol Vis Sci 49: 4126-4136).

Expression and processing of hCD55 was observed in AdCAGCD55-contacted human embryonic retinoblasts (HERS). Human embryonic retinoblasts were contacted with either AdCAGCD55 or AdCAGpA at a multiplicity of infection (MOI) of 1000 for 24 hours. The cell lysate and medium were collected and electrophoresed through a 12.5% tris HCL pre-cast gel (Biorad) under reducing conditions. Following transfer to a polyvinylidene fluoride (PVDF) membrane (Millipore) and blocking in 5% skim milk (Becton Dickinson, Sparks, Md.), the membrane was probed for hCD55 with a 1:1000 goat anti-human CD55 antibody (R&D Systems) and a 1:5000 secondary horseradish peroxidase-conjugated bovine anti-goat antibody (Jackson ImmunoResearch Laboratories, INC.). The signal was detected using a PIERCE chemiluminescent kit. After stripping and blocking as above, the same membrane was probed for β-actin with a 1:5000 mouse anti-β-actin monoclonal antibody (Clone AC-15; Sigma-Aldrich). Secondary detection was performed as described above.

Examination of cell lysates by immunoblot revealed both the unglycosylated 40 kDa hCD55 precursor, and the mature 70 kDa protein (FIG. 16 panel B). Low levels of the unglycosylated, glycosylated and one species of higher molecular weight hCD55 were also detected in the media of AdCAGCD55-contacted cells. Localization of hCD55 to the cell membrane was determined by immunostaining of non-permeabilized mouse hepa1c1c7 cells contacted with AdCAGCD55 (FIG. 16 panel C).

Example 30

Adenovirus-Delivered hCD55 Protects Mouse Hepa1c1c7 Cells from Complement-mediated Lysis Ability of AdCAGCD55-mediated to protect murine cells from complement-mediated damage was determined with a human serum-mediated cell lysis assay. Hepa1c1c7 cells were contacted with each of AdCAGCD55 and AdCAGpA at an MOI of 1000 for 65 hours in α-MEM/10% FBS. Cells were washed with 1× PBS and dissociated with TrypLE Express (GIBCO). Cells were collected by centrifugation at 1200 RPM/4° C. and were re-suspended in ice-cold gelatin veronal buffer with $Ca^{2+}$ and $Mg^{2+}$ ($GVB^{2+}$) (Complement Technology, Tyler, Tex.). A solution of 10% normal human serum (NHS; Sigma) or 10% heat-inactivated NHS (HI-NHS; 56° C. for 1 hour) was added to $5\times10^5$ cells for one hour at 37° C. to activate complement pathways. Lysed cells were labeled by propidium iodide (PI), counted by FACS (FACSCalibur; Becton Dickinson, Franklin Lakes, N.J.), and were analyzed for PI uptake (CellQuest Pro software; Becton Dickinson).

Figure 17A:
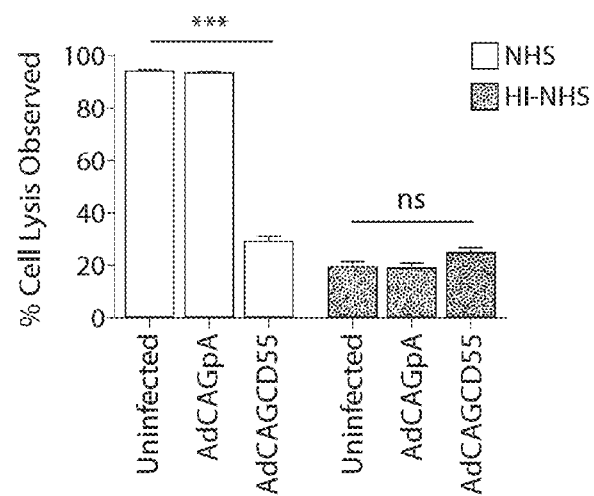
FIG. 17 panels A-B are a bar graph and a set of print outs showing that adenovirus vectors expressing hCD55 protected mouse hepa1c1c7 cells from complement-mediated cell lysis.
Figure 17B:
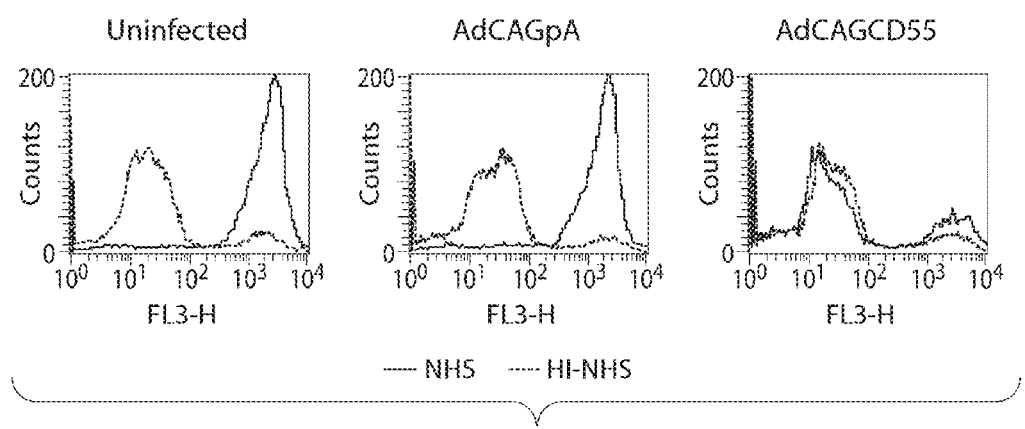

It was observed that NHS AdCAGCD55 significantly protected mouse hepa1c1c7 cells from cell lysis (FIG. 17 panel A open bars). Complement-mediated cell lysis in the AdCAGpA-contacted or uninjected cells was 93.22%±0.65% and 94.00%±0.47%, respectively. Most important, cell lysis for AdCAGCD55-contacted cells was significantly lower, 29.29%±1.98% (p<0.0001).

Each of the HI-NHS contacted tissues showed no significant differences in cell lysis (FIG. 17 panel A closed bars). Complement mediated cell lysis for AdCAGCD55 contacted cells was 24.53%±2.26%, for AdCAGpA-contacted cells was 18.99%±2.03%, and for uninjected cells was 19.58%±2.11% respectively (p=0.1514). Without being limited by any theory or mechanism of action, it is envisioned that the percentage of cell lysis observed following incubation in HI-NHS (approximately 20%) indicated a baseline level of cell damage due to cell manipulation during the assay and accounted for most of the cell damage observed in AdCAGCD55-contacted cells incubated with NHS. A representative set of FACS printouts is shown in FIG. 17 panel B for uninjected control cells (left graph) and cells contacted with either AdCAGpa (middle graph) or AdCAGCD55 (right graph) treated with NHS or HI-NHS. These data show that AdCAGCD55 conferred significantly protection of mouse hepa1c1c7 cells against human complement-mediated cell lysis. FACS analysis data of AdCAGCD55-contacted cells were comparable for treatment with either NHS or HI-NHS, indicating similar low levels of protection from cell lysis.

Example 31

Adenovirus-delivered hCD55 Protects Mouse Cells from Human MAC Deposition

Complement-mediated cell lysis is caused by the formation of MAC on the plasma membrane. Data herein show that hCD55 regulates all three complement pathways by binding and accelerating the decay of C3 convertase in the classical and alternative pathways, preventing downstream MAC deposition on biological surfaces.

Hepa1c1c7 were transfected with AdCAGCD55 or AdCAGpA at an MOI of 1000 for 72 hours in α-MEM/10% FBS in poly-D-lysine-coated chamber slides (Becton Dickinson). Cells were washed with 1× PBS and were then incubated with 10% NHS or 10% HI-NHS in $GVB^{2+}$ for five minutes. Cells were then washed three times with cold 1× PBS and incubated with 1:100 mouse anti-human C5b-9 (Clone AE11, Abcam) in 6% normal goat serum (NGS Jackson ImmunoResearch Laboratories, INC.) for 2.5 hours prior to fixation with 3.7% formaldehyde (MP Biomedicals, Solon, Ohio). Cells were washed and probed with 1:200 secondary Cy3-conjugated donkey anti-goat IgG (Jackson ImmunoResearch Laboratories, INC.) in 3% NGS for 1.5 hours.

It was observed that AdCAGCD55-contacted cells showed significantly less staining for MAC compared to both AdCAGpA-contacted cells (FIG. 18 panel A) and uninfected cells. Images were captured using a microscope and camera and grayscale images were analyzed using Image J1.41× (National Institute of Health, USA) for degree of MAC immunofluorescence in arbitrary units. Representative areas were selected with the polygon selection tool and mean fluorescence intensity/pixel was measured. Background fluorescence in the hepatocyte images was subtracted from the mean fluorescence measurements.

Without being limited by any particular theory or mechanism of action, it is here envisioned that that AdCAGCD55 inhibited C3 convertase and successfully attenuated downstream formation and deposition of MAC on cell membranes.

Figure 18A:
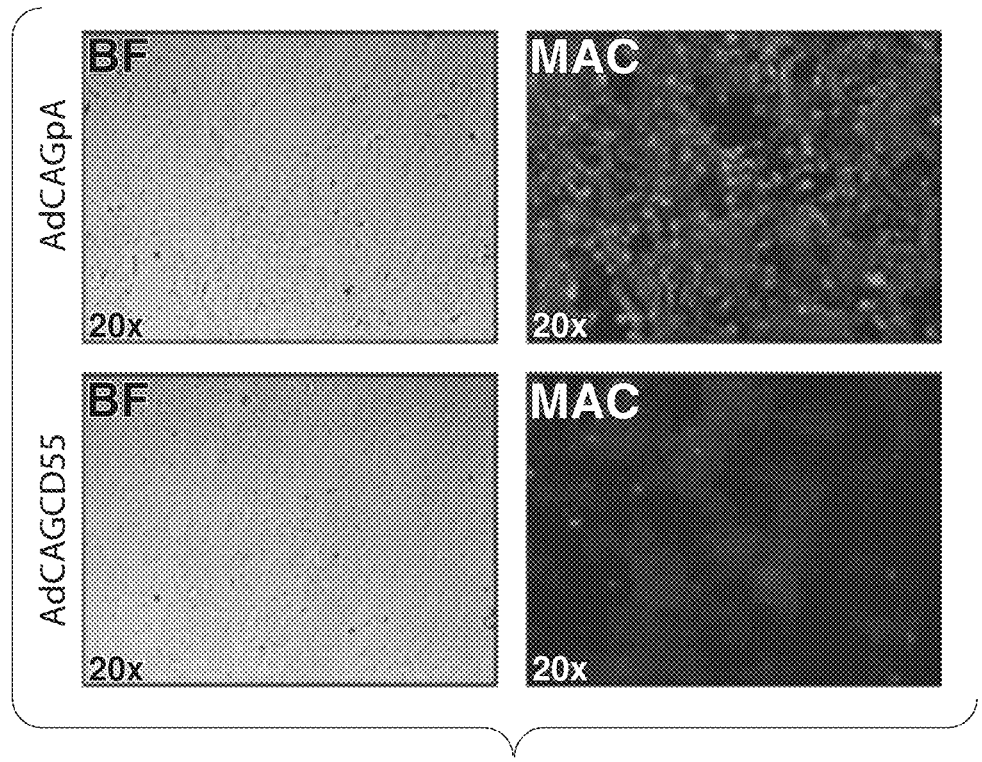
FIG. 18 panels A-B are a set of photomicrographs and a bar graph showing that AdCAGCD55 protected mouse hepa1c1c7 cells from complement-mediated MAC deposition.
Figure 18B:
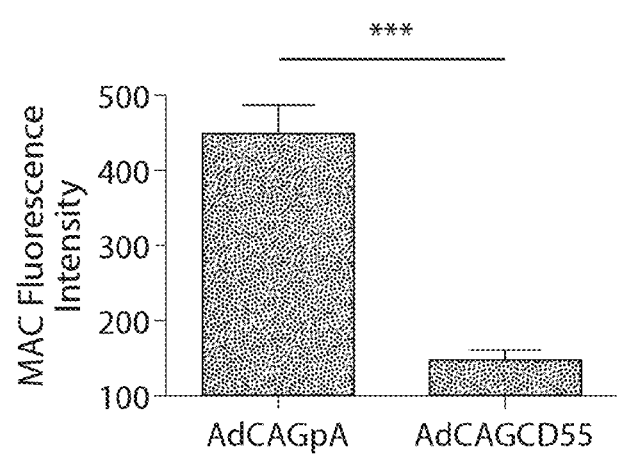

Quantification of fluorescence intensity showed a 67.1% decrease in MAC on murine cells expressing hCD55 relative to those not expressing hCD55 (FIG. 18 panel B). Mean fluorescence intensity for AdCAGpA-contacted cells was 449.9±38.1 and for AdCAGCD55-contacted cells was 148.0±13.1, respectively (p<0.0001). Thus, human CD55 protected murine hepatocytes from human MAC deposition.

Example 32

Adenovirus-delivered hCD55 Protects Murine Ocular Tissues from MAC Deposition

Deposition of MAC has been observed on RPE cells in AMD patients (Johnson et al. Exp Eye Res 70: 441-449). Efficacy of hCD55-mediated protection of RPE cells against MAC deposition was determined.

Subretinal injections were performed on mouse subject as described herein using the transcleral-transchoroidal approach with a 32-gauge needle attached to a 5 µL glass syringe. Flatmounts of eyecups from eyes were pretreated by injection with a mixture of control vectors AdCAGpA and AdCAGGFP (9:1 ratio), or a mixture of vectors AdCAGCD55 and AdCAGGFP (9:1 ratio). A total of 1 µl of each mixture containing a total 1×10$^8$ viral particles was injected into each eye.

Previous studies have shown that hCD55 is generally localized at the nerve fiber layer in healthy human retinas (Vogt et al. 2006 Eye Res 83: 834-840), and is not observed on the RPE. Expression and localization of hCD55 was analyzed in murine RPE cells. Subjects were sacrificed with carbon dioxide six days after subretinal injection and eyes were enucleated. The lens and cornea were removed and the eye cup incubated in GVB$^{2+}$ containing 140 µg/mL goat anti-mouse emmprin (R&D Systems) for one hour at 4° C. 50% NHS or HI-NHS was added to the GVB$^{2+}$/emmprin solution and incubated for 15 minutes at 37° C. Samples were washed in cold 1× PBS and fixed overnight in 3.7% formaldehyde. Eye cups with intact RPE were immunostained with 1:100 goat anti-human CD55 and a 1:200 secondary Cy3-conjugated donkey anti-goat (Jackson ImmunoResearch Laboratories, INC.) prior to flat mounting to detect successful infection of RPE by AdCAGCD55 and expression of hCD55. Immunostained eye cups were embedded in Tissue-Tek (Sakura Finetek, Torrance, Calif.) prior to collecting 14 µm frozen sections on glass slides. Fixed eye cups were immunostained with 1:100 mouse anti-human C5b-9, flat-mounted and cover-slipped to visualize MAC deposition on mouse RPE. Image J was utilized to quantify MAC deposition on mouse RPE.

Figure 19A:
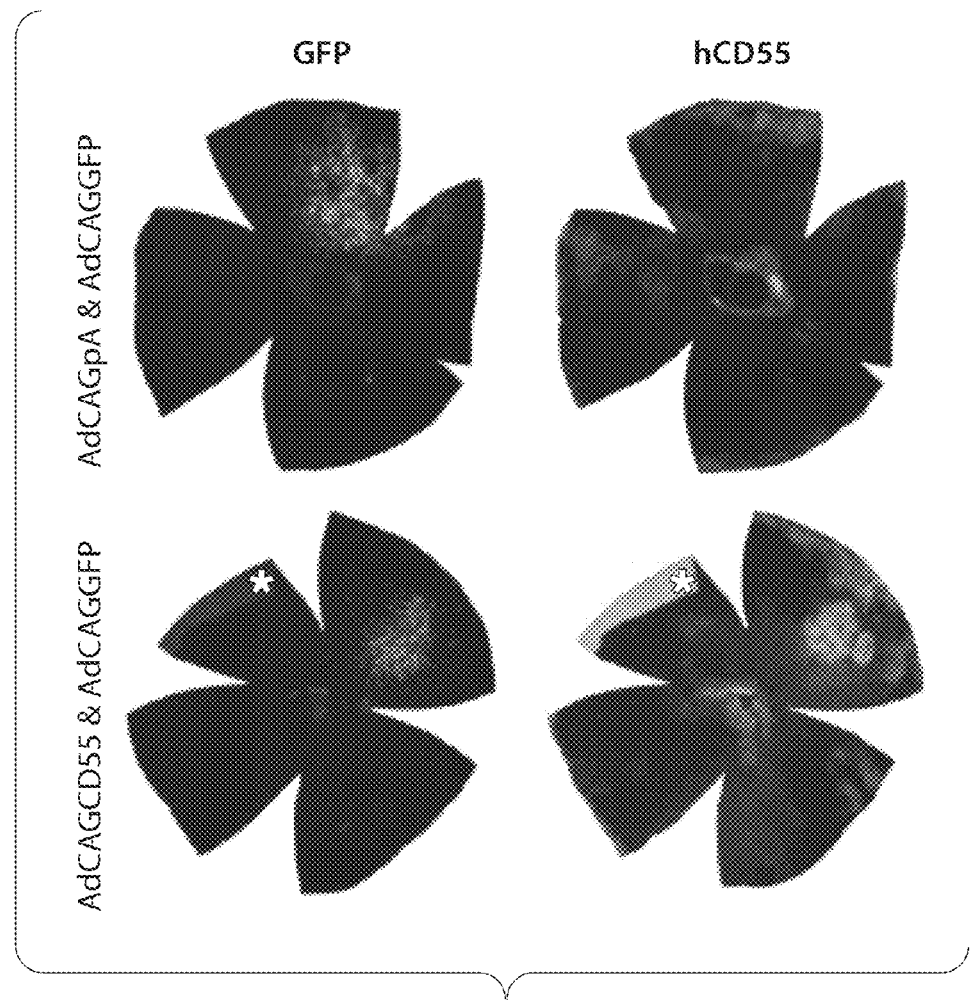
FIG. 19 panels A-B are a set of photomicrographs showing that subretinal injection of AdCAGCD55 to murine eyes caused localization of hCD55 to the apical, basal and lateral membrane of RPE cells. Flatmounts of eyecups were pretreated by injection with a mixture of vectors AdCAGpA and AdCAGGFP (9:1 ratio) or a mixture of vectors AdCAGCD55 and AdCAGGFP (9:1 ratio). Cells were contacted six days post-injection with 10% NHS for five minutes, and then were visualized with BF and stained for hCD55 expression using a protein specific monoclonal antibody.
Figure 19B:
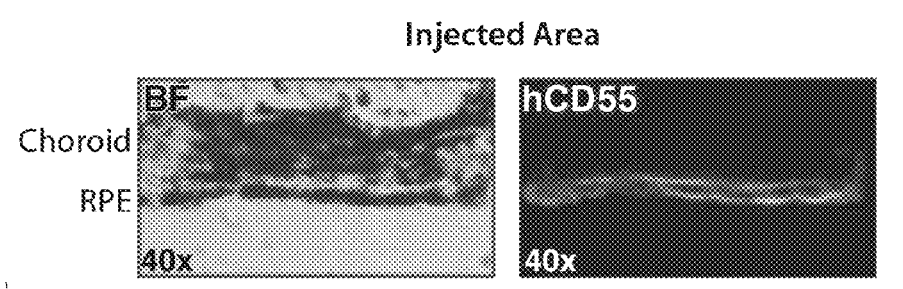

Immunohistochemistry analysis of sclera/choroid/RPE flat mounts from AdCAGCD55 and AdCAGGFP-contacted eye cups showed intense hCD55 staining on the membrane of RPE cells coincident with GFP. No significant hCD55 staining was detected on eye cups of mice that were injected with control vectors AdCAGpA and AdCAGGFP (FIG. 19 panel. A). Analysis of cross sections through the injection site showed that hCD55 was expressed on the apical, basal and lateral membrane of RPE cells (FIG. 19 panel B).

To examine whether this efficiency of hCD55 expression on mouse RPE cells would protect the cells from complement-mediated MAC deposition, either a mixture of AdCAGCD55 and AdCAGGFP or a mixture of AdCAGpA and AdCAGGFP was injected into the sub-retinal space of adult mice. AdCAGGFP was included in the mixture to identify the site of injection. Eyes were harvested six days following injection and the cornea, lens, and retina, were removed. Each resulting eyecup was then contacted with an anti-mouse emmprin antibody in 50% NHS for 15 minutes. Emmprin was shown above to be necessary for activation of complement on RPE cells (see also Ramo et al. 2008 Invest Ophthalmol Vis Sci 49: 4126-4136). Eyecups were stained for human MAC with the antibody directed against C5b-9.

Figure 20A:
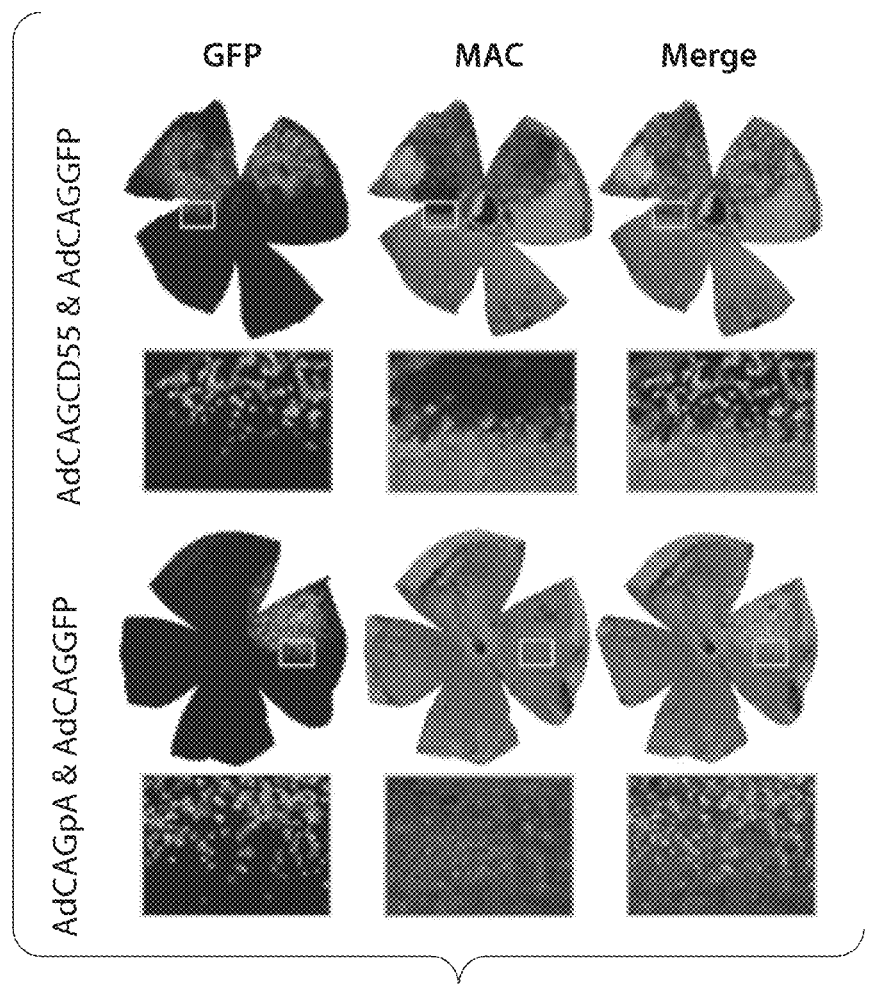
FIG. 20 panels A-B are a bar graph and a set of photomicrographs showing protection against human MAC deposition as a result of adenovirus vector expressing hCD55 delivered to mouse RPE cells in vivo. Flatmounts of eyecups were pretreated by injection with a mixture of vectors AdCAGpA and AdCAGGFP (9:1 ratio) or a mixture of vectors AdCAGCD55 and AdCAGGFP (9:1). Cells were contacted six days post-injection with 10% NHS for five minutes, and were then visualized for GFP fluorescence and stained for MAC.
Figure 20B:
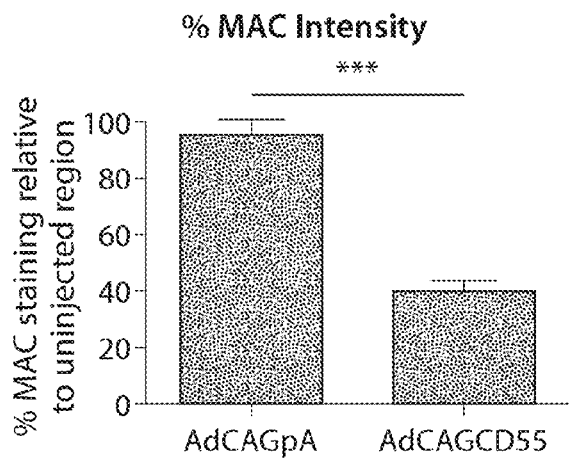

Eye cups contacted with a mixture of AdCAGCD55 and AdCAGGFP showed significantly less MAC deposition on the RPE within the region of injection (FIG. 20 panel A) than the uninjected region of the same eyecup. It was observed that contacting eyes with a mixture containing AdCADCD55 resulted in eyes having no difference in the intensity of MAC deposition within the injected area compared to the uninjected regions of the eyecup. AdCAGCD55-contacted RPE cells were relatively healthy and displayed normal cell morphology to the extent discernible at the magnifications (FIG. 20 panel A top row). In contrast, RPE cells contacted with a mixture of control vectors AdCAGpA and AdCAGGFP were observed to have lost hexagonal cell morphology, which indicated MAC staining and complement mediated cell lysis (FIG. 20 panel A bottom row). Quantification of the intensity of MAC staining showed a significant reduction in MAC formation (55.74%±5.99%) on the RPE cells from eyecups contacted with AdCAGCD55 and AdCAGGFP compared to RPE cells from eyecups contacted with AdCAGpA and AdCAGGFP, p<0.0001 (FIG. 20 panel B).

It is shown herein that adenovirus mediated delivery of hCD55 to murine RPE protected ocular tissues against human complement. Expression of hCD55 using the methods and compositions described herein is an effective therapy for retinal disorders such as AMD, and hCD55 is an effective therapeutic agent.

Example 33

STAC Construct and Expression Vector

Figure 21:
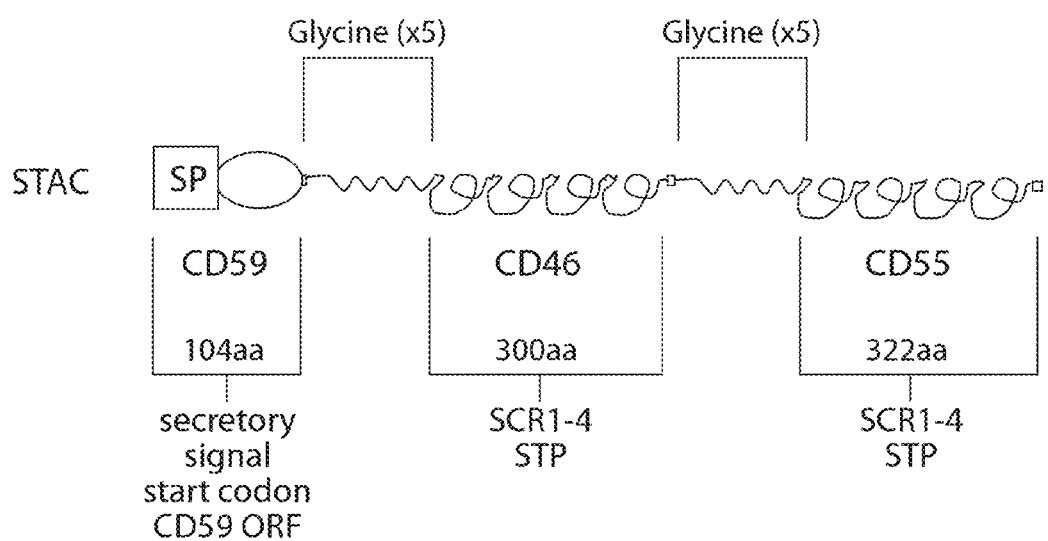
FIG. 21 is a drawing showing a nucleotide sequence of a gene encoding a STAC protein having a genetic fusion of amino acid sequences of human CD46, human CD55, and human CD59 proteins. The nucleotide sequence encodes a start codon, a secretory signal and complementary regulatory domains of the CD59 protein amino acid sequence of 104 amino acid open reading frame (ORF). The nucleotide sequence further encodes a linker having five glycines and the CD46 protein amino acid sequence of 300 amino acids including four short consensus repeat (SCR) domains/motifs and a serine/threonine/proline (STP) rich domain. The nucleotide sequence further encodes a second linker of five glycines and the CD55 protein amino acid sequence of 322 amino acids including four SCR domains and a STP rich domain followed by two stop codons (TGA).

A STAC protein was constructed as described herein having the complement regulatory domains of each of CD46, CD55, and CD59 proteins (FIG. 21), with the native secretory signal of CD59 at the N-terminus. The STAC protein gene sequence was designed using a modified sequence of each complement regulator in an attempt to minimize overall size of the protein by eliminating domains considered not useful for complement regulation. The SCR domains of CD46 and CD55 are involved in complement control and the serine threonine proline (STP) region is heavily glycosylated (Medof et al. 1987 Proc Natl Acad Sci USA 84: 2007-2011; and Xing et al. 1994 Immunology 83: 122-127), and is involved in protein stability. The majority of amino acids of the STP region were removed and the amino acid sequence of the full-length SCR domains for each regulator was retained. Glycines linkers were added to separate each complement regulator domain. Glycine is the smallest amino acid and accordingly likely to minimize steric hindrance after protein folding. The amino acid sequence of STAC protein (SEQ ID NO: 1) is shown below:

MGIQGGSVLFGLLLVLAVFCHSGHSLQCYNCPNPTADCKTAVNCSSDFDA

CLITKAGLQVYNKCWKFEHCNFNDVTTRLRENELTYYCCKKDLCNFNEQL

EGGGGGCEEPPTFEAMELIGKPKPYYEIGERVDYKCKKGYFYIPPLATHT

ICDRNHTWLPVSDDACYRETCPYIRDPLNGQAVPANGTYEFGYQMHFICN

-continued

```
EGYYLIGEEILYCELKGSVAIWSGKPPICEKVLCTPPPKIKNGKHTFSEV

EVFEYLDAVTYSCDPAPGPDPFSLIGESTIYCGDNSVWSRAAPECKVVKC

RFPVVENGKQISGFGKKFYYKATVMFECDKGFYLDGSDTIVCDSNSTWDP

PVPKCLKVGGGGGDCGLPPDVPNAQPALEGRTSFPEDTVITYKCEESFV

KIPGEKDSVICLKGSQWSDIEEFCNRSCEVPTRLNSASLKQPYITQNYFP

VGTVVEYECRPGYRREPSLSPKLTCLQNLKWSTAVEFCKKKSCPNPGEIR

NGQIDVPGGILFGATISFSCNTGYKLFGSTSSFCLISGSSVQWSDPLPEC

REIYCPAPPQIDNGIIQGERDHYGYRQSVTYACNKGFTMIGEHSIYCTVN

NDEGEWSGPPPECRGKSLTSKVPPTVQKPTTVNVPTTEVSPTSQKTTTKT

TTPNAQATRSTPVSRTTKHFHETTPNKGSGTTSGTT
```

Figure 22A:
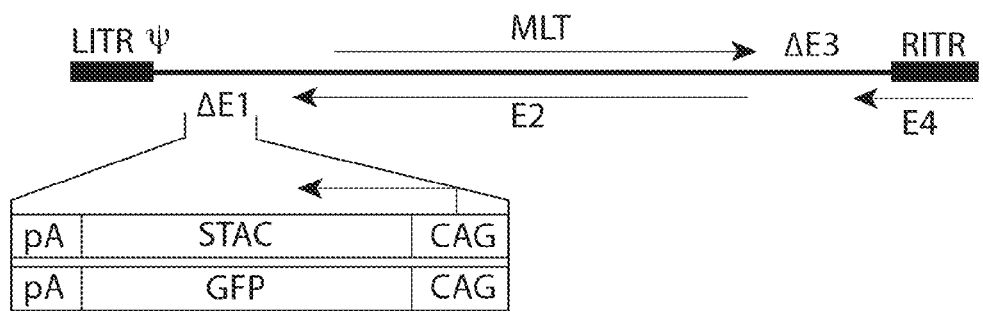
FIG. 22 panel A is a drawing showing construct AdCAGSTAC serotype 5 adenovirus vector expressing a gene encoding STAC protein under control of the CAG promoter, and construct AdCAGGFP expressing GFP under control of the CAG promoter. Symbols used: CAG, cytomegalovirus chicken β-actin β-globin promoter; pA, polyadenylation signal; LITR, left inverted terminal repeat; RITR, right inverted terminal repeat; Ψ, Ad packaging signal; MLT, major late transcript; E, early region labels.
Figure 22B:
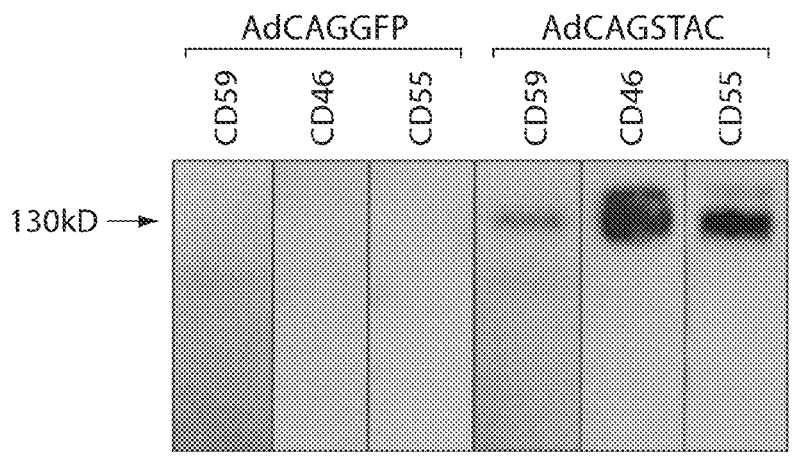

The transgene encoding the STAC protein was placed into the deleted E1 region of an adenovirus vector under control of a chicken beta actin promoter (AdCAGSTAC). A GFP negative control vector (AdCAGGFP) was also constructed. See FIG. 22 panel A.

Human RPE cells (ARPE19) were contacted with these vectors herein to determine whether AdCAGSTAC would be expressed and secreted, and have the relevant CD46, CD55, and CD59 domains. The conditioned-media were collected and were probed by western blot using individual antibodies specific to extra-cellular domains of each of human CD59, human CD46, and human CD55 respectively (See FIG. 21 panel B).

A strong band/signal was observed at 130 kilodaltons (kDa or KD) using each of the anti-CD59, -CD46, and -CD55 antibodies, and a faint band was observed at 150 KD. The two bands are interpreted as different glycosylation states for the STAC protein as a portion of the STP regions of the distinct complement regulators were retained, and are sites of N-linked and O-linked glycosylation.

Example 34

STAC Protects Hepa-1c1c7 Cells from Complement Activity

ARPE19 cells were contacted with either AdCAGSTAC or AdCAGGFP and media were collected to test the ability of STAC protein to prevent MAC deposition. The media were transferred to a plate having hepa-1c1c7 cells. Complement was then activated by adding 10% normal human serum (NHS) or 10% heat inactivated (Hi)-NHS to the cells.

Figure 23A:
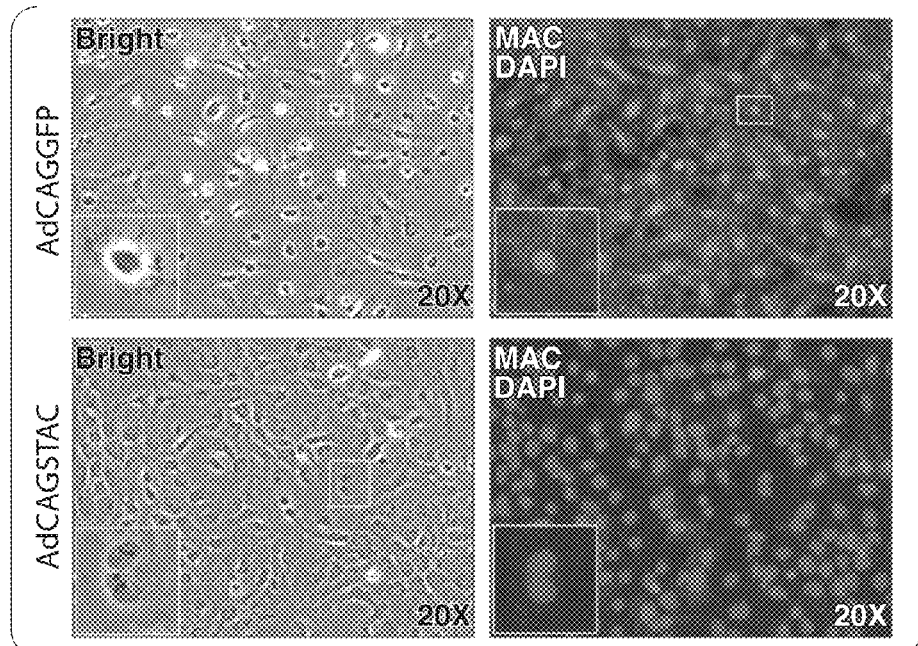
FIG. 23 panels A-C are a set of photomicrographs and data graphs showing that medium conditioned by AdCAGSTAC-contacted ARPE19 cells protected mouse hepa-1c1c7 cells from complement-mediated injury. Images and data are representative of three independent experiments performed in duplicate each time.
Figure 23B:
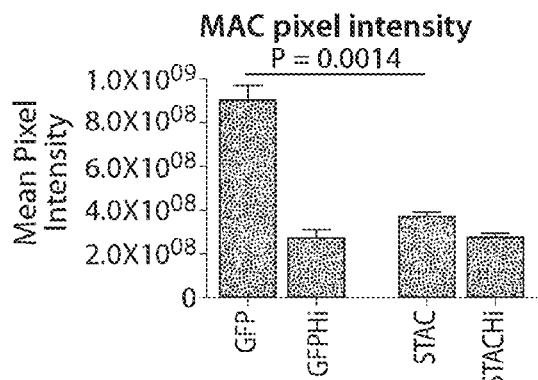
Figure 23C:
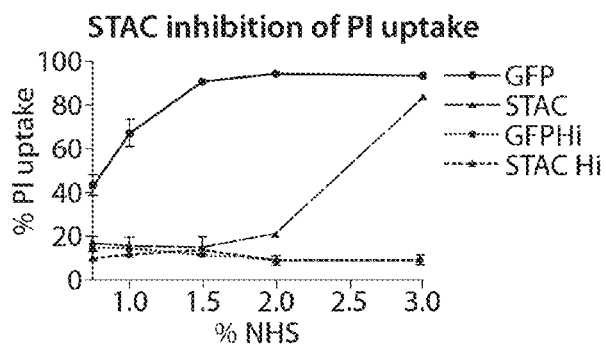

FIG. 23 panel A shows a representative photomicrograph of hepa-1c1c7 cells treated with NHS and media conditioned with AdCAGGFP or AdCAGSTAC, respectively. The morphology of the cells in AdCAGGFP-conditioned media changed dramatically compared to cells in AdCAGSTAC-conditioned media as viewed using DIC microscopy and an overlay of MAC/DAPI staining due to complement-mediated action in this system. The photomicrographs of the AdCAG-GFP-conditioned media show distinct indicia of cell lysis caused by complement activation (FIG. 23 panel A top row). Most important, the morphology of the cells contacted with AdCAGSTAC-conditioned media remained relatively unchanged with (See FIG. 23 panel A bottom row inset). Cells contacted with AdCAGSTAC-conditioned media appeared undamaged, and defined cell boundaries and normal hexagonal morphology were observed.

Analysis of the MAC pixel intensity of the hepa-1c1c7 cells contacted with NHS or HI-NHS shows that the mean pixel intensity of representative regions of the mice perfused with NHS was about twice that of the average overall intensity of mice perfused with HI-NHS (FIG. 23 panel B). Therefore contacting the cells with NHS resulted in two-fold greater MAC deposition than contacting the cells with HI-NHS.

Analysis of the MAC pixel intensity of the hepa-1 c1c7 cells contacted with NHS showed a reduced amount of MAC deposition for cells contacted with AdCAGSTAC-conditioned media compared to cells contacted with AdCAGGFP-conditioned media. Cells incubated with NHS and AdCAG-STAC conditioned-media showed a 68% decrease in the MAC pixel intensity and MAC deposition on the surface of the cell compared to cells contacted with NHS and AdCAG-GFP-conditioned media. See FIG. 23 panels A and B. Hepa-1c1c7 cells treated with controls of HI-NHS and AdCAG-GFP-conditioned media or the AdCAGSTAC-conditioned media also showed a comparably smaller amount of cell lysis and MAC pixel intensity.

The permeability of the hepa-1c1c7 cells following exposure to NHS was analyzed to determine the physiological relevance of decreased MAC deposition resulting from STAC inhibition. ARPE-19 cells were contacted with either AdCAGSTAC or AdCAGGFP for three days, and the media were collected. Hepa1c1c7 cells were then incubated with the media and NHS at a concentration of 1%-3% (v/v). The amount of PI uptake in the cells was measured using FACS analysis.

Cells treated with HI-NHS were sorted to a location of lesser PI uptake than cells treated with NHS (greater PI uptake and cell death; FIG. 23 panel C). Data show that AdCAGSTAC-conditioned media reduced the amount of PI uptake at 2% NHS about nine-fold compared to cells contacted with control AdCAGGFP-conditioned media. Little or no PI uptake (i.e., less than about 10%) was detected in cells contacted with HI-NHS for either AdCAGSTAC-conditioned media or AdCAGGFP-conditioned media. These data show that AdCAGSTAC inhibited MAC deposition, PI uptake, and cell lysis.

Example 35

STAC Protects In vivo Complement Deposition on Murine Liver Vasculature

Figure 24A:
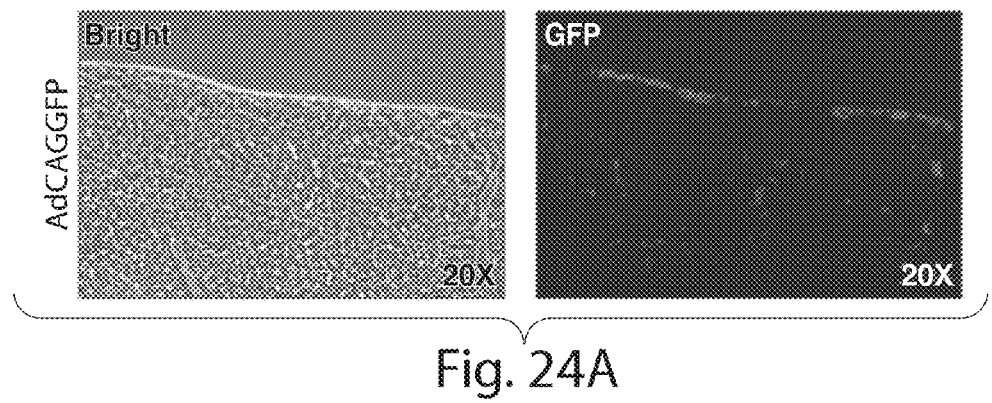
FIG. 24 panels A-C are a set of photomicrographs and a bar graph showing that endothelial cells of liver vasculature of C57/B16J mice pre-injected intraperitoneally with AdCAGSTAC vector seven days prior to left ventricle injection of anti-mPECAM1/NHS were observed to have less MAC staining compared to liver vasculature from mice pre-injected with AdCAGGFP vector.
Figure 24B:
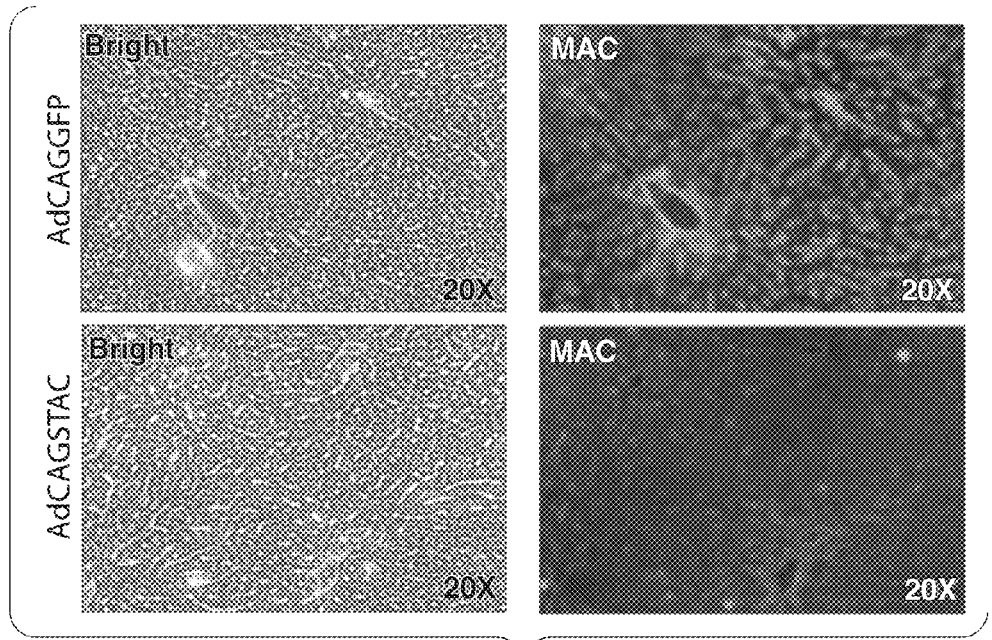
Figure 24C:
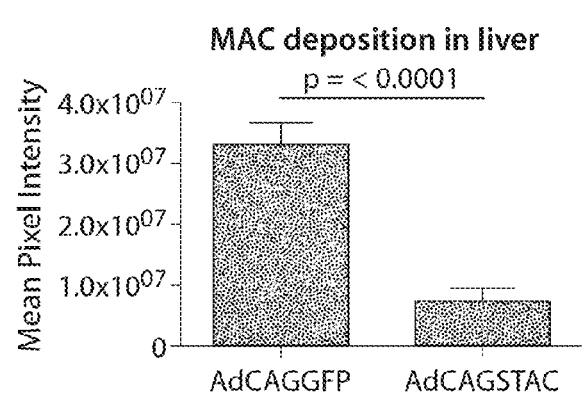

Vector AdCAGSTAC or control AdCAGGFP was injected ($5 \times 10^9$ particles) into the intraperitoneal (IP) space of C57/B16J mice to analyze ability of STAC to protect from complement activation in vivo. IP injection of the adenovirus resulted in a high degree of liver transduction because the adenovirus specifically transduces the Glisson's capsule that surrounds the liver (FIG. 24 panel A). After seven days an anti mouse PECAM antibody (200 µg in a volume of 200 µl) was injected into the left ventricle, causing binding of antibody to the endothelial lining of blood vessels. NHS (90% in PBS containing calcium and magnesium) was injected into the left ventricle causing complement deposition on the surface of endothelial cells of the liver vasculature.

Liver sections obtained from subjects injected with control vector AdCAGGFP showed significant negative changes in cell morphology (FIG. 24 panel B, left photomicrograph) compared to liver sections from subjects injected with AdCAGSTAC (FIG. 24 panel C, left photomicrograph). MAC staining was observed in the liver sections from subjects injected with AdCAGGFP (FIG. 24 panel B right photomicrograph). Liver sections of subjects injected with AdCAGSTAC showed little or no MAC staining (FIG. 24 panel B right photomicrograph). The vessels and cells of liver sections of subjects injected with AdCAGSTAC were observed to have reduced average MAC staining compared to the livers of mice injected with AdCAGGFP (FIG. 24 panels B and C respectively).

Quantitation of MAC pixel intensity in liver cross sections taken from the central region of the left lobe of the liver revealed a 79% decrease in MAC deposition in the AdCAG-STAC injected mice compared with those injected with AdCAGGFP (See FIG. 24 panel C), an extent of reduction that is statistically significant.

What is claimed is:

1. A pharmaceutical composition for treating a complement-related condition in a subject, the composition comprising an amino acid sequence as shown in SEQ ID NO: 1 comprising sequences from each of: a CD46 protein, a CD55 protein, and a CD59 protein.

2. A pharmaceutical composition for treating a complement-related condition in a subject, the composition comprising a chimeric soluble terminator of activated complement (STAC) protein, wherein the STAC protein comprises a sequence at least about 90% identical to SEQ ID NO:1 and comprises each of the CD46 protein, the CD55 protein, and the CD59 protein.

3. The composition according to claim 1 or claim 2 formulated in a dose effective to treat the subject for the complement-related condition.

4. The composition according to claim 1 or claim 2 formulated for ocular delivery.

5. The composition according to claim 1 or claim 2, wherein the composition further comprises a delivery vehicle engineered to target a cell or tissue, wherein the delivery vehicle is selected from the group of: a liposome, a lipid, a polycation, a peptide, a nanoparticle, a gold particle, and a polymer.

6. The composition according to claim 1 or claim 2 further comprising a pharmaceutically acceptable salt or a pharmaceutically acceptable emollient.

7. The composition according to claim 1 or claim 2 further comprising an agent selected from the group consisting of: anti-tumor, anti-coagulant, anti-viral, antibacterial, anti-mycobacterial, anti-fungal, anti-proliferative and anti-apoptotic.

* * * * *

```
                        SEQUENCE LISTING

<160> NUMBER OF SEQ ID NOS: 8

<210> SEQ ID NO 1
<211> LENGTH: 686
<212> TYPE: PRT
<213> ORGANISM: Artificial Sequence
<220> FEATURE:
<223> OTHER INFORMATION: The sequence has been designed and synthesized

<400> SEQUENCE: 1

Met Gly Ile Gln Gly Gly Ser Val Leu Phe Gly Leu Leu Val Leu
1               5                   10                  15

Ala Val Phe Cys His Ser Gly His Ser Leu Gln Cys Tyr Asn Cys
                20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
        50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Gly Gly Gly Gly Cys Glu Glu Pro Pro Thr
            100                 105                 110

Phe Glu Ala Met Glu Leu Ile Gly Lys Pro Lys Pro Tyr Tyr Glu Ile
        115                 120                 125

Gly Glu Arg Val Asp Tyr Lys Cys Lys Lys Gly Tyr Phe Tyr Ile Pro
    130                 135                 140

Pro Leu Ala Thr His Thr Ile Cys Asp Arg Asn His Thr Trp Leu Pro
145                 150                 155                 160

Val Ser Asp Asp Ala Cys Tyr Arg Glu Thr Cys Pro Tyr Ile Arg Asp
                165                 170                 175

Pro Leu Asn Gly Gln Ala Val Pro Ala Asn Gly Thr Tyr Glu Phe Gly
            180                 185                 190

Tyr Gln Met His Phe Ile Cys Asn Glu Gly Tyr Tyr Leu Ile Gly Glu
        195                 200                 205

Glu Ile Leu Tyr Cys Glu Leu Lys Gly Ser Val Ala Ile Trp Ser Gly
    210                 215                 220

Lys Pro Pro Ile Cys Glu Lys Val Leu Cys Thr Pro Pro Lys Ile
225                 230                 235                 240

Lys Asn Gly Lys His Thr Phe Ser Glu Val Glu Val Phe Glu Tyr Leu
                245                 250                 255

Asp Ala Val Thr Tyr Ser Cys Asp Pro Ala Pro Gly Pro Asp Pro Phe
            260                 265                 270

Ser Leu Ile Gly Glu Ser Thr Ile Tyr Cys Gly Asp Asn Ser Val Trp
        275                 280                 285

Ser Arg Ala Ala Pro Glu Cys Lys Val Val Lys Cys Arg Phe Pro Val
    290                 295                 300

Val Glu Asn Gly Lys Gln Ile Ser Gly Phe Gly Lys Lys Phe Tyr Tyr
```

```
305                 310                 315                 320
Lys Ala Thr Val Met Phe Glu Cys Asp Lys Gly Phe Tyr Leu Asp Gly
                325                 330                 335

Ser Asp Thr Ile Val Cys Asp Ser Asn Ser Thr Trp Asp Pro Pro Val
                340                 345                 350

Pro Lys Cys Leu Lys Val Gly Gly Gly Gly Asp Cys Gly Leu
                355                 360                 365

Pro Pro Asp Val Pro Asn Ala Gln Pro Ala Leu Glu Gly Arg Thr Ser
370                 375                 380

Phe Pro Glu Asp Thr Val Ile Thr Tyr Lys Cys Glu Glu Ser Phe Val
385                 390                 395                 400

Lys Ile Pro Gly Glu Lys Asp Ser Val Ile Cys Leu Lys Gly Ser Gln
                405                 410                 415

Trp Ser Asp Ile Glu Glu Phe Cys Asn Arg Ser Cys Glu Val Pro Thr
                420                 425                 430

Arg Leu Asn Ser Ala Ser Leu Lys Gln Pro Tyr Ile Thr Gln Asn Tyr
        435                 440                 445

Phe Pro Val Gly Thr Val Val Glu Tyr Glu Cys Arg Pro Gly Tyr Arg
        450                 455                 460

Arg Glu Pro Ser Leu Ser Pro Lys Leu Thr Cys Leu Gln Asn Leu Lys
465                 470                 475                 480

Trp Ser Thr Ala Val Glu Phe Cys Lys Lys Ser Cys Pro Asn Pro
                485                 490                 495

Gly Glu Ile Arg Asn Gly Gln Ile Asp Val Pro Gly Gly Ile Leu Phe
                500                 505                 510

Gly Ala Thr Ile Ser Phe Ser Cys Asn Thr Gly Tyr Lys Leu Phe Gly
                515                 520                 525

Ser Thr Ser Ser Phe Cys Leu Ile Ser Gly Ser Ser Val Gln Trp Ser
                530                 535                 540

Asp Pro Leu Pro Glu Cys Arg Glu Ile Tyr Cys Pro Ala Pro Pro Gln
545                 550                 555                 560

Ile Asp Asn Gly Ile Ile Gln Gly Glu Arg Asp His Tyr Gly Tyr Arg
                565                 570                 575

Gln Ser Val Thr Tyr Ala Cys Asn Lys Gly Phe Thr Met Ile Gly Glu
                580                 585                 590

His Ser Ile Tyr Cys Thr Val Asn Asn Asp Glu Gly Glu Trp Ser Gly
                595                 600                 605

Pro Pro Pro Glu Cys Arg Gly Lys Ser Leu Thr Ser Lys Val Pro Pro
610                 615                 620

Thr Val Gln Lys Pro Thr Thr Val Asn Val Pro Thr Thr Glu Val Ser
625                 630                 635                 640

Pro Thr Ser Gln Lys Thr Thr Thr Lys Thr Thr Thr Pro Asn Ala Gln
                645                 650                 655

Ala Thr Arg Ser Thr Pro Val Ser Arg Thr Thr Lys His Phe His Glu
                660                 665                 670

Thr Thr Pro Asn Lys Gly Ser Gly Thr Thr Ser Gly Thr Thr
                675                 680                 685

<210> SEQ ID NO 2
<211> LENGTH: 15
<212> TYPE: DNA
<213> ORGANISM: Artificial Sequence
<220> FEATURE:
<223> OTHER INFORMATION: The sequence has been designed and synthesized
```

<400> SEQUENCE: 2

```
ggaggcggag gtgga                                                    15
```

<210> SEQ ID NO 3
<211> LENGTH: 3219
<212> TYPE: DNA
<213> ORGANISM: Homo sapiens

<400> SEQUENCE: 3

```
tgagttgggg attgttgcgt cccatatctg gacccagaag ggacttccct gctcggctgg    60
ctctcggttt ctctgctttc ctccggagaa ataacagcgt cttccgcgcc gcgcatggag   120
cctcccggcc gccgcgagtg tccctttcct tcctggcgct ttcctgggtt gcttctggcg   180
gccatggtgt tgctgctgta ctccttctcc gatgcctgtg aggagccacc aacatttgaa   240
gctatggagc tcattggtaa accaaaaccc tactatgaga ttggtgaacg agtagattat   300
aagtgtaaaa aaggatactt ctatataacct cctcttgcca cccatactat ttgtgatcgg   360
aatcatacat ggctacctgt ctcagatgac gcctgttata gagaaacatg tccatatata   420
cgggatcctt aaatggcca agcagtccct gcaaatggga cttacgagtt tggttatcag   480
atgcacttta tttgtaatga gggttattac ttaattggtg aagaaattct atattgtgaa   540
cttaaaggat cagtagcaat ttggagcggt aagccccaa tatgtgaaaa ggttttgtgt   600
acaccacctc caaaaataaa aaatggaaaa cacaccttta gtgaagtaga agtatttgag   660
tatcttgatg cagtaactta tagttgtgat cctgcacctg gaccagatcc attttcactt   720
attggagaga gcacgattta tgtggtgac aattcagtgt ggagtcgtgc tgctccagag   780
tgtaaagtgg tcaaatgtcg atttccagta gtcgaaaatg gaaaacagat atcaggattt   840
ggaaaaaaat tttactacaa agcaacagtt atgtttgaat gcgataaggg tttttacctc   900
gatggcagcg acacaattgt ctgtgacagt aacagtactt gggatccccc agttccaaag   960
tgtcttaaag tgtcgacttc ttccactaca aaatctccag cgtccagtgc ctcaggtcct  1020
aggcctactt acaagcctcc agtctcaaat tatccaggat atcctaaacc tgaggaagga  1080
atacttgaca gtttggatgt ttgggtcatt gctgtgattg ttattgccat agttgttgga  1140
gttgcagtaa tttgtgttgt cccgtacaga tatcttcaaa ggaggaagaa gaaagggaaa  1200
gcagatggtg gagctgaata tgccacttac cagactaaat caaccactcc agcagagcag  1260
agaggctgaa tagattccac aacctggttt gccagttcat cttttgactc tattaaaatc  1320
ttcaatagtt gttattctgt agtttcactc tcatgagtgc aactgtggct tagctaatat  1380
tgcaatgtgg cttgaatgta ggtagcatcc tttgatgctt cttttgaaact tgtatgaatt  1440
tgggtatgaa cagattgcct gctttcccctt aaataacact tagatttatt ggaccagtca  1500
gcacagcatg cctggttgta ttaaagcagg gatatgctgt attttataaa attggcaaaa  1560
ttagagaaat atagttcaca atgaaattat attttctttg taaagaaagt ggcttgaaat  1620
ctttttttgtt caaagattaa tgccaactct taagattatt ctttcaccaa ctatagaatg  1680
tattttatat atcgttcatt gtaaaaagcc cttaaaaata tgtgtatact actttggctc  1740
ttgtgcataa aaacaagaac actgaaaatt gggaatatgc acaaacttgg cttctttaac  1800
caagaatatt attggaaaat tctctaaaag ttaatagggt aaattctcta ttttttgtaa  1860
tgtgttcggt gatttcagaa agctagaaag tgtatgtgtg gcatttgttt tcacttttta  1920
aaacatccct aactgatcga atatatcagt aatttcagaa tcagatgcat cctttcataa  1980
gaagtgagag gactctgaca gccataacag gagtgccact tcatggtgcg aagtgaacac  2040
```

| | | | |
|---|---|---|---|
| tgtagtcttg | ttgttttccc | aaagagaact | ccgtatgttc tcttaggttg agtaacccac | 2100 |
| tctgaattct | ggttacatgt | gtttttctct | ccctccttaa ataaagagag gggttaaaca | 2160 |
| tgccctctaa | aagtaggtgg | ttttgaagag | aataaattca tcagataacc tcaagtcaca | 2220 |
| tgagaatctt | agtccattta | cattgccttg | gctagtaaaa gccatctatg tatatgtctt | 2280 |
| acctcatctc | ctaaaaggca | gagtacaaag | taagccatgt atctcaggaa ggtaacttca | 2340 |
| ttttgtctat | tgctgttga | ttgtaccaag | ggatggaaga agtaaatata gctcaggtag | 2400 |
| cactttatac | tcaggcagat | ctcagccctc | tactgagtcc cttagccaag cagtttcttt | 2460 |
| caaagaagcc | agcaggcgaa | aagcagggac | tgccactgca tttcatatca cactgttaaa | 2520 |
| agttgtgttt | tgaaatttta | tgtttagttg | cacaaattgg gccaaagaaa cattgccttg | 2580 |
| aggaagatat | gattgaaaaa | tcaagagtgt | agaagaataa atactgtttt actgtccaaa | 2640 |
| gacatgttta | tagtgctctg | taaatgttcc | tttcctttgt agtctctggc aagatgcttt | 2700 |
| aggaagataa | aagtttgagg | agaacaaaca | ggaattctga attaagcaca gagttgaagt | 2760 |
| ttatacccgt | tcacatgct | tttcaagaat | gtcgcaatta ctaagaagca gataatggtg | 2820 |
| ttttttagaa | acctaattga | agtatattca | accaaatact ttaatgtata aaataaaat | 2880 |
| tatacaatat | acttgtatag | cagtttctgc | ttcacatttg atttttttcaa atttaatatt | 2940 |
| tatattagag | atctatatat | gtataaatat | gtattttgtc aaatttgtta cttaaatata | 3000 |
| tagagaccag | ttttctctgg | aagtttgttt | aaatgacaga agcgtatatg aattcaagaa | 3060 |
| aatttaagct | gcaaaaatgt | atttgctata | aaatgagaag tctcactgat agaggttctt | 3120 |
| tattgctcat | tttttaaaaa | atggactctt | gaaatctgtt aaaataaaat tgtacatttg | 3180 |
| gagatgtttc | aaaaaaaaaa | aagaaaaaaa | aaaaaaaa | 3219 |

<210> SEQ ID NO 4
<211> LENGTH: 384
<212> TYPE: PRT
<213> ORGANISM: Homo sapiens

<400> SEQUENCE: 4

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Ala Cys Tyr Arg
            85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

```
Leu Cys Thr Pro Pro Lys Ile Lys Asn Gly Lys His Thr Phe Ser
            165                 170                 175

Glu Val Glu Val Phe Glu Tyr Leu Asp Ala Val Thr Tyr Ser Cys Asp
        180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
            245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Ser Thr
        275                 280                 285

Ser Ser Thr Thr Lys Ser Pro Ala Ser Ser Ala Ser Gly Pro Arg Pro
        290                 295                 300

Thr Tyr Lys Pro Pro Val Ser Asn Tyr Pro Gly Tyr Pro Lys Pro Glu
305                 310                 315                 320

Glu Gly Ile Leu Asp Ser Leu Asp Val Trp Val Ile Ala Val Ile Val
            325                 330                 335

Ile Ala Ile Val Val Gly Val Ala Val Ile Cys Val Val Pro Tyr Arg
            340                 345                 350

Tyr Leu Gln Arg Arg Lys Lys Lys Gly Lys Ala Asp Gly Gly Ala Glu
        355                 360                 365

Tyr Ala Thr Tyr Gln Thr Lys Ser Thr Thr Pro Ala Glu Gln Arg Gly
370                 375                 380

<210> SEQ ID NO 5
<211> LENGTH: 1357
<212> TYPE: DNA
<213> ORGANISM: Homo sapiens

<400> SEQUENCE: 5
gcaactcgct ccggccgctg ggcgtagctg cgactcggcg gagtcccggc ggcgcgtcct      60
tgttctaacc cggcgcgcca tgaccgtcgc gcggccgagc gtgcccgcgg cgctgcccct     120
cctcggggag ctgccccggc tgctgctgct ggtgctgttg tgcctgccgg ccgtgtgggg     180
tgactgtggc cttcccccag atgtacctaa tgcccagcca gctttggaag ccgtacaag     240 ttttcccgag gatactgtaa taacgtacaa atgtgaagaa agctttgtga aaattcctgg     300
cgagaaggac tcagtgatct gccttaaggg cagtcaatgg tcagatattg aagagttctg     360
caatcgtagc tgcgaggtgc aacaaggct aaattctgca tccctcaaac agccttatat     420
cactcagaat tatttccag tcggtactgt tgtggaatat gagtgccgtc caggttacag     480
aagagaacct tctctatcac caaaactaac ttgccttcag aatttaaaat ggtccacagc     540
agtcgaattt tgtaaaaaga atcatgccc taatccggga gaaatacgaa atggtcagat     600
tgatgtacca ggtggcatat tatttggtgc aaccatctcc ttctcatgta acacagggta     660
caaattattt ggctcgactt ctagtttttg tcttatttca ggcagctctg tccagtggag     720
tgacccgttg ccagagtgca gagaaattta ttgtccagca ccaccacaaa ttgacaatgg     780
aataattcaa ggggaacgtg accattatgg atatagacag tctgtaacgt atgcatgtaa     840
taaaggattc accatgattg agagcactc tatttattgt actgtgaata atgatgaagg     900
```

```
agagtggagt ggcccaccac ctgaatgcag aggaaaatct ctaacttcca aggtcccacc    960
aacagttcag aaacctacca cagtaaatgt tccaactaca gaagtctcac caacttctca   1020
gaaaaccacc acaaaaacca ccacaccaaa tgctcaagca acacggagta cacctgtttc   1080
caggacaacc aagcattttc atgaaacaac cccaaataaa ggaagtggaa ccacttcagg   1140
tactacccgt cttctatctg ggcacacgtg tttcacgttg acaggtttgc ttgggacgct   1200
agtaaccatg ggcttgctga cttagccaaa gaagagttaa gaagaaaata cacacaagta   1260
tacagactgt tcctagtttc ttagacttat ctgcatattg gataaaataa atgcaattgt   1320
gctcttcaaa aaaaaaaaaa aaaaaaaaaa aaaaaaa                            1357
```

<210> SEQ ID NO 6
<211> LENGTH: 381
<212> TYPE: PRT
<213> ORGANISM: Homo sapiens

<400> SEQUENCE: 6

```
Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
            35                  40                  45

Leu Glu Gly Arg Thr Ser Phe Pro Glu Asp Thr Val Ile Thr Tyr Lys
        50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

Glu Gly Glu Trp Ser Gly Pro Pro Pro Glu Cys Arg Gly Lys Ser Leu
        275                 280                 285
```

```
Thr Ser Lys Val Pro Pro Thr Val Gln Lys Pro Thr Thr Val Asn Val
    290                 295                 300
Pro Thr Thr Glu Val Ser Pro Thr Ser Gln Lys Thr Thr Thr Lys Thr
305                 310                 315                 320
Thr Thr Pro Asn Ala Gln Ala Thr Arg Ser Thr Pro Val Ser Arg Thr
                325                 330                 335
Thr Lys His Phe His Glu Thr Thr Pro Asn Lys Gly Ser Gly Thr Thr
                340                 345                 350
Ser Gly Thr Thr Arg Leu Leu Ser Gly His Thr Cys Phe Thr Leu Thr
            355                 360                 365
Gly Leu Leu Gly Thr Leu Val Thr Met Gly Leu Leu Thr
370                 375                 380

<210> SEQ ID NO 7
<211> LENGTH: 5088
<212> TYPE: DNA
<213> ORGANISM: Mus musculus

<400> SEQUENCE: 7 ctgccccttca cccttcatt ccttccacct ttttccttca ctatgggacc agcttcaggg      60
tcccagctac tagtgctact gctgctgttg gccagctccc cattagctct ggggatcccc     120
atgtattcca tcattactcc caatgtccta cggctggaga gcgaagagac catcgtactg     180
gaggcccacg atgctcaggg tgacatccca gtcacagtca ctgtgcaaga cttcctaaag     240
aggcaagtgc tgaccagtga agacagtg ttgacaggag ccagtggaca tctgagaagc     300
gtctccatca agattccagc cagtaaggaa ttcaactcag ataaggaggg gcacaagtac     360
gtgacagtgg tggcaaactt cggggaaacg gtggtggaga aagcagtgat ggtaagcttc     420
cagagtgggt acctcttcat ccagacagac aagaccatct acacccctgg ctccactgtc     480
ttatatcgga tcttcactgt ggacaacaac ctactgcccg tgggcaagac agtcgtcatc     540
ctcattgaga cccccgatgg cattcctgtc aagagagaca ttctgtcttc aacaaccaa     600
cacggcatct tgcctttgtc ttggaacatt cctgaactgg tcaacatggg gcagtggaag     660
atccgagcct tttacgaaca tgcgccaag cagatcttct ccgcagagtt tgaggtgaag     720
gaatacgtgc tgcccagttt tgaggtccgg gtggagccca cagagacatt ttattacatc     780
gatgacccaa atgcctggaa agtttccatc atagccaagt tcctgtacgg gaaaaacgtg     840
gacgggacag ccttcgtgat ttttggggtc caggatggcg ataagaagat ttctctggcc     900
cactccctca cgcgcgtagt gattgaggat ggtgtggggg atgcagtgct gacccggaag     960
gtgctgatgg agggggtacg gccttccaac gccgacgccc tggtggggaa gtccctgtat    1020
gtctccgtca ctgtcatcct gcactcaggt agtgacatgg tagaggcaga gcgcagtggg    1080
atcccgattg tcacttcccc gtaccagatc cacttcacca agacacccaa attcttcaag    1140
ccagccatgc cctttgacct catggtgttc gtgaccaacc ccgatggctc tccggccagc    1200
aaagtgctgg tggtcactca gggatctaat gcaaaggctc tcacccaaga tgatggcgtg    1260
gccaagctaa gcatcaacac acccaacagc cgccaacccc tgaccatcac agtccgcacc    1320
aagaaggaca ctctcccaga atcacggcag gccaccaaga caatggaggc catccctac    1380
agcactatgc acaactccaa caactaccta cacttgtcag tgtcacgaat ggagctcaag    1440
ccgggggaca acctcaatgt caacttccac ctgcgcacag acccaggcca tgaggccaag    1500
atccgatact acacctacct ggttatgaac aagggggaagc tcctgaaggc aggccgccag    1560
gttcgggagc ctggccagga cctggtggtc ttgtccctgc ccatcactcc agagtttatt    1620
```

```
ccttcatttc gcctggtggc ttactacacc ctgattggag ctagtggcca gagggaggtg    1680
gtggctgact ctgtgtgggt ggatgtgaag gattcctgta ttggcacgct ggtggtgaag    1740
ggtgacccaa gagataacca tctcgcacct gggcaacaaa cgacactcag gattgaagga    1800 aaccagggggg cccgagtggg gctagtggct gtggacaagg gagtgtttgt gctgaacaag    1860
aagaacaaac tcacacagag caagatctgg gatgtggtag agaaggcaga cattggctgc    1920
accccaggca gtgggaagaa ctatgctggt gtcttcatgg atgcaggcct ggccttcaag    1980
acaagccaag gactgcagac tgaacagaga gcagatcttg agtgcaccaa gccagcagcc    2040
cgccgccgtc gctcagtaca gttgatgaaa agaaggatgg acaaagctgg tcagtacact    2100
gacaagggtc ttcggaagtg ttgtgaggat ggtatgcggg atatccctat gagatacagc    2160
tgccagcgcc gggcacgcct catcacccag ggcgagaact gcataaaggc cttcatagac    2220
tgctgcaacc acatcaccaa gctgcgtgaa caacacagaa gagaccacgt gctgggcctg    2280
gccaggagtg aattggagga agacataatt ccagaagaag atattatctc tagaagccac    2340
ttcccacaga gctggttgtg gaccatagaa gagttgaaag aaccagagaa aaatggaatc    2400
tctacgaagg tcatgaacat ctttctcaaa gattccatca ccacctggga gattctggca    2460
gtgagcttgt cagacaagaa agggatctgt gtggcagacc cctatgagat cagagtgatg    2520
caggacttct tcattgacct gcggctgccc tactctgtag tgcgcaacga acaggtggag    2580
atcagagctg tgctcttcaa ctaccgtgaa caggaggaac ttaaggtgag ggtggaactg    2640
ttgcataatc cagcccttctg cagcatggcc accgccaaga atcgctactt ccagaccatc    2700
aaaatccctc ccaagtcctc ggtggctgta ccgtatgtca ttgtcccctt gaagatcggc    2760
caacaagagg tggaggtcaa ggctgctgtc ttcaatcact tcatcagtga tggtgtcaag    2820
aagacactga aggtcgtgcc agaaggaatg agaatcaaca aaactgtggc catccataca    2880
ctggacccag agaagctcgg tcaagggggga gtgcagaagg tggatgtgcc tgccgcagac    2940
cttagcgacc aagtgccaga cacagactct gagaccagaa ttatcctgca agggagcccg    3000
gtggttcaga tggctgaaga tgctgtggac ggggagcggc tgaaacacct gatcgtgacc    3060
cccgcaggct gtggggaaca aacatgatt ggcatgacac caacagtcat tgcggtacac    3120
tacctggacc agaccgaaca gtgggagaag ttcggcatag agaagaggca agaggccctg    3180
gagctcatca agaaagggta cacccagcag ctggccttca acagcccag ctctgcctat    3240 gctgccttca caaccggcc ccccagcacc tggctgacag cctacgtggt caaggtcttc    3300
tctctagctg ccaacctcat cgccatcgac tctcacgtcc tgtgtggggc tgttaaatgg    3360
ttgattctgg agaaacagaa gccggatggt gtctttcagg aggatgggcc cgtgattcac    3420
caagaaatga ttggtggctt ccggaacgcc aaggaggcag atgtgtcact cacagccttc    3480
gtcctcatcg cactgcagga agccagggac atctgtgagg ggcaggtcaa tagccttcct    3540
gggagcatca acaaggcagg ggagtatatt gaagccagtt acatgaacct gcagagacca    3600
tacacagtgg ccattgctgg gtatgccctg gccctgatga caaactgga ggaaccttac    3660 ctcggcaagt ttctgaacac agccaaagat cggaaccgct gggaggagcc tgaccagcag    3720
ctctacaacg tagaggccac atcctacgcc ctcctggccc tgctgctgct gaaagacttt    3780
gactctgtgc cccctgtagt gcgctggctc aatgagcaaa gatactacgg aggcggctat    3840
ggctccaccc aggctacctt catggtattc caagccttgg cccaatatca aacagatgtc    3900
cctgaccata aggacttgaa catggatgtg tccttccacc tccccagccg tagctctgca    3960
```

```
accacgtttc gcctgctctg ggaaaatggc aacctcctgc gatcggaaga gaccaagcaa    4020
aatgaggcct tctctctaac agccaaagga aaaggccgag gcacattgtc ggtggtggca    4080
gtgtatcatg ccaaactcaa aagcaaagtc acctgcaaga gtttgacct caggtcagc     4140 ataagaccag cccctgagac agccaagaag cccgaggaag ccaagaatac catgttcctt   4200
gaaatctgca ccaagtactt gggagatgtg gacgccacta tgtccatcct ggacatctcc   4260
atgatgactg gctttgctcc agacacaaag gacctggaac tgctggcctc tggagtagat   4320
agatacatct ccaagtacga gatgaacaaa gccttctcca acaagaacac cctcatcatc   4380
tacctagaaa agatttcaca caccgaagaa gactgcctga ccttcaaagt tcaccagtac   4440
tttaatgtgg gacttatcca gcccgggtcg gtcaaggtct actcctatta caacctcgag   4500
gaatcatgca cccggttcta tcatccagag aaggacgatg ggatgctcag caagctgtgc   4560
cacagtgaaa tgtgccggtg tgctgaagag aactgcttca tgcaacagtc acaggagaag   4620
atcaacctga atgtccggct agacaaggct tgtgagcccg gagtcgacta tgtgtacaag   4680
accgagctaa ccaacataga gctgttggat gattttgatg agtacaccat gaccatccag   4740
caggtcatca agtcaggctc agatgaggtg caggcagggc agcaacgcaa gttcatcagc   4800
cacatcaagt gcagaaacgc cctgaagctg cagaaaggga agaagtacct catgtggggc   4860
ctctcctctg acctctgggg agaaaagccc aacaccagct acatcattgg gaaggacacg   4920
tgggtggagc actggcctga ggcagaagaa tgccaggatc agaagtacca gaacagtgc    4980 gaagaacttg gggcattcac agaatctatg gtggtttatg gttgtcccaa ctgactacag   5040
cccagccctc taataaagct tcagttgtat ttcaaaaaaa aaaaaaaa                 5088
```

<210> SEQ ID NO 8
<211> LENGTH: 1663
<212> TYPE: PRT
<213> ORGANISM: Mus musculus

<400> SEQUENCE: 8

```
Met Gly Pro Ala Ser Gly Ser Gln Leu Leu Val Leu Leu Leu Leu
1               5                   10                  15

Ala Ser Ser Pro Leu Ala Leu Gly Ile Pro Met Tyr Ser Ile Ile Thr
            20                  25                  30

Pro Asn Val Leu Arg Leu Glu Ser Glu Glu Thr Ile Val Leu Glu Ala
        35                  40                  45

His Asp Ala Gln Gly Asp Ile Pro Val Thr Val Thr Val Gln Asp Phe
    50                  55                  60

Leu Lys Arg Gln Val Leu Thr Ser Glu Lys Thr Val Leu Thr Gly Ala
65                  70                  75                  80

Ser Gly His Leu Arg Ser Val Ser Ile Lys Ile Pro Ala Ser Lys Glu
                85                  90                  95

Phe Asn Ser Asp Lys Glu Gly His Lys Tyr Val Thr Val Val Ala Asn
            100                 105                 110

Phe Gly Glu Thr Val Val Glu Lys Ala Val Met Val Ser Phe Gln Ser
        115                 120                 125

Gly Tyr Leu Phe Ile Gln Thr Asp Lys Thr Ile Tyr Thr Pro Gly Ser
    130                 135                 140

Thr Val Leu Tyr Arg Ile Phe Thr Val Asp Asn Asn Leu Leu Pro Val
145                 150                 155                 160

Gly Lys Thr Val Val Ile Leu Ile Glu Thr Pro Asp Gly Ile Pro Val
                165                 170                 175
```

```
Lys Arg Asp Ile Leu Ser Ser Asn Gln His Gly Ile Leu Pro Leu
                180                 185                 190
Ser Trp Asn Ile Pro Glu Leu Val Asn Met Gly Gln Trp Lys Ile Arg
        195                 200                 205
Ala Phe Tyr Glu His Ala Pro Lys Gln Ile Phe Ser Ala Glu Phe Glu
    210                 215                 220
Val Lys Glu Tyr Val Leu Pro Ser Phe Glu Val Arg Val Glu Pro Thr
225                 230                 235                 240
Glu Thr Phe Tyr Tyr Ile Asp Asp Pro Asn Gly Leu Glu Val Ser Ile
                245                 250                 255
Ile Ala Lys Phe Leu Tyr Gly Lys Asn Val Asp Gly Thr Ala Phe Val
            260                 265                 270
Ile Phe Gly Val Gln Asp Gly Asp Lys Lys Ile Ser Leu Ala His Ser
        275                 280                 285
Leu Thr Arg Val Val Ile Glu Asp Gly Val Gly Asp Ala Val Leu Thr
    290                 295                 300
Arg Lys Val Leu Met Glu Gly Val Arg Pro Ser Asn Ala Asp Ala Leu
305                 310                 315                 320
Val Gly Lys Ser Leu Tyr Val Ser Val Thr Val Ile Leu His Ser Gly
                325                 330                 335
Ser Asp Met Val Glu Ala Glu Arg Ser Gly Ile Pro Ile Val Thr Ser
            340                 345                 350
Pro Tyr Gln Ile His Phe Thr Lys Thr Pro Lys Phe Phe Lys Pro Ala
        355                 360                 365
Met Pro Phe Asp Leu Met Val Phe Val Thr Asn Pro Asp Gly Ser Pro
    370                 375                 380
Ala Ser Lys Val Leu Val Val Thr Gln Gly Ser Asn Ala Lys Ala Leu
385                 390                 395                 400
Thr Gln Asp Asp Gly Val Ala Lys Leu Ser Ile Asn Thr Pro Asn Ser
                405                 410                 415
Arg Gln Pro Leu Thr Ile Thr Val Arg Thr Lys Lys Asp Thr Leu Pro
            420                 425                 430
Glu Ser Arg Gln Ala Thr Lys Thr Met Glu Ala His Pro Tyr Ser Thr
        435                 440                 445
Met His Asn Ser Asn Asn Tyr Leu His Leu Ser Val Ser Arg Met Glu
    450                 455                 460
Leu Lys Pro Gly Asp Asn Leu Asn Val Asn Phe His Leu Arg Thr Asp
465                 470                 475                 480
Pro Gly His Glu Ala Lys Ile Arg Tyr Tyr Thr Tyr Leu Val Met Asn
                485                 490                 495
Lys Gly Lys Leu Leu Lys Ala Gly Arg Gln Val Arg Glu Pro Gly Gln
            500                 505                 510
Asp Leu Val Val Leu Ser Leu Pro Ile Thr Pro Glu Phe Ile Pro Ser
        515                 520                 525
Phe Arg Leu Val Ala Tyr Tyr Thr Leu Ile Gly Ala Ser Gly Gln Arg
    530                 535                 540
Glu Val Val Ala Asp Ser Val Trp Val Asp Val Lys Asp Ser Cys Ile
545                 550                 555                 560
Gly Thr Leu Val Val Lys Gly Asp Pro Arg Asp Asn His Leu Ala Pro
                565                 570                 575
Gly Gln Gln Thr Thr Leu Arg Ile Glu Gly Asn Gln Gly Ala Arg Val
            580                 585                 590
Gly Leu Val Ala Val Asp Lys Gly Val Phe Val Leu Asn Lys Lys Asn
```

```
              595                 600                 605
Lys Leu Thr Gln Ser Lys Ile Trp Asp Val Val Glu Lys Ala Asp Ile
    610                 615                 620
Gly Cys Thr Pro Gly Ser Gly Lys Asn Tyr Ala Gly Val Phe Met Asp
625                 630                 635                 640
Ala Gly Leu Ala Phe Lys Thr Ser Gln Gly Leu Gln Thr Glu Gln Arg
                645                 650                 655
Ala Asp Leu Glu Cys Thr Lys Pro Ala Ala Arg Arg Arg Arg Ser Val
                660                 665                 670
Gln Leu Met Glu Arg Arg Met Asp Lys Ala Gly Gln Tyr Thr Asp Lys
            675                 680                 685
Gly Leu Arg Lys Cys Cys Glu Asp Gly Met Arg Asp Ile Pro Met Arg
        690                 695                 700
Tyr Ser Cys Gln Arg Arg Ala Arg Leu Ile Thr Gln Gly Glu Asn Cys
705                 710                 715                 720
Ile Lys Ala Phe Ile Asp Cys Cys Asn His Ile Thr Lys Leu Arg Glu
                725                 730                 735
Gln His Arg Arg Asp His Val Leu Gly Leu Ala Arg Ser Glu Leu Glu
            740                 745                 750
Glu Asp Ile Ile Pro Glu Asp Ile Ile Ser Arg Ser His Phe Pro
        755                 760                 765
Gln Ser Trp Leu Trp Thr Ile Glu Glu Leu Lys Glu Pro Glu Lys Asn
770                 775                 780
Gly Ile Ser Thr Lys Val Met Asn Ile Phe Leu Lys Asp Ser Ile Thr
785                 790                 795                 800
Thr Trp Glu Ile Leu Ala Val Ser Leu Ser Asp Lys Lys Gly Ile Cys
                805                 810                 815
Val Ala Asp Pro Tyr Glu Ile Arg Val Met Gln Asp Phe Phe Ile Asp
                820                 825                 830
Leu Arg Leu Pro Tyr Ser Val Val Arg Asn Glu Gln Val Glu Ile Arg
            835                 840                 845
Ala Val Leu Phe Asn Tyr Arg Glu Gln Glu Glu Leu Lys Val Arg Val
    850                 855                 860
Glu Leu Leu His Asn Pro Ala Phe Cys Ser Met Ala Thr Ala Lys Asn
865                 870                 875                 880
Arg Tyr Phe Gln Thr Ile Lys Ile Pro Pro Lys Ser Ser Val Ala Val
                885                 890                 895
Pro Tyr Val Ile Val Pro Leu Lys Ile Gly Gln Gln Glu Val Glu Val
                900                 905                 910
Lys Ala Ala Val Phe Asn His Phe Ile Ser Asp Gly Val Lys Lys Thr
            915                 920                 925
Leu Lys Val Val Pro Glu Gly Met Arg Ile Asn Lys Thr Val Ala Ile
        930                 935                 940
His Thr Leu Asp Pro Glu Lys Leu Gly Gln Gly Val Gln Lys Val
945                 950                 955                 960
Asp Val Pro Ala Ala Asp Leu Ser Asp Gln Val Pro Asp Thr Asp Ser
                965                 970                 975
Glu Thr Arg Ile Ile Leu Gln Gly Ser Pro Val Val Gln Met Ala Glu
            980                 985                 990
Asp Ala Val Asp Gly Glu Arg Leu  Lys His Leu Ile Val Thr Pro Ala
        995                 1000                1005
Gly Cys  Gly Glu Gln Asn Met  Ile Gly Met Thr Pro  Thr Val Ile
    1010                1015                1020
```

```
Ala Val His Tyr Leu Asp Gln Thr Glu Gln Trp Glu Lys Phe Gly
    1025                1030                1035

Ile Glu Lys Arg Gln Glu Ala Leu Glu Leu Ile Lys Lys Gly Tyr
    1040                1045                1050

Thr Gln Gln Leu Ala Phe Lys Gln Pro Ser Ser Ala Tyr Ala Ala
    1055                1060                1065

Phe Asn Asn Arg Pro Pro Ser Thr Trp Leu Thr Ala Tyr Val Val
    1070                1075                1080

Lys Val Phe Ser Leu Ala Ala Asn Leu Ile Ala Ile Asp Ser His
    1085                1090                1095

Val Leu Cys Gly Ala Val Lys Trp Leu Ile Leu Glu Lys Gln Lys
    1100                1105                1110

Pro Asp Gly Val Phe Gln Glu Asp Gly Pro Val Ile His Gln Glu
    1115                1120                1125

Met Ile Gly Gly Phe Arg Asn Ala Lys Glu Ala Asp Val Ser Leu
    1130                1135                1140

Thr Ala Phe Val Leu Ile Ala Leu Gln Glu Ala Arg Asp Ile Cys
    1145                1150                1155

Glu Gly Gln Val Asn Ser Leu Pro Gly Ser Ile Asn Lys Ala Gly
    1160                1165                1170

Glu Tyr Ile Glu Ala Ser Tyr Met Asn Leu Gln Arg Pro Tyr Thr
    1175                1180                1185

Val Ala Ile Ala Gly Tyr Ala Leu Ala Leu Met Asn Lys Leu Glu
    1190                1195                1200

Glu Pro Tyr Leu Gly Lys Phe Leu Asn Thr Ala Lys Asp Arg Asn
    1205                1210                1215

Arg Trp Glu Glu Pro Asp Gln Gln Leu Tyr Asn Val Glu Ala Thr
    1220                1225                1230

Ser Tyr Ala Leu Leu Ala Leu Leu Leu Lys Asp Phe Asp Ser
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Thr Asp Val Pro Asp His Lys Asp Leu Asn
    1280                1285                1290

Met Asp Val Ser Phe His Leu Pro Ser Arg Ser Ser Ala Thr Thr
    1295                1300                1305

Phe Arg Leu Leu Trp Glu Asn Gly Asn Leu Leu Arg Ser Glu Glu
    1310                1315                1320

Thr Lys Gln Asn Glu Ala Phe Ser Leu Thr Ala Lys Gly Lys Gly
    1325                1330                1335

Arg Gly Thr Leu Ser Val Val Ala Val Tyr His Ala Lys Leu Lys
    1340                1345                1350

Ser Lys Val Thr Cys Lys Lys Phe Asp Leu Arg Val Ser Ile Arg
    1355                1360                1365

Pro Ala Pro Glu Thr Ala Lys Lys Pro Glu Glu Ala Lys Asn Thr
    1370                1375                1380

Met Phe Leu Glu Ile Cys Thr Lys Tyr Leu Gly Asp Val Asp Ala
    1385                1390                1395

Thr Met Ser Ile Leu Asp Ile Ser Met Met Thr Gly Phe Ala Pro
    1400                1405                1410
```

-continued

```
Asp Thr Lys Asp Leu Glu Leu Leu Ala Ser Gly Val Asp Arg Tyr
    1415            1420                1425

Ile Ser Lys Tyr Glu Met Asn Lys Ala Phe Ser Asn Lys Asn Thr
    1430            1435                1440

Leu Ile Ile Tyr Leu Glu Lys Ile Ser His Thr Glu Glu Asp Cys
    1445            1450                1455

Leu Thr Phe Lys Val His Gln Tyr Phe Asn Val Gly Leu Ile Gln
    1460            1465                1470

Pro Gly Ser Val Lys Val Tyr Ser Tyr Tyr Asn Leu Glu Glu Ser
    1475            1480                1485

Cys Thr Arg Phe Tyr His Pro Glu Lys Asp Asp Gly Met Leu Ser
    1490            1495                1500

Lys Leu Cys His Ser Glu Met Cys Arg Cys Ala Glu Glu Asn Cys
    1505            1510                1515

Phe Met Gln Gln Ser Gln Glu Lys Ile Asn Leu Asn Val Arg Leu
    1520            1525                1530

Asp Lys Ala Cys Glu Pro Gly Val Asp Tyr Val Tyr Lys Thr Glu
    1535            1540                1545

Leu Thr Asn Ile Glu Leu Leu Asp Asp Phe Asp Glu Tyr Thr Met
    1550            1555                1560

Thr Ile Gln Gln Val Ile Lys Ser Gly Ser Asp Glu Val Gln Ala
    1565            1570                1575

Gly Gln Gln Arg Lys Phe Ile Ser His Ile Lys Cys Arg Asn Ala
    1580            1585                1590

Leu Lys Leu Gln Lys Gly Lys Lys Tyr Leu Met Trp Gly Leu Ser
    1595            1600                1605

Ser Asp Leu Trp Gly Glu Lys Pro Asn Thr Ser Tyr Ile Ile Gly
    1610            1615                1620

Lys Asp Thr Trp Val Glu His Trp Pro Glu Ala Glu Glu Cys Gln
    1625            1630                1635

Asp Gln Lys Tyr Gln Lys Gln Cys Glu Glu Leu Gly Ala Phe Thr
    1640            1645                1650

Glu Ser Met Val Val Tyr Gly Cys Pro Asn
    1655            1660
```